US010400001B2

United States Patent
Konno et al.

(10) Patent No.: US 10,400,001 B2
(45) Date of Patent: Sep. 3, 2019

(54) HETEROLEPTIC IRIDIUM COMPLEX, AND LIGHT-EMITTING MATERIAL AND ORGANIC LIGHT-EMITTING ELEMENT USING COMPOUND

(71) Applicants: NATIONAL INSTITUTE OF ADVANCED INDUSTRIAL SCIENCE AND TECHNOLOGY, Tokyo (JP); FURUYA METAL CO., LTD., Tokyo (JP)

(72) Inventors: Hideo Konno, Ibaraki (JP); Yoshiro Sugita, Tokyo (JP); Takashi Ito, Tokyo (JP)

(73) Assignees: NATIONAL INSTITUTE OF ADVANCED INDUSTRIAL SCIENCE AND TECHNOLOGY, Tokyo (JP); FURUYA METAL CO., LTD., Tokyo (JP)

(*) Notice: Subject to any disclaimer, the term of this patent is extended or adjusted under 35 U.S.C. 154(b) by 0 days.

(21) Appl. No.: 15/551,068

(22) PCT Filed: Mar. 8, 2016

(86) PCT No.: PCT/JP2016/057088
§ 371 (c)(1),
(2) Date: Aug. 15, 2017

(87) PCT Pub. No.: WO2016/143770
PCT Pub. Date: Sep. 15, 2016

(65) Prior Publication Data
US 2018/0066001 A1 Mar. 8, 2018

(30) Foreign Application Priority Data
Mar. 10, 2015 (JP) .................................. 2015-047705

(51) Int. Cl.
*C07F 15/00* (2006.01)
*H01L 51/00* (2006.01)
(Continued)

(52) U.S. Cl.
CPC .......... *C07F 15/0033* (2013.01); *C09K 11/06* (2013.01); *H01L 51/0085* (2013.01);
(Continued)

(58) Field of Classification Search
CPC .......................... H01L 51/0058; C07F 15/0033
See application file for complete search history.

(56) References Cited

U.S. PATENT DOCUMENTS 7,393,599 B2 * 7/2008 Thompson .......... C07F 15/0033
257/40
2004/0253478 A1 12/2004 Thompson et al.
(Continued)

FOREIGN PATENT DOCUMENTS

CN 102484214 5/2012
EP 2471889 7/2012
(Continued)

OTHER PUBLICATIONS

Tamayo et al, "Synthesis and Characterization of Facial and Meridional Tris-Cyclometalated Iridium (III) Complexes", J. Am. Chem. Soc., May 22, 2003, pp. 7377-7387, vol. 125, No. 24.
(Continued)

*Primary Examiner* — Jose R Diaz
(74) *Attorney, Agent, or Firm* — Ohlandt, Greeley, Ruggiero & Perle, L.L.P.

(57) ABSTRACT

A novel iridium complex which can be applied in an organic electroluminescent light emitting device, an organic electrochemical light emitting device, or the like, and which is thermally stable and has excellent sublimabilities. An iridium complex characterized by being represented by
(Continued)

General Formula (1) (in General Formula (1), $R^1$ to $R^{11}$ and $R^{13}$, $R^{14}$, and $R^{18}$ represent a hydrogen atom, an alkyl group with 1 to 30 carbon atoms, an aryl group with 6 to 30 carbon atoms, a halogen atom, or a cyano group; $R^{12}$, $R^{15}$ to $R^{17}$ and $R^{19}$ represent a hydrogen atom, an alkyl group with 1 to 30 carbon atoms, a halogen atom, or a cyano group; the alkyl group may be substituted with an aryl group, a halogen atom, or a cyano group; the aryl group may be substituted with an alkyl group, a halogen atom, or a cyano group; adjacent $R^{12}$ to $R^{19}$ may bind to each other to form a condensed ring; and m is an integer of 1 or 2, n is an integer of 1 or 2, and m+n is 3).

12 Claims, 4 Drawing Sheets

(51) Int. Cl.
  *C09K 11/06* (2006.01)
  *H01L 51/50* (2006.01)
  *H05B 33/14* (2006.01)

(52) U.S. Cl.
  CPC .......... *H01L 51/50* (2013.01); *H01L 51/5016* (2013.01); *H05B 33/14* (2013.01); *C09K 2211/185* (2013.01)

(56) References Cited

U.S. PATENT DOCUMENTS

| | | |
|---|---|---|
| 2009/0039776 A1 | 2/2009 | Yamada et al. |
| 2011/0204339 A1 | 8/2011 | Dobbs et al. |
| 2011/0266524 A1 | 11/2011 | Lecloux et al. |
| 2012/0208999 A1 | 8/2012 | Konno |

FOREIGN PATENT DOCUMENTS

| | | |
|---|---|---|
| JP | 2004189673 A | 7/2004 |
| JP | 200940728 A | 2/2009 |
| JP | 2009108041 A | 5/2009 |
| JP | 2014101307 A | 6/2014 |
| KR | 10-1314034 | 10/2013 |
| WO | 2010028151 A1 | 3/2010 |
| WO | 2010056669 A1 | 5/2010 |
| WO | 2010111755 A2 | 10/2010 |
| WO | 2011024737 A1 | 3/2011 |
| WO | 2012158851 A1 | 11/2012 |
| WO | 2012166608 A1 | 12/2012 |
| WO | 2012172482 A1 | 12/2012 |

OTHER PUBLICATIONS

International Search Report dated Jun. 14, 2016 from corresponding International Application No. PCT/JP2016/057088, 1 page.
International Preliminary Report on Patentability dated Sep. 21, 2017 from corresponding International PCT Application PCT/JP2016/057088, 6 pages.
Korean Office Action dated Jan. 15, 2019 in corresponding Korean Patent Application No. 10-2017-7022821, 16 pages.
Chinese Office Action dated Feb. 19, 2019 in corresponding Chinese Patent Application No. 201680014587.9, 18 pages.

* cited by examiner

[FIG. 1]
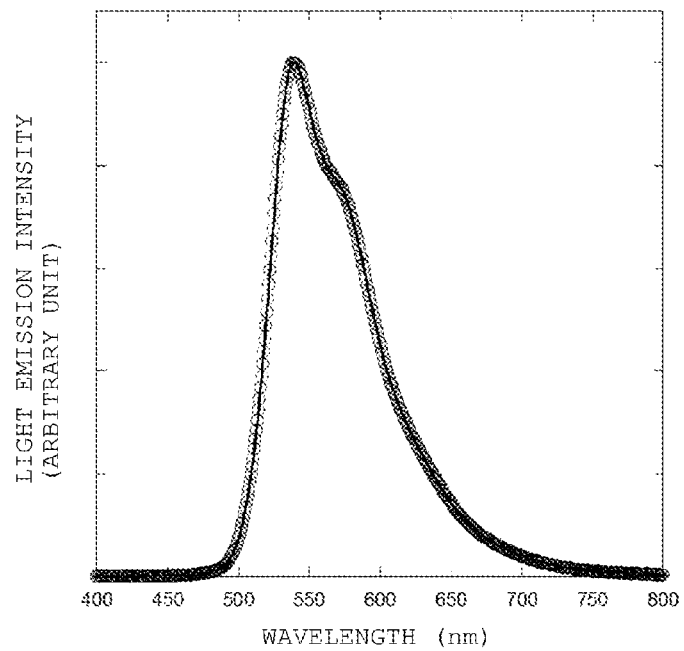
[FIG. 2]
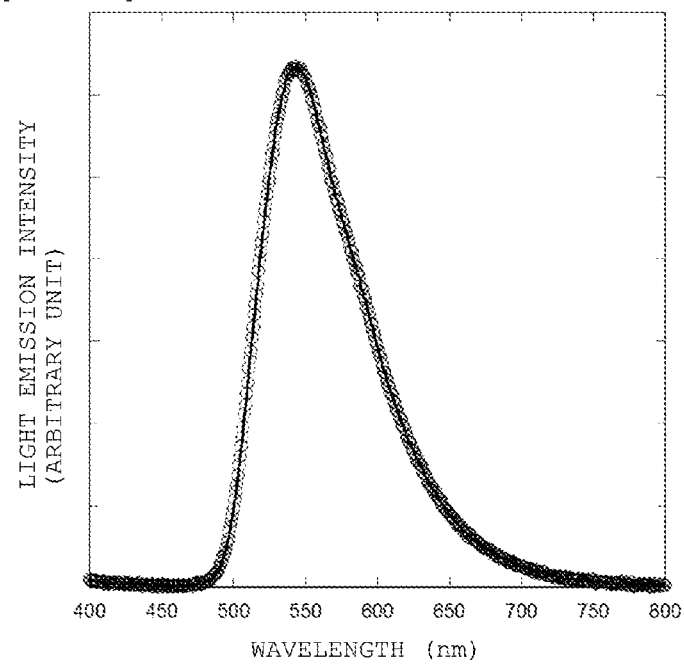

[FIG. 3]
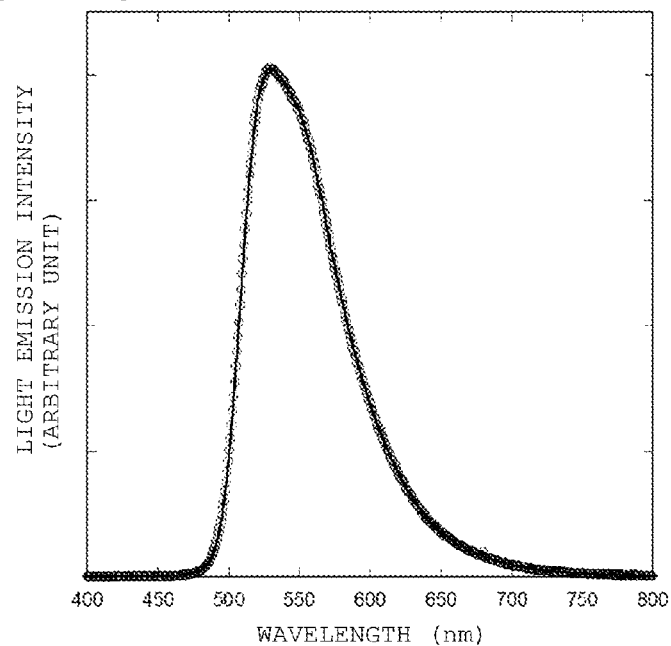
[FIG. 4]
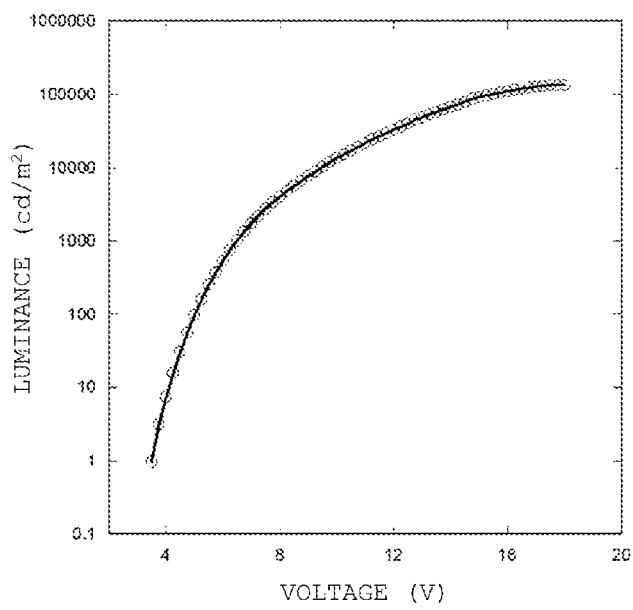

[FIG. 5]
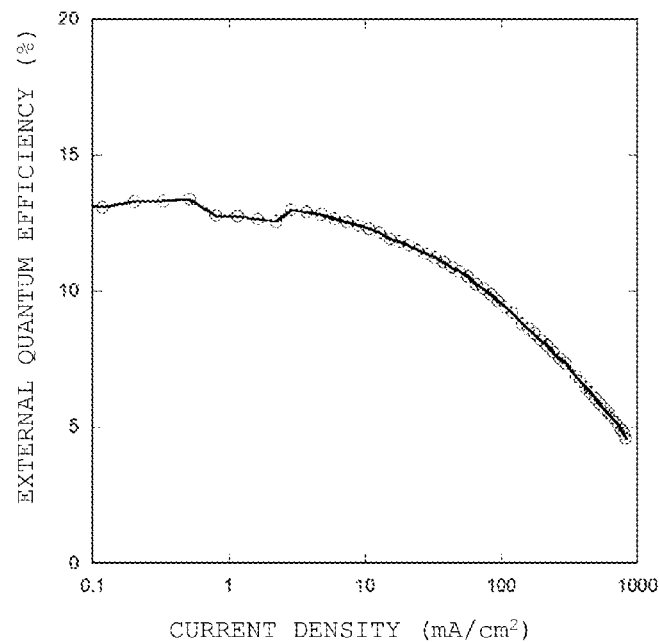
[FIG. 6]
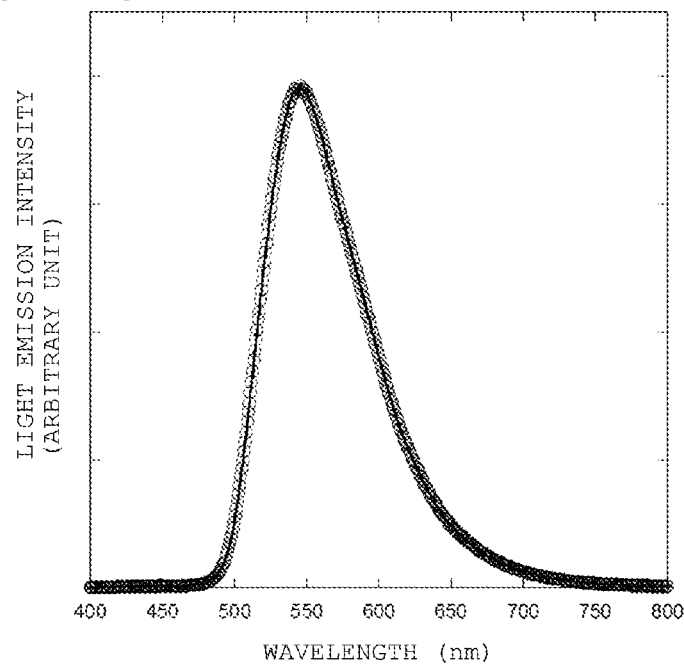

[FIG. 7]
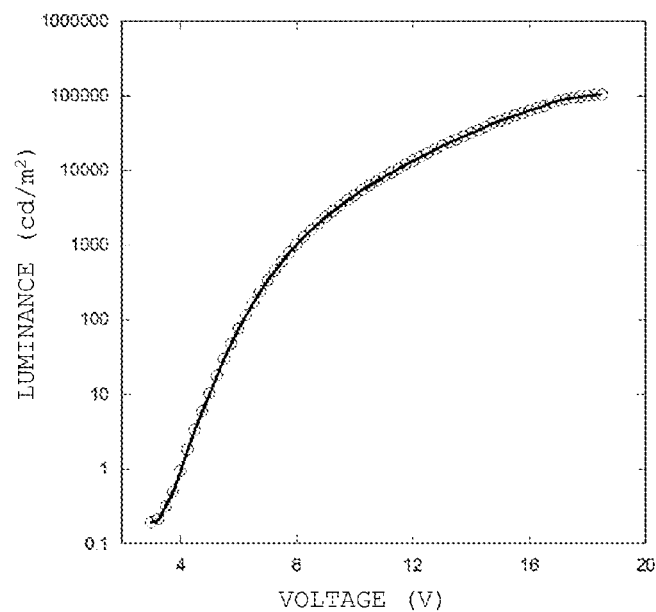
[FIG. 8]
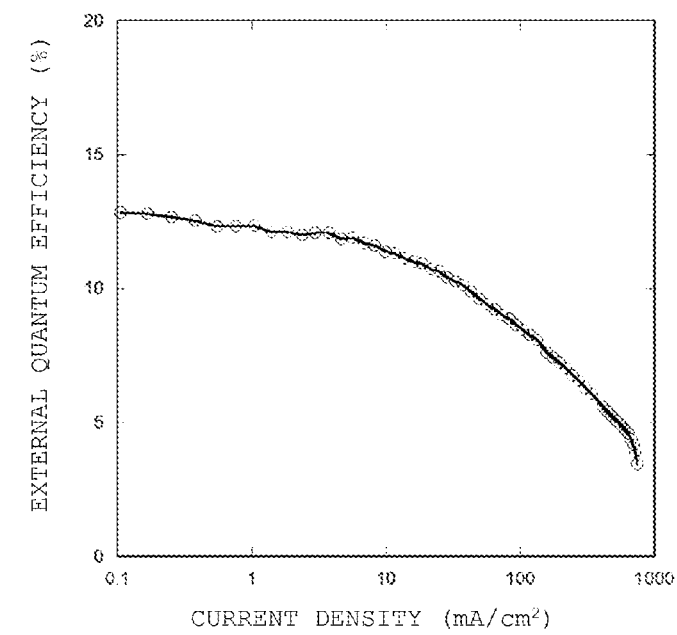

HETEROLEPTIC IRIDIUM COMPLEX, AND LIGHT-EMITTING MATERIAL AND ORGANIC LIGHT-EMITTING ELEMENT USING COMPOUND

TECHNICAL FIELD

The present disclosure relates to a novel iridium complex that is useful as a light emitting material of an organic light emitting device (organic electroluminescent light emitting device, organic electrochemical light emitting device, or the like), and also to an organic light emitting device using the compound.

BACKGROUND ART

In recent years, organic light emitting devices represented by an organic electroluminescent light emitting device are attracting attention as display or lighting technique, and studies for the practical use thereof are actively under way. In particular, enhancing the light emission efficiency is an important study subject, and currently, phosphorescent materials which use light emission from excited triplet state are attracting attention as a light emitting material.

When light emission from excited singlet state is used, the probability of generation of the light emitting excitons is believed to be 25% since the singlet excitons and triplet excitons are generated at a ratio of 1:3. Furthermore, since the light extraction efficiency is approximately 20%, limit of the external extraction quantum efficiency is believed to be 5%. On the other hand, if an excited triplet state is also used, the upper limit of internal quantum efficiency is 100%, and thus, in principle, the light emission efficiency becomes 4 times larger than that in the case of an excited singlet state. Under this background, intensive studies for development of a phosphorescent material for organic light emitting device are actively under progress. For example, as a phosphorescent material, an iridium complex which has a 2-phenylpyrimidine ligand is disclosed (see, Patent Literature 1, for example). Furthermore, a 2-phenylpyrimidine based iridium complex which has excellent solubility and is suitable for coating process is disclosed (see, Patent Literature 2, for example).

PRIOR ART DOCUMENTS

Patent Literature

Patent Literature 1: JP 2009-40728 A
Patent Literature 2: WO 2011/024737 A
Patent Literature 3: WO 2012/172482 A
Patent Literature 4: JP 2004-189673 A
Patent Literature 5: JP 2009-108041 A
Patent Literature 6: JP 2014-101307 A
Patent Literature 7: WO 2012/166608 A
Patent Literature 8: WO 2010/056669 A
Patent Literature 9: WO 2010/111755 A
Patent Literature 10: WO 2012/158851 A
Patent Literature 11: WO 2010/028151 A

Non Patent Literature

Non Patent Literature 1: Tamayo A. B. J. Am. Chem. Soc., 2003, 125, 7377

SUMMARY OF INVENTION

Problems to be Solved by the Invention

Furthermore, on the other hand, as for the phosphorescent material suitable for vacuum vapor deposition process, those generally having excellent thermal stability and, in particular, a favorable sublimability are preferable. That is because, when a phosphorescent material has an excellent sublimability, it becomes possible to further enhance the compound purity by sublimation purification and also an organic light emitting device can be stably produced by using vacuum vapor deposition. To achieve practical application of an organic light emitting device, it is strongly desired to develop in future a phosphorescent material which has excellent thermal stability and sublimability.

An object of the present disclosure is to provide a novel iridium complex which can be applied in an organic electroluminescent light emitting device, an organic electrochemical light emitting device, or the like, and which is thermally stable and has an excellent sublimability.

Means to Solve a Problem

As a result of intensive studies in consideration of the circumstances that are described above, the inventors of the present invention have found that an iridium complex represented by General Formula (1) exhibits strong light emission in the visible light range at room temperature, is thermally stable, and has an excellent sublimability. In addition, the inventors actually showed that an organic light emitting device exhibiting high light emission efficiency can be produced by using the iridium complex of the present invention, and the present invention is completed accordingly.

Namely, according to the present application, the following inventions are provided.

An iridium complex according to the present invention is represented by the following General Formula (1);

[Chem. 1]

General Formula (1)

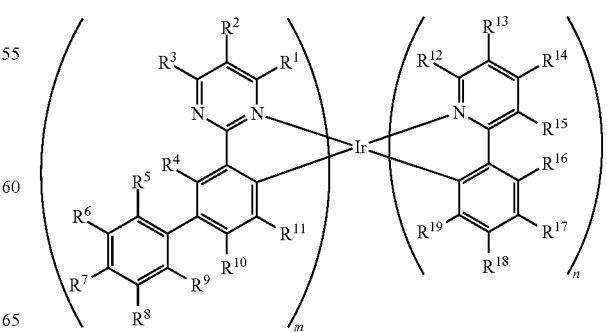

(in General Formula (1), N represents a nitrogen atom and Ir represents an iridium atom; $R^1$ to $R^{11}$, $R^{13}$, $R^{14}$, and $R^{18}$ each independently represent a hydrogen atom, an alkyl group with 1 to 30 carbon atoms, an aryl group with 6 to 30 carbon atoms, a halogen atom, or a cyano group; $R^{12}$, $R^{15}$ to $R^{17}$ and $R^{19}$ each independently represent a hydrogen atom, an alkyl group with 1 to 30 carbon atoms, a halogen atom, or a cyano group; the alkyl group may be substituted with an aryl group, a halogen atom, or a cyano group; the aryl group may be substituted with an alkyl group, a halogen atom, or a cyano group; adjacent $R^{12}$ to $R^{19}$ may bind to each other to form a condensed ring; and m is an integer of 1 or 2, n is an integer of 1 or 2, and m+n is 3).

In the iridium complex according to present invention, $R^{12}$ to $R^{19}$ are preferably a hydrogen atom or an alkyl group with 1 to 30 carbon atoms.

In the iridium complex according to present invention, $R^{13}$ is preferably an aryl group with 6 to 30 carbon atoms.

In the iridium complex according to present invention, $R^{14}$ is preferably an aryl group with 6 to 30 carbon atoms.

In the iridium complex according to present invention, $R^{18}$ is preferably an aryl group with 6 to 30 carbon atoms.

In the iridium complex according to present invention, $R^{15}$ and $R^{16}$ preferably bind to each other to form a condensed ring.

In the iridium complex according to present invention, $R^{12}$ and $R^{13}$ preferably bind to each other to form a condensed ring.

In the iridium complex according to present invention, at least one of $R^{12}$ to $R^{19}$ is preferably a halogen atom.

In the iridium complex according to present invention, all of $R^4$, $R^5$, $R^9$, and $R^{10}$ are preferably a hydrogen atom.

In the iridium complex according to present invention, m is preferably 2 and n is preferably 1.

In the iridium complex according to present invention, m is preferably 1 and n is preferably 2.

The iridium complex according to present invention is preferably a facial isomer.

A light emitting material according to present invention includes the iridium complex according to present invention.

An organic light emitting device according to present invention includes the light emitting material according to present invention.

Effects of the Invention

According to the present disclosure, it is possible to provide a novel iridium complex which can be applied in an organic electroluminescent light emitting device, an organic electrochemical light emitting device, or the like, and which is thermally stable and has an excellent sublimability.

From the viewpoint that the novel iridium complex of the present disclosure exhibits strong light emission in the visible light range at room temperature and has excellent thermal stability and sublimability, it can be suitably used as a light emitting device material for various applications. Furthermore, from the viewpoint that the organic light emitting device using this compound exhibits high luminance light emission in the visible light range, it is very suitable in the field of display device, display, backlight, and light source for lighting, or the like.

BRIEF DESCRIPTION OF DRAWINGS

FIG. 1 is a light emission spectrum of the compound (K-51) of the present invention, which is a facial isomer, in THF under argon atmosphere.

FIG. 2 is a light emission spectrum of a co-vapor deposited film of the compound (K-123) of the present invention, which is a facial isomer, and CBP (5:95 (mass % ratio)).

FIG. 3 is an EL spectrum of an organic electroluminescent light emitting device produced by using the compound (K-3) of the present invention, which is a facial isomer.

FIG. 4 is a drawing illustrating voltage-luminance of an organic electroluminescent light emitting device produced by using the compound (K-3) of the present invention, which is a facial isomer.

FIG. 5 is a drawing illustrating current density-external quantum efficiency of an organic electroluminescent light emitting device produced by using the compound (K-3) of the present invention, which is a facial isomer.

FIG. 6 is an EL spectrum of an organic electroluminescent light emitting device produced by using the compound (K-123) of the present invention, which is a facial isomer.

FIG. 7 is a drawing illustrating voltage-luminance of an organic electroluminescent light emitting device produced by using the compound (K-123) of the present invention, which is a facial isomer.

FIG. 8 is a drawing illustrating current density-external quantum efficiency of an organic electroluminescent light emitting device produced by using the compound (K-123) of the present invention, which is a facial isomer.

MODE FOR CARRYING OUT THE INVENTION

Next, the present invention is explained in detail by describing embodiments, but the present invention should not be interpreted so as to be limited to those descriptions. As long as the effect of the present invention can be obtained, the embodiments can have various modifications.

In the explanations of General Formulae of the present invention, the hydrogen atom also include an isotope (i.e., deuterium or the like), and the atoms further constituting a substituent group also include an isotope thereof.

The iridium complex according to the present invention is represented by General Formula (1), and by containing the iridium complex in a light emitting layer or plural organic compound layers including a light emitting layer of an organic light emitting device by vacuum vapor deposition method or the like, an organic light emitting device which exhibits excellent light emission in the visible light range is obtained.

Hereinbelow, the present invention is explained in greater detail.

The iridium complex according to the present invention represented by General Formula (1) is specifically a heteroleptic iridium complex which has a specific structure having a 2-phenylpyrimidine derivative ligand represented by General Formula (2) and a 2-phenylpyridine derivative ligand represented by General Formula (3).

[Chem. 2]

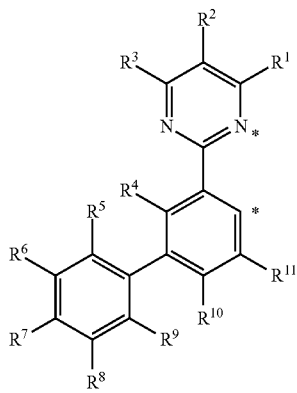

General Formula (2)

[Chem. 3]

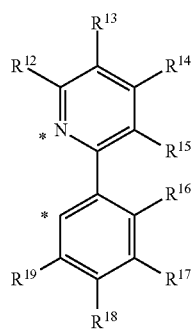

General Formula (3)

$R^1$ to $R^{19}$ in General Formulae (2) and (3) have the same meaning as $R^1$ to $R^{19}$ in General Formula (1), and a preferred range thereof is also the same. * represents a site for binding to iridium.

Until now, a 2-phenylpyrimidine-based homoleptic iridium complex which is represented by General Formula (4) is known conventionally; however, according to the knowledge of the inventors of the present invention, this iridium complex has an insufficient sublimability, and as decomposition is accompanied during vacuum vapor deposition process, improving the sublimability remained as a significant problem.

[Chem. 4]

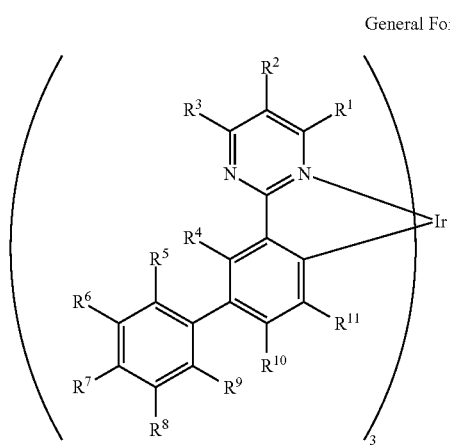

General Formula (4)

(in General Formula (4), N represents a nitrogen atom and Ir represents an iridium atom; and $R^1$ to $R^{11}$ have the same meaning as $R^1$ to $R^{11}$ in General Formula (1), and a preferred range thereof is also the same).

Based on the technical background described above, the inventors of the present invention intensively tried to develop a phosphorescent material which has excellent thermal stability and sublimability, and as a result, they have found that a heteroleptic iridium complex with novel structure which is represented by General Formula (1) exhibits very strong light emission in the visible light range at room temperature, and has particularly excellent thermal stability and sublimability compared to a conventionally known homoleptic iridium complex which is represented by General Formula (4). In addition, the inventors actually showed that the iridium complex represented by General Formula (1) can be suitably used as a phosphorescent material of an organic electroluminescent light emitting device, and they devised the present invention accordingly.

The homoleptic iridium complex which is represented by General Formula (4) is characterized in that it has three identical cyclometallated ligands; however, there are problems that, due to high symmetry, crystallinity is high in solid state, and as a result, the energy for linking the complexes is high so that the sublimation temperature becomes high. On the other hand, it is contemplated by the inventors of the present invention that the compound of the present invention which is represented by General Formula (1) is a heteroleptic iridium complex which has a cyclometallated ligand of different type (i.e., ligands represented by General Formula (2) and General Formula (3)), and as it has low crystallinity in solid state due to low symmetry, it has low energy for linking the complexes so that a favorable sublimability is yielded.

Furthermore, as an intrinsic characteristic of a 2-phenylpyrimidine based ligand, two nitrogen atoms are present in the pyrimidine ring, and therefore there are plural sites for binding to iridium as a center metal. According to the knowledge of the inventors of the present invention, there can be a case in which yield of a desired iridium complex is lowered due to generation of multi nucleus complex (dimer or the like) which is caused by the presence of those plural sites. Accordingly, the present invention is also characterized in that, by using a 2-phenylpyrimidine based ligand with specific structure that is represented by General Formula (2), binding to iridium at $R^4$ site is prevented due to the steric effect of the adjacent phenyl group so that generation of a multi nucleus complex is inhibited.

Among the iridium complexes according to the present invention that are represented by General Formula (1), those having light emission quantum yield of 0.1 or higher in solution or thin film state at room temperature are preferable, those having light emission quantum yield of 0.4 or higher are more preferable, and those having light emission quantum yield of 0.6 or higher are particularly preferable.

Measurement of light emission quantum yield in solution can be carried out after the solution in which the iridium complex has been dissolved is purged with an argon or nitrogen gas, or after the solution in which the light emitting material has been dissolved is deaerated as it is frozen, for removal of dissolved oxygen. Either an absolute or relative method may be used for measuring method of the light emission quantum yield. In the relative method, the light emission quantum yield can be measured in comparison with the light emission spectrum of a standard substance (e.g., quinine sulfate). In the absolute method, the light emission quantum yield in solid state or in solution can be measured by using a commercially available instrument (For example, Absolute PL Quantum Yield Spectrometer (C9920-02), manufactured by Hamamatsu Photonics K. K.). The light emission quantum yield in solution can be measured by using various solvents, but the iridium complex according to the present invention preferably satisfies the above light emission quantum yield in any solvent.

Measurement of light emission quantum yield in thin film state can be carried out by, for example, vacuum vapor-depositing the iridium complex of the present invention on quartz glass, and performing the measurement by using a commercially available instrument (For example, Absolute PL Quantum Yield Spectrometer (C9920), manufactured by Hamamatsu Photonics K. K.). The light emission quantum yield in thin film can be measured by vapor deposition of the iridium complex of the present invention only or by co-vapor deposition with various host materials; however, it is desirable that the above light emission quantum yield is satisfied by the iridium complex of the present invention at any condition.

The iridium complex according to the present invention exhibits light emission mainly in the visible light range (in particular, green to red color range); however, the wavelength range depends on the type or structure of a ligand. In particular, with regard to the maximum light emission wavelength of a light emission spectrum in solution or thin film at room temperature, it is preferably in the range of 300 nm to 900 nm, more preferably in the range of 400 nm to 800 nm, particularly preferably in the range of 400 nm to 600 nm, and more particularly preferably in the range of 500 nm to 600 nm.

The iridium complex according to the present invention is an octahedral hexadentate complex, and as a geometric isomer, a facial isomer and a meridional isomer are present. There is actually a case in which a mixture of a facial isomer and a meridional isomer is obtained at the time of synthesizing the iridium complex according to the present invention. Those geometric isomers can be separated by column chromatography or sublimation purification, for example. The iridium complex represented by General Formulae (5) and (6), or the iridium complex represented by General Formulae (7) and (8) respectively have a geometric isomer relationship. Furthermore, the iridium complex represented by General Formulae (5) and (7) corresponds to a facial isomer, and the iridium complex represented by General Formulae (6) and (8) corresponds to a meridional isomer.

[Chem. 5]

General Formula (5)

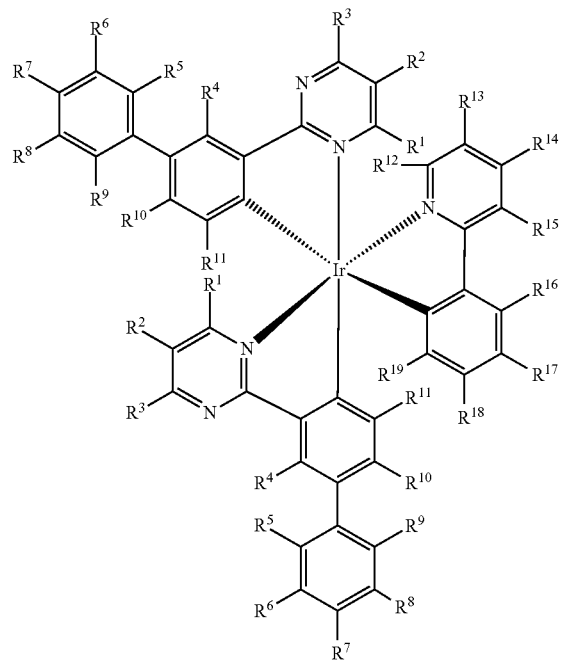

[Chem. 6]

General Formula (6)

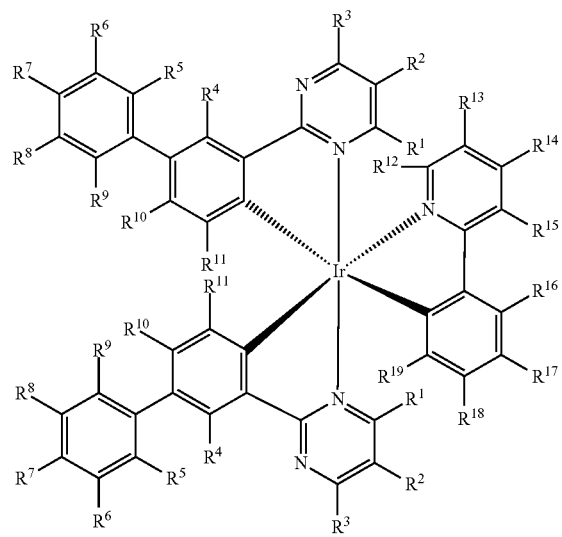

-continued

[Chem. 7]

General Formula (7)

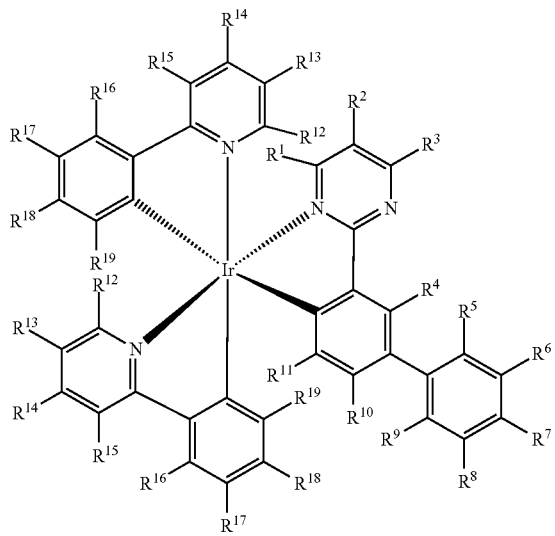

[Chem. 8]

General Formula (8)

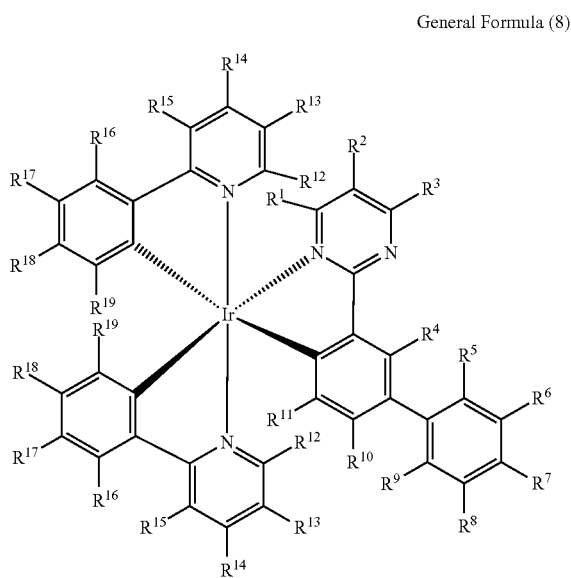

(in General Formulae (5) to (8), N represents a nitrogen atom and Ir represents an iridium atom; and $R^1$ to $R^{19}$ have the same meaning as $R^1$ to $R^{19}$ in General Formula (1), and a preferred range thereof is also the same).

Until now, there have been various reports regarding the light emission characteristics of a facial isomer and a meridional isomer of the cyclometallated iridium complex; however, while a case in which the facial isomer has higher light emission quantum yield is known (for example, Tamayo A. B. J. Am. Chem. Soc., 2003, 125, 7377 (Non Patent Literature 1)), a case in which the meridional isomer has higher light emission quantum yield is also known (for example, WO 2012/172482 A (Patent Literature 3)).

As a result of detailed determination of light emission characteristics about the geometric isomer of the iridium complex of the present invention which is represented by General Formula (1), the inventors of the present invention found that the facial isomer has significantly higher light emission quantum yield when compared to the meridional isomer (see, Examples).

As such, the iridium complex of the present invention which is represented by General Formula (1) is preferably a facial isomer. The iridium complex according to the present invention preferably contains 50% or more of the facial isomer, more preferably contains 80% or more of the facial isomer, particularly preferably contains 90% or more of the facial isomer, and more particularly preferably contains 99% or more of the facial isomer. Furthermore, the facial isomer or meridional isomer can be identified by NMR, mass analysis, or X ray crystal structure analysis, or the like. Furthermore, the content of the isomer can be quantified by NMR or HPLC.

The meridional isomer of the iridium complex of the present invention which is represented by General Formula (1) can be isomerized into a facial isomer. In particular, photoisomerization as shown in Formulae (A) and (B) is preferable.

[Chem. 9]

Formula (A)

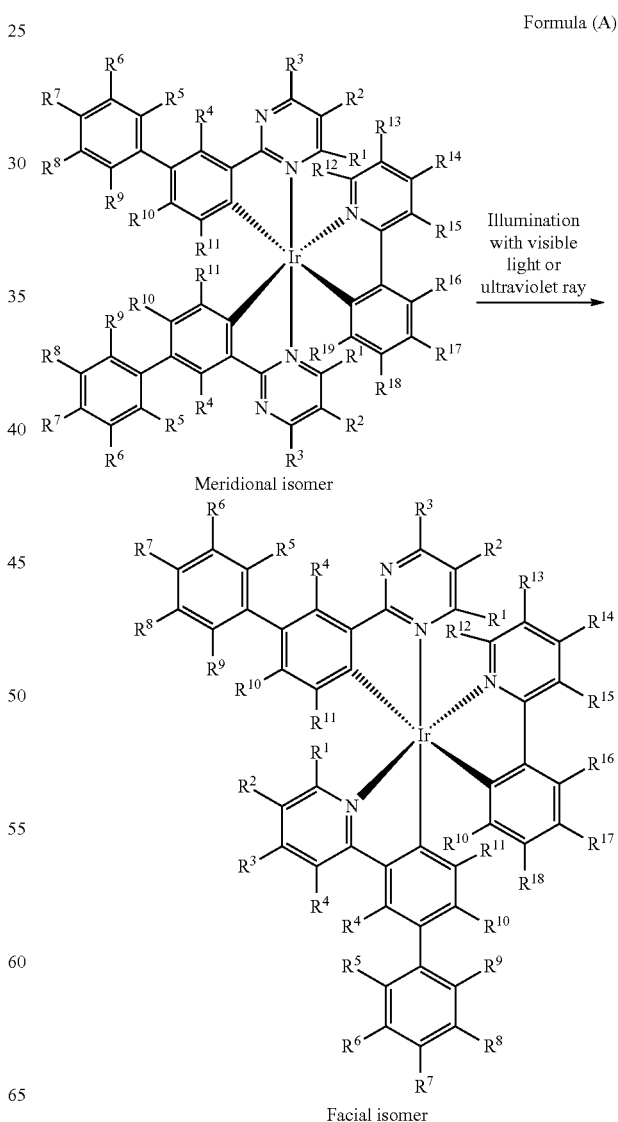

-continued

[Chem. 10]

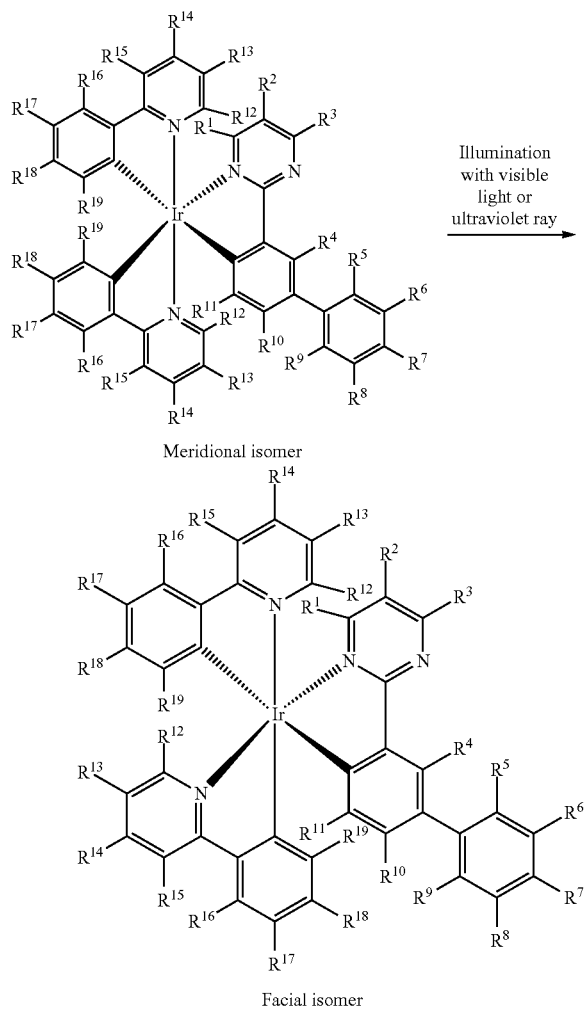

Formula (B)

Illumination with visible light or ultraviolet ray

Meridional isomer

Facial isomer (in General Formulae (A) and (B), N represents a nitrogen atom and Ir represents an iridium atom; and $R^1$ to $R^{19}$ have the same meaning as $R^1$ to $R^{19}$ in General Formula (1), and a preferred range thereof is also the same).

The photoisomerization reaction of a meridional isomer can be carried out by referencing JP 2004-189673 A (Patent Literature 4), JP 2009-108041 A (Patent Literature 5), JP 2014-101307 A (Patent Literature 6), or the like.

The photoisomerization reaction of a meridional isomer is explained in greater detail. The photoisomerization reaction is characterized in that a meridional isomer or a solution containing meridional isomer is illuminated with light, and isomerization to facial isomer is achieved.

As the method for illumination with light, it is sufficient that the light hits a meridional isomer, and method therefor is out of question. It is also acceptable that illumination with light is carried out for a reaction solution which contains a mixture of a meridional isomer and a facial isomer.

The photoisomerization reaction of a meridional isomer is preferably carried out in a solution. As for the solvent, a solvent which is capable of dissolving a meridional isomer is preferable, and a solvent which does not react with a raw material and a product is used. Specific examples of the solvent include various organic solvents like saturated aliphatic hydrocarbons such as n-pentane, n-hexane, n-heptane, or tridecane, halogenated aliphatic hydrocarbons such as dichloromethane, chloroform, or dichloroethane, ketones such as acetone or methyl ethyl ketone, amides such as N,N-dimethyl formamide or N-methyl pyrrolidone, esters such as ethyl acetate or butyl acetate, aromatic hydrocarbons such as benzene or toluene, halogenated aromatic hydrocarbons such as chlorobenzene or dichlorobenzene, nitrogen-containing aromatic compounds such as pyridine or picoline, ethers such as tetrahydrofuran (THF), dioxane, or diethyl ether, nitriles such as acetonitrile, propionitrile, or benzonitrile, alcohols such as methanol, ethanol, propanol, butanol, or ethylene glycol, and dimethyl sulfoxide. Among them, halogenated aliphatic hydrocarbons, ethers, or dimethyl sulfoxide are preferable. Specific examples of a preferred solvent include dichloromethane, chloroform, tetrahydrofuran, or dimethyl sulfoxide, more preferably include dichloromethane, tetrahydrofuran, or dimethyl sulfoxide, and particularly preferably include tetrahydrofuran.

The photoisomerization reaction of a meridional isomer is not particularly limited in terms of concentration as long as illumination with light is carried out homogeneously; however, it is generally carried out at concentration of 1 mol/L or less, or preferably at concentration of 0.01 mol/L or less. The lower limit of the concentration is, although not particularly limited, preferably 0.0001 mol/L or more.

The reaction vessel which is used for carrying out the illumination with light can be any vessel as long as it allows the illumination with light; however, particularly preferred are a glass vessel, for example, Pyrex (registered trademark) reaction vessel, or a quartz reaction vessel which has high UV permeability.

As for the condition for the illumination with light, the temperature condition is not particularly limited, but is generally between the solidification point of a solvent to be used and boiling point of the solvent, preferably between −75° C. and the boiling point of the solvent, and more preferably between −5° C. and 50° C.

The illumination with light and post treatment after the illumination with light can be carried out under atmospheric pressure, in an inert gas atmosphere like nitrogen or argon, or in a reduced pressure or vacuum state; however, the illumination with light is more preferably carried out in an inert gas atmosphere like nitrogen or argon.

The pressures condition is not particularly limited, however, the reaction is generally carried out under normal pressure.

The wavelength of light which is used for the illumination with light can be a wavelength at which the meridional isomer can be absorbed, and light in ultraviolet ray to visible light range is preferable. Specifically, light with a wavelength of 200 to 800 nm is preferable, light with a wavelength of 200 to 600 nm is more preferable, light with a wavelength of 300 to 500 nm is particularly preferable, and light with a wavelength of 300 to 450 nm is more particularly preferable.

As for the method for illumination with light, reference can be made to the method described in "Photochemistry I" (author: Haruo INOUE, et. al., Publisher: Maruzen), for example, and any of an external illumination method by which illumination is made from the outside of a reaction vessel or an internal illumination method by which illumination is made from the inside of a reaction vessel can be employed.

As for the time for illumination with light which is required for the reaction, it greatly depends on the type of an iridium complex or reaction conditions, and thus, it can be set at suitable time while following the reaction by using a method like an absorption spectrum, a light emission spectrum, HPLC, or mass analysis. Specifically, the time is preferably 1 minute to 5 days, more preferably 1 minute to 72 hours, particularly preferably 1 hour to 48 hours, and more particularly preferably 1 hour to 24 hours.

Type of a lamp which is used for illumination with light is not particularly limited, and examples thereof include a high pressure mercury lamp, a low pressure mercury lamp, a ultrahigh pressure mercury lamp, a halogen lamp, a xenon lamp, laser, sun light, an incandescent lamp, a deuterium lamp, or a UV lamp.

Symbols that are described in General Formula (1) (i.e., m, n, and $R^1$ to $R^{19}$) are explained hereinbelow.

In General Formula (1), m is an integer of 1 or 2, n is an integer of 1 or 2, and m+n is 3. Namely, when m is 1, n is 2, and when m is 2, n is 1.

$R^1$ to $R^{11}$, $R^{13}$, $R^{14}$, and $R^{18}$ each independently represent a hydrogen atom, an alkyl group with 1 to 30 carbon atoms, an aryl group with 6 to 30 carbon atoms, a halogen atom, or a cyano group.

$R^{12}$, $R^{15}$ to $R^{17}$ and $R^{19}$ each independently represent a hydrogen atom, an alkyl group with 1 to 30 carbon atoms, a halogen atom, or a cyano group.

Furthermore, adjacent $R^{12}$ to $R^{19}$ may bind to each other to form a condensed ring.

The alkyl group with 1 to 30 carbon atoms preferably has 1 to 20 carbon atoms, more preferably has 1 to 15 carbon atoms, particularly preferably has 1 to 10 carbon atoms, and more particularly preferably has 1 to 6 carbon atoms.

The alkyl group with 1 to 30 carbons preferably include a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a neopentyl group, a 1-methylpentyl group, a 1-pentylhexyl group, a 1-butylpentyl group, a 1-heptyloctyl group, a cyclohexyl group, a cyclooctyl group, or a 3,5-tetramethylcyclohexyl group. More preferably, it is a methyl group, an ethyl group, a propyl group, an isopropyl group, a n-butyl group, a s-butyl group, an isobutyl group, a t-butyl group, a n-pentyl group, a neopentyl group, or a 1-methylpentyl group. Particularly preferably, it is a methyl group. The alkyl group may be additionally substituted with an aryl group, a halogen atom, or a cyano group, and the alkyl group substituted with fluorine is preferable from the viewpoint that the sublimability of iridium complex is enhanced.

The aryl group with 6 to 30 carbon atoms preferably has 6 to 20 carbon atoms, more preferably has 6 to 15 carbon atoms, and particularly preferably has 6 to 12 carbon atoms.

The aryl group with 6 to 30 carbons preferably include a phenyl group, a biphenyl-2-yl group, a biphenyl-3-yl group, a biphenyl-4-yl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, a m-tolyl group, a p-tolyl group, a p-t-butylphenyl group, a p-(2-phenylpropyl)phenyl group, a 4'-methylbiphenylyl group, a 4"-t-butyl-p-terphenyl-4-yl group, an o-cumenyl group, a m-cumenyl group, a p-cumenyl group, a 2,3-xylyl group, a 2,4-xylyl group, a 2,5-xylyl group, a 2,6-xylyl group, a 3,4-xylyl group, a 3,5-xylyl group, a mesityl group, a m-quaterphenyl group, a 1-naphthyl group, or a 2-naphthyl group. More preferably, it is a phenyl group, an o-tolyl group, a m-tolyl group, a p-tolyl group, a 2,3-xylyl group, a 2,4-xylyl group, a 2,5-xylyl group, a 2,6-xylyl group, a 3,4-xylyl group, a 3,5-xylyl group, or a mesityl group. Particularly preferably, it is a phenyl group. The aryl group may be additionally substituted with an alkyl group, a halogen atom, or a cyano group, and a phenyl group substituted with an alkyl group is particularly preferable from the viewpoint that the sublimability of iridium complex is enhanced.

The halogen atom is preferably a chlorine atom, a bromine atom, or a fluorine atom. More preferably, it is a bromine atom or a fluorine atom. Particularly preferably, it is a fluorine atom.

$R^1$ to $R^{19}$ are explained more specifically hereinbelow.

As for $R^1$, a hydrogen atom and an alkyl group with 1 to 30 carbon atoms are more preferable among those described above, a methyl group or a hydrogen atom is particularly preferable, and a hydrogen atom is more particularly preferable. The preferred range of those substituent groups are as described in the above. Namely, the alkyl group with 1 to 30 carbon atoms preferably has 1 to 20 carbon atoms, more preferably has 1 to 15 carbon atoms, particularly preferably has 1 to 10 carbon atoms, and more particularly preferably has 1 to 6 carbon atoms.

As for $R^2$, a hydrogen atom, an alkyl group with 1 to 30 carbon atoms, or an aryl group with 6 to 30 carbon atoms is more preferable among those described above, a hydrogen atom or an alkyl group with 1 to 30 carbon atoms is particularly preferable, a hydrogen atom, a methyl group, or an ethyl group is more particularly preferable, and a methyl group or an ethyl group is most preferable. The preferred range of those substituent groups are as described in the above. Namely, the alkyl group with 1 to 30 carbon atoms preferably has 1 to 20 carbon atoms, more preferably has 1 to 15 carbon atoms, particularly preferably has 1 to 10 carbon atoms, and more particularly preferably has 1 to 6 carbon atoms. Furthermore, the aryl group with 6 to 30 carbon atoms preferably has 6 to 20 carbon atoms, more preferably has 6 to 15 carbon atoms, and particularly preferably has 6 to 12 carbon atoms.

As for $R^3$, a hydrogen atom, an alkyl group with 1 to 30 carbon atoms, or an aryl group with 6 to 30 carbon atoms is more preferable among those described above, a hydrogen atom or an alkyl group with 1 to 30 carbon atoms is particularly preferable, and a hydrogen atom is more particularly preferable. The preferred range of those substituent groups are as described in the above. Namely, the alkyl group with 1 to 30 carbon atoms preferably has 1 to 20 carbon atoms, more preferably has 1 to 15 carbon atoms, particularly preferably has 1 to 10 carbon atoms, and more particularly preferably has 1 to 6 carbon atoms. Furthermore, the aryl group with 6 to 30 carbon atoms preferably has 6 to 20 carbon atoms, more preferably has 6 to 15 carbon atoms, and particularly preferably has 6 to 12 carbon atoms.

As for $R^4$, $R^5$, $R^9$, $R^{10}$ or $R^{11}$, a hydrogen atom and an alkyl group with 1 to 30 carbon atoms are more preferable among those described above, a methyl group or a hydrogen atom is particularly preferable, and a hydrogen atom is more particularly preferable. It is most preferable that $R^4$, $R^5$, $R^9$, and $R^{10}$ are all a hydrogen atom. The preferred range of those substituent groups are as described in the above. Namely, the alkyl group with 1 to 30 carbon atoms preferably has 1 to 20 carbon atoms, more preferably has 1 to 15 carbon atoms, particularly preferably has 1 to 10 carbon atoms, and more particularly preferably has 1 to 6 carbon atoms. Forming a ring structure (i.e., saturated ring or unsaturated ring) as $R^4$ and $R^5$ or $R^9$ and $R^{10}$ bind to each other is not preferable from the viewpoint of synthesis.

As for $R^6$ to $R^8$, a hydrogen atom, an alkyl group with 1 to 30 carbon atoms, or an aryl group with 6 to 30 carbon atoms is more preferable among those described above, a hydrogen atom or an alkyl group with 1 to 30 carbon atoms is particularly preferable, a hydrogen atom or a methyl group is more particularly preferable. The preferred range of those substituent groups are as described in the above. Namely, the alkyl group with 1 to 30 carbon atoms preferably has 1 to 20 carbon atoms, more preferably has 1 to 15 carbon atoms, particularly preferably has 1 to 10 carbon atoms, and more particularly preferably has 1 to 6 carbon atoms. Furthermore, the aryl group with 6 to 30 carbon atoms preferably has 6 to 20 carbon atoms, more preferably has 6 to 15 carbon atoms, and particularly preferably has 6 to 12 carbon atoms.

As for $R^{12}$, $R^{15}$, $R^{16}$, $R^{17}$ or $R^{19}$, a hydrogen atom or an alkyl group with 1 to 30 carbon atoms is more preferable among those described above, a hydrogen atom or a methyl group is particularly preferable, and a hydrogen atom is more particularly preferable. The preferred range of those substituent groups are as described in the above. Namely, the alkyl group with 1 to 30 carbon atoms preferably has 1 to 20 carbon atoms, more preferably has 1 to 15 carbon atoms, particularly preferably has 1 to 10 carbon atoms, and more particularly preferably has 1 to 6 carbon atoms.

As for $R^{13}$, $R^{14}$ or $R^{18}$, a hydrogen atom, an alkyl group with 1 to 30 carbon atoms, or an aryl group with 6 to 30 carbon atoms is more preferable among those described above, and a hydrogen atom, a methyl group, or an aryl group with 6 to 30 carbon atoms is particularly preferable. The preferred range of those substituent groups are as described in the above. Namely, the alkyl group with 1 to 30 carbon atoms preferably has 1 to 20 carbon atoms, more preferably has 1 to 15 carbon atoms, particularly preferably has 1 to 10 carbon atoms, and more particularly preferably has 1 to 6 carbon atoms. Furthermore, the aryl group with 6 to 30 carbon atoms preferably has 6 to 20 carbon atoms, more preferably has 6 to 15 carbon atoms, and particularly preferably has 6 to 12 carbon atoms.

Adjacent $R^{12}$ to $R^{19}$ may bind to each other to form a condensed ring. Specifically, $R^{12}$ and $R^{13}$, $R^{13}$ and $R^{14}$, $R^{14}$ and $R^{15}$, $R^{15}$ and $R^{16}$, $R^{16}$ and $R^{17}$, $R^{17}$ and $R^{18}$, $R^{18}$ and $R^{19}$ may bind to each other to form a ring structure; however, it is preferable that any one of $R^{12}$ and $R^{13}$, $R^{13}$ and $R^{14}$, $R^{14}$ and $R^{15}$, and $R^{15}$ and $R^{16}$ bind to each other to form a ring structure, and it is more preferable that $R^{12}$ and $R^{13}$ or $R^{15}$ and $R^{16}$ bind to each other to form a ring structure.

By forming a ring structure as described above, stability of the iridium complex can be enhanced and light emission wavelength can be longer. When any one of $R^{12}$ and $R^{13}$, and $R^{14}$ and $R^{15}$ forms a condensed ring, the iridium complex of the present invention exhibits light emission in a red color range (e.g., 600 to 650 nm), and when any one of $R^{13}$ and $R^{14}$, and $R^{15}$ and $R^{16}$ forms a condensed ring, the iridium complex of the present invention exhibits light emission in a yellow color range (e.g., 540 to 590 nm). Among the condensed rings that are described above, it is preferable to form a 6-membered ring, and it is more preferable to form a benzene ring.

When adjacent $R^{12}$ to $R^{19}$ bind to each other to form a condensed ring, it is preferable to have any one of the following structures (L-1) to (L-4).

[Chem. 11]

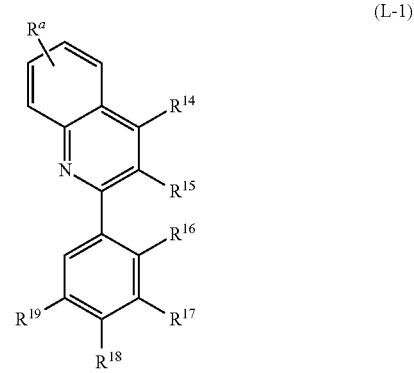

(L-1)

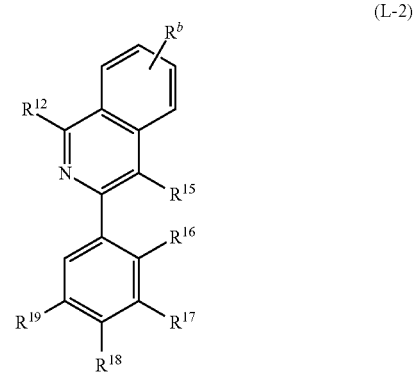

(L-2)

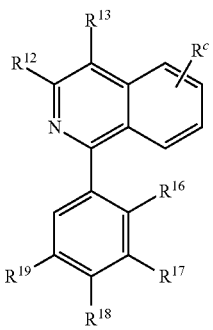

(L-3)

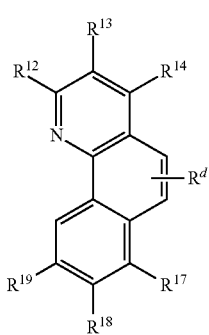

(L-4)

$R^1$ to $R^{19}$ in the structural formulae (L-1) to (L-4) have the same meaning as $R^1$ to $R^{19}$ in General Formula (1), and a preferred range thereof is also the same. $R^a$ to $R^d$ each independently represent a hydrogen atom, an alkyl group with 1 to 30 carbon atoms, an aryl group with 6 to 30 carbon atoms, a halogen atom, or a cyano group. $R^a$ to $R^d$ preferably include a hydrogen atom or an alkyl group with 1 to 30 carbon atoms, and more preferably, it is a hydrogen atom or a methyl group.

Furthermore, according to a method of introducing a substituent group to $R^1$ to $R^{19}$ of the iridium complex represented by General Formula (1) of the present invention, the light emission wavelength of iridium complex can be controlled. For example, when a fluorine atom is introduced to $R^{16}$ or $R^{18}$, the light emission shifts to a shorter wavelength. Furthermore, when a trifluoromethyl group or a cyano group is introduced to $R^{17}$, the light emission shifts to a shorter wavelength.

Furthermore, when a halogen atom (preferably a bromine atom or an iodine atom) is introduced to $R^1$ to $R^{19}$, a carbon-carbon bond may be formed by using Suzuki coupling reaction, which uses a widely available boronic acid compound, as represented by Formula (C), and various substituent groups (e.g., alkyl group, aryl group, or the like) can be easily introduced, and thus it is useful as a precursor for synthesizing a new iridium complex.

[Chem. 12]

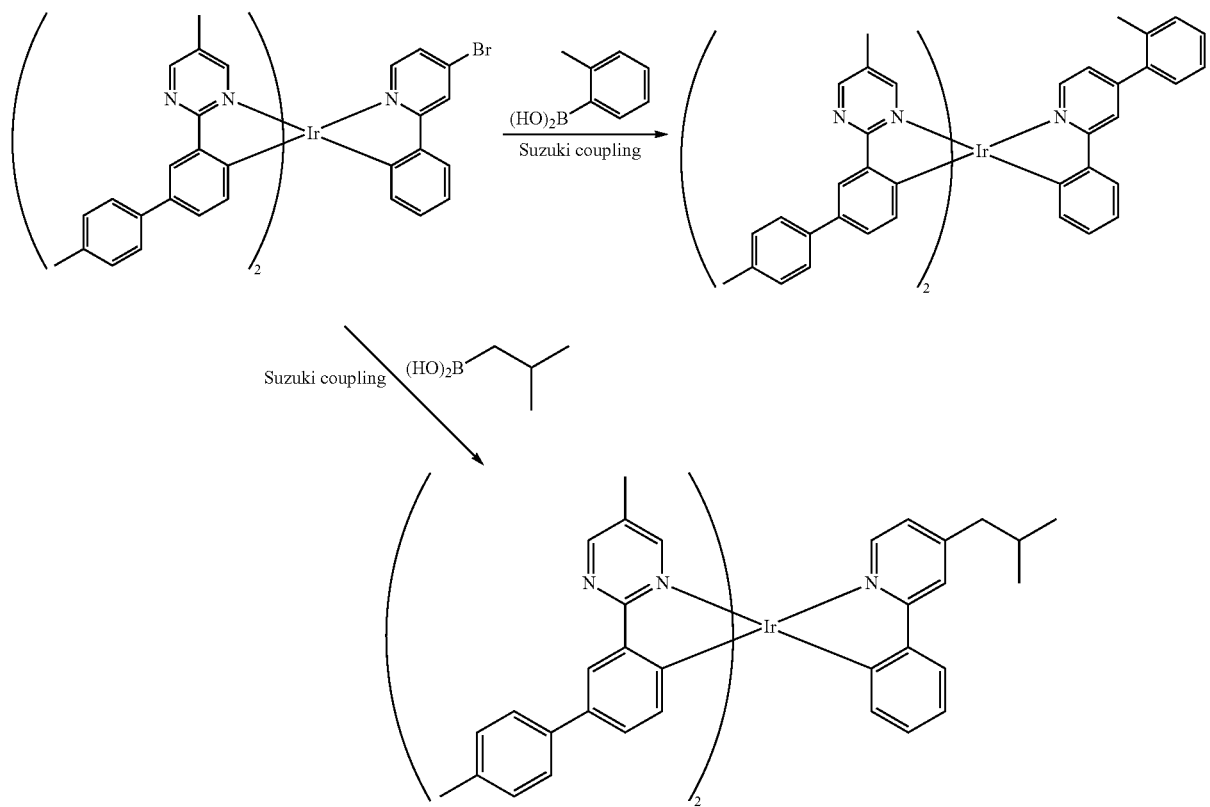

Formula (C)

Among the iridium complexes that are represented by General Formula (1), a case in which $R^{13}$ is an aryl group with 6 to 30 carbon atoms, in particular, an iridium complex represented by General Formula (9) is preferable.

Among the iridium complexes that are represented by General Formula (1), a case in which $R^{18}$ is an aryl group with 6 to 30 carbon atoms, in particular, an iridium complex represented by General Formula (11) is preferable.

[Chem. 13]

[Chem. 15]

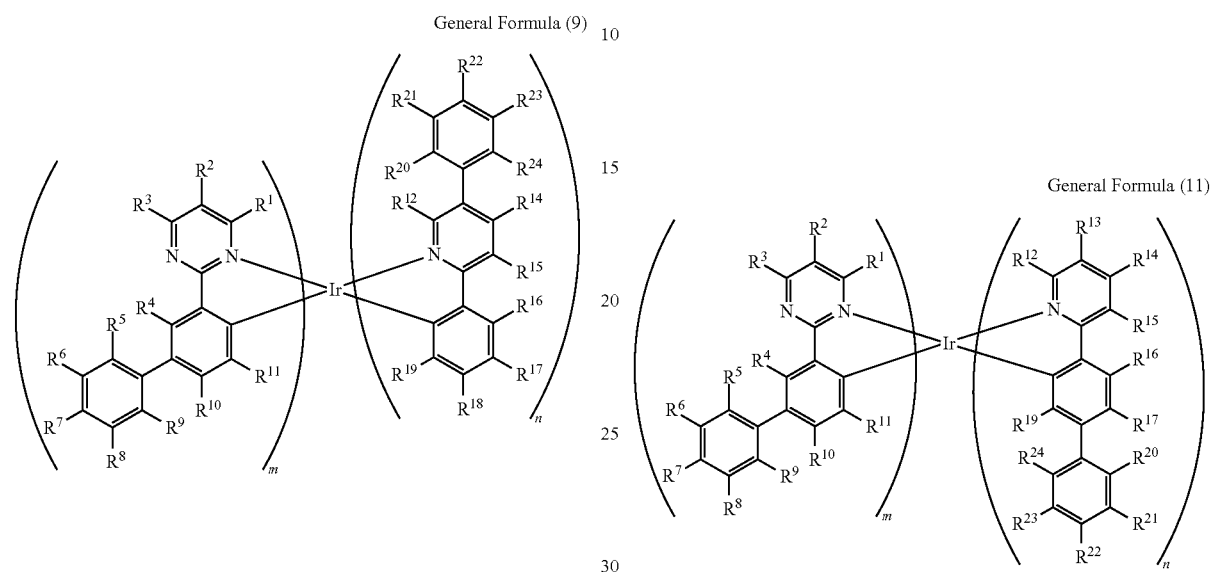

General Formula (9)

General Formula (11)

Among the iridium complexes that are represented by General Formula (1), a case in which $R^{14}$ is an aryl group with 6 to 30 carbon atoms, in particular, an iridium complex represented by General Formula (10) is preferable.

Among the iridium complexes that are represented by General Formula (1), a case in which $R^{15}$ and $R^{16}$ bind to each other to form a condensed ring, in particular, an iridium complex represented by General Formula (12) is preferable.

[Chem. 14]

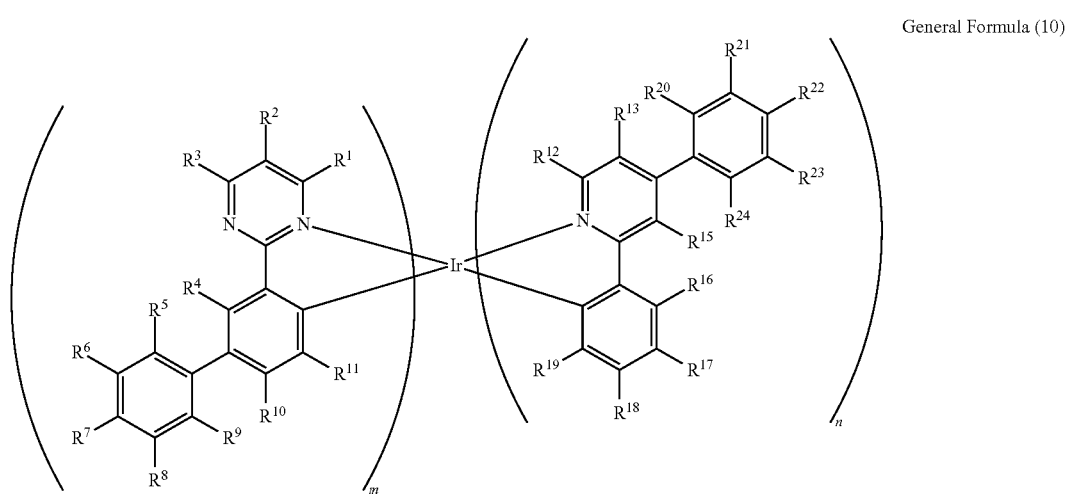

General Formula (10)

[Chem. 16]

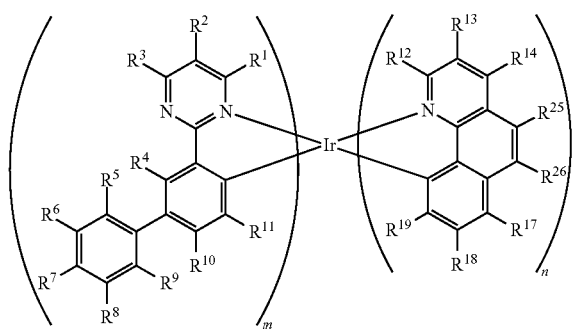

General Formula (12)

Among the iridium complexes that are represented by General Formula (1), a case in which $R^{12}$ and $R^{13}$ bind to each other to form a condensed ring, in particular, an iridium complex represented by General Formula (13) is preferable.

[Chem. 36]

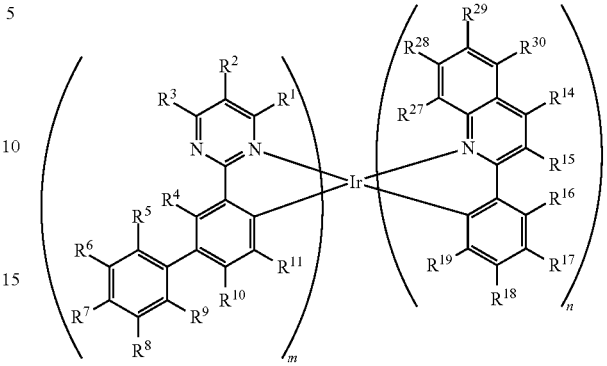

General Formula (13)

Symbols that are described in General Formulae (9) to (13) (i.e., $R^1$ to $R^{30}$) are explained hereinbelow.

$R^1$ to $R^{19}$ have the same meaning as $R^1$ to $R^{19}$ in General Formula (1), and a preferred range thereof is also the same.

$R^{20}$ to $R^{30}$ each independently represent a hydrogen atom, an alkyl group with 1 to 30 carbon atoms, an aryl group with 6 to 30 carbon atoms, a halogen atom, or a cyano group. Definition and preferred range of the aforementioned substituent groups are the same as $R^1$ to $R^{19}$ in General Formula (1). $R^{20}$ to $R^{30}$ are preferably a hydrogen atom or an alkyl group with 1 to 30 carbon atoms, more preferably a hydrogen atom or a methyl group, and particularly preferably a hydrogen atom.

For producing the iridium complex of the present invention which is represented by General Formula (1), for example, there are routes of the following Formula (D) or Formula (E).

Formula (D)

[Chem. 17]

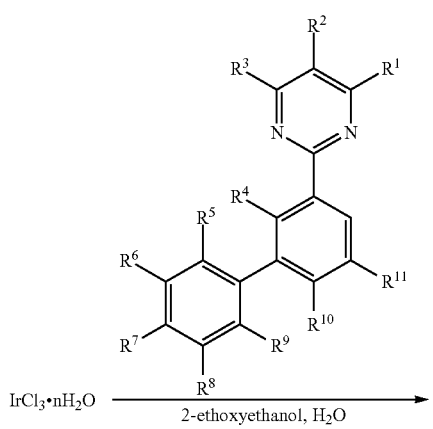

IrCl$_3$·nH$_2$O $\xrightarrow{\text{2-ethoxyethanol, H}_2\text{O}}$

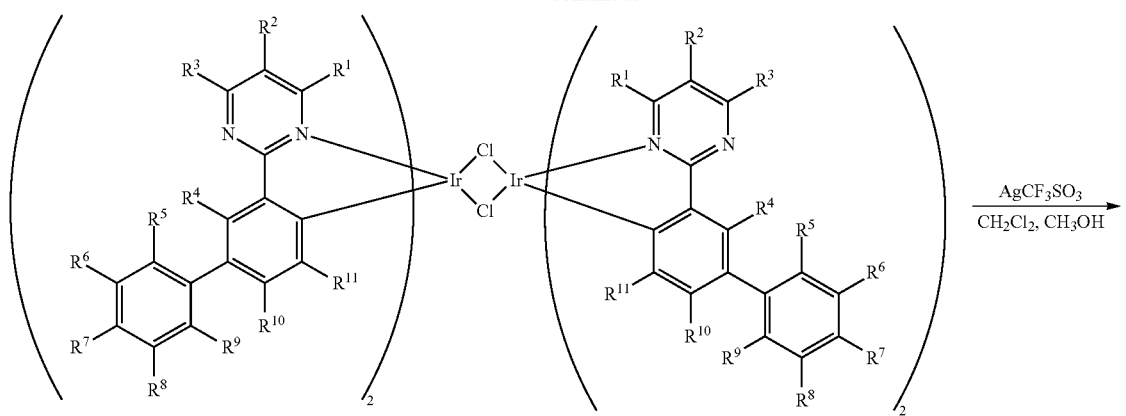
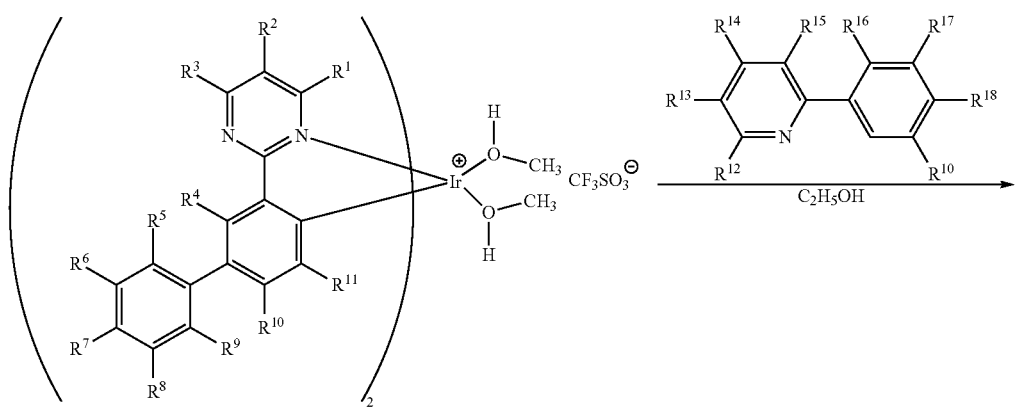
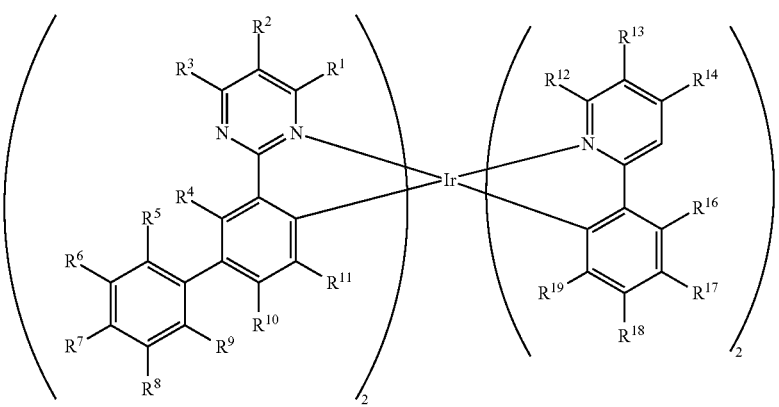

-continued
Formula (E)
[Chem. 18]
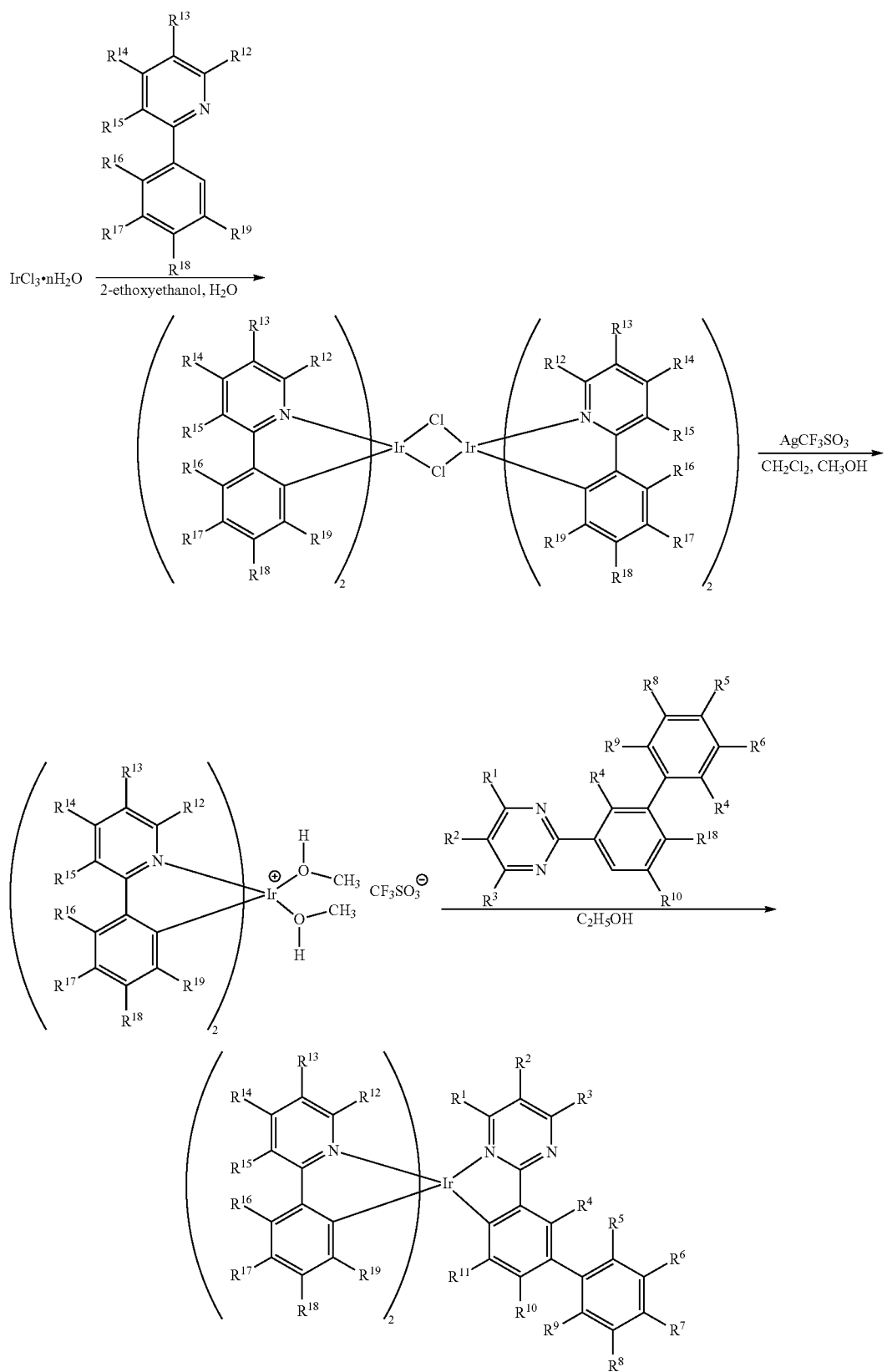

With regard to the iridium complex of the present invention which is represented by General Formula (1), synthesis thereof can be made, other than those described above, by referencing known publications including WO 2012/166608 A (Patent Literature 7), WO 2010/056669 A (Patent Literature 8), WO 2010/111755 A (Patent Literature 9), or WO 2012/158851 A (Patent Literature 10), or the like.

In general, ligand scrambling may easily occur at the time of introducing a different cyclometallated ligand for synthesis of a heteroleptic iridium complex and polarity is similar among generated impurities, and thus it is disclosed that separation and purification are very difficult to achieve (see, for example, WO 2010/028151 A (Patent Literature 11)). Specific reaction examples are shown with Formulae (F) and (G).

[Chem. 19]

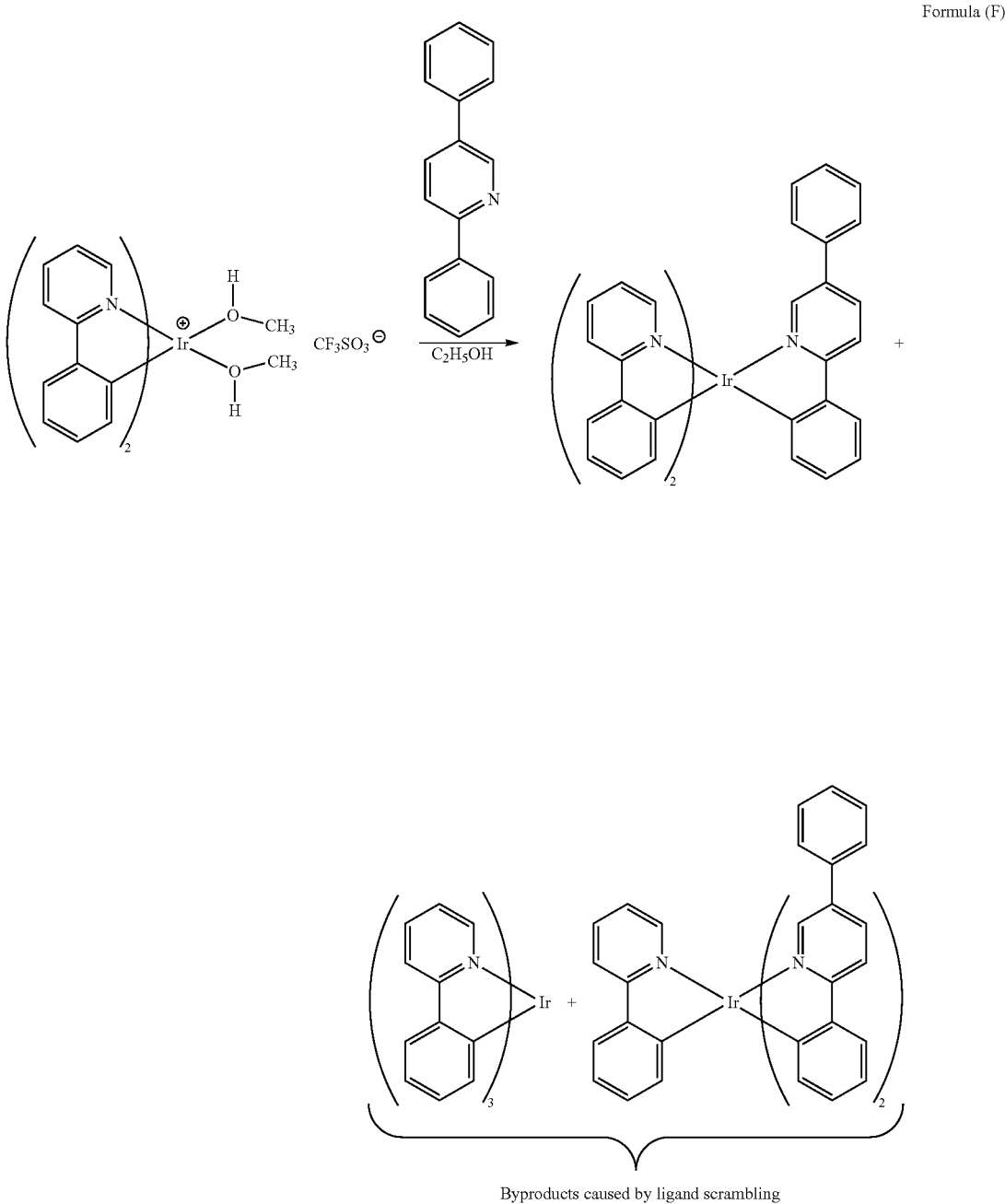

Formula (F)

Byproducts caused by ligand scrambling

[Chem. 20]

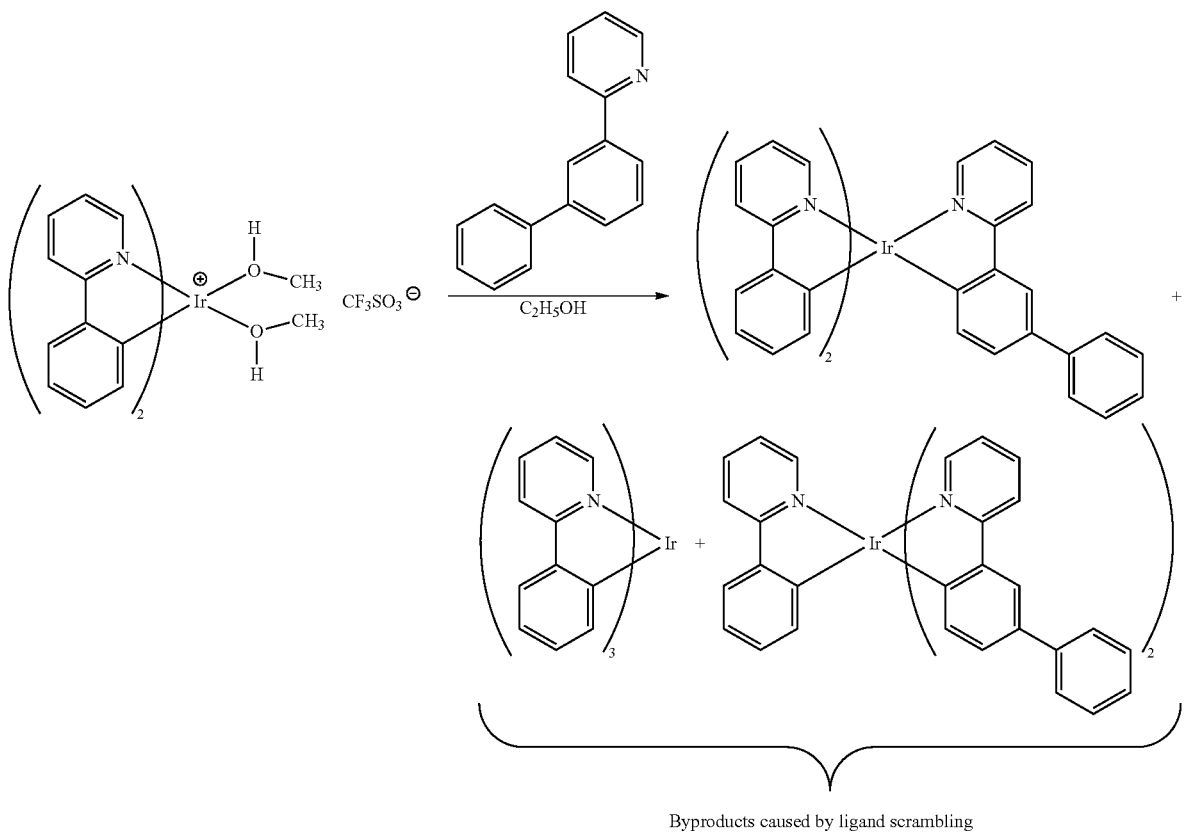

Formula (G)

Byproducts caused by ligand scrambling

Incidentally, regarding the iridium complex of the present invention which is represented by General Formula (1), it has been unexpectedly found that the ligand scrambling hardly occurs during the synthesis. It was also found that, even when the ligand scrambling occurs during the synthesis, byproducts can be easily separated by using silica gel column chromatography, for example.

With regard to the iridium complex of the present invention which is represented by General Formula (1), it is believed by the inventors of the present invention that, since there are 2 kinds of a ligand that are represented by General Formulae (2) and (3) (i.e., 2-phenylpyridine derivative ligand and 2-phenylpyrimidine derivative ligand) and the polarity is greatly different between those ligands, byproducts that are generated by ligand scrambling can be easily separated and purified.

It was also found that, in a case in which an aryl group with 6 to 30 carbon atoms is introduced to $R^{12}$ to $R^{19}$ of a 2-phenylpyridine derivative ligand which is represented by General Formula (3), easiness of an occurrence of the ligand scrambling is different at the time of synthesizing the iridium complex of the present invention which is represented by General Formula (1). Namely, it was found that introducing the aryl group to the pyridine ring of a 2-phenylpyridine derivative ligand (for example, $R^{13}$ or $R^{14}$) is more difficult to have an occurrence of the ligand scrambling compared to a case in which the introduction is made to the phenyl group (for example, $R^{18}$).

Namely, among the iridium complexes of the present invention that are represented by General Formula (1), those preferred in terms of synthesis are an iridium complex in which $R^{12}$ to $R^{19}$ are a hydrogen atom or an alkyl group with 1 to 30 carbon atoms, an iridium complex in which $R^{13}$ is an aryl group with 6 to 30 carbon atoms (preferably, iridium complex represented by General Formula (9)), an iridium complex in which $R^{14}$ is an aryl group with 6 to 30 carbon atoms (preferably, iridium complex represented by General Formula (10)), and an iridium complex in which $R^{15}$ and $R^{16}$ bind to each other to form a condensed ring (preferably, iridium complex represented by General Formula (12)).

The iridium complex according to the present invention can be provided, after treatment according to a common post treatment for synthetic reaction, with having purification if necessary or without having purification. As for the method for the post treatment, for example, extraction, cooling, crystallization based on addition of water or an organic solvent, or an operation of distilling off a solvent from a reaction mixture, or the like can be carried out either singly or in combination thereof. As for the method for purification, recrystallization, distillation, sublimation, column chromatography, or the like can be carried out either singly or in combination thereof.

Hereinbelow, the representative examples of the iridium complex of the present invention which is represented by General Formula (1) are shown in Table 1A to Table 13, but the present invention is not limited to them.

TABLE 1A
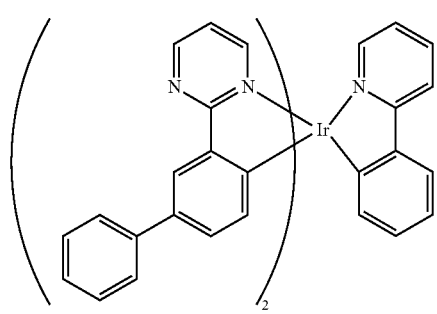 (K-1)
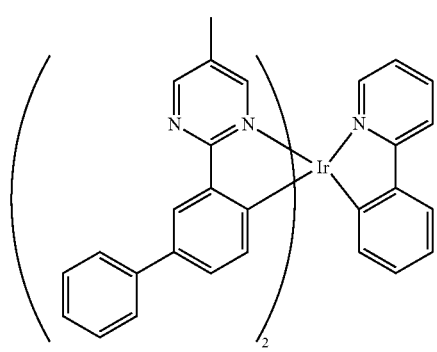 (K-2)
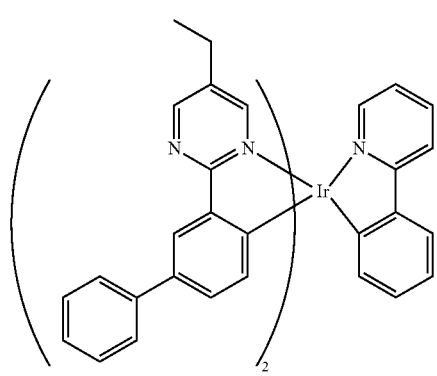 (K-3)
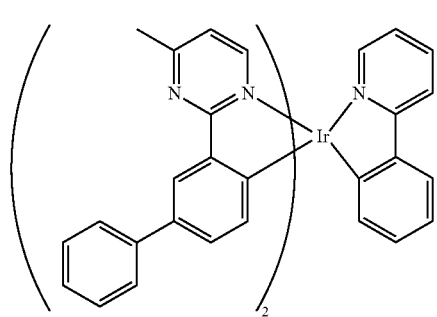 (K-4)
TABLE 1A-continued
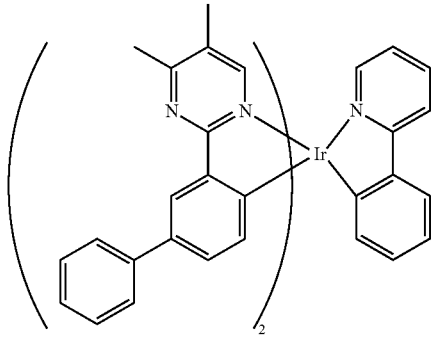 (K-5)
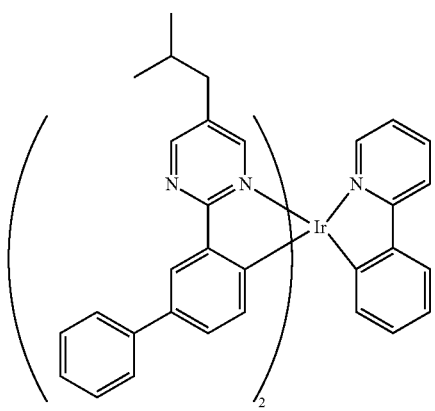 (K-6)
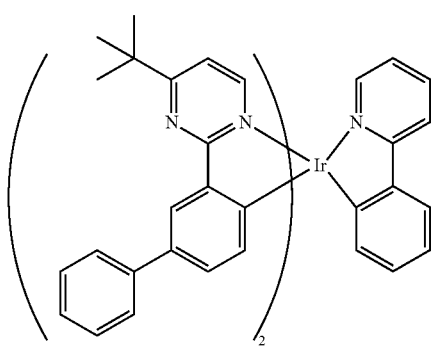 (K-7)
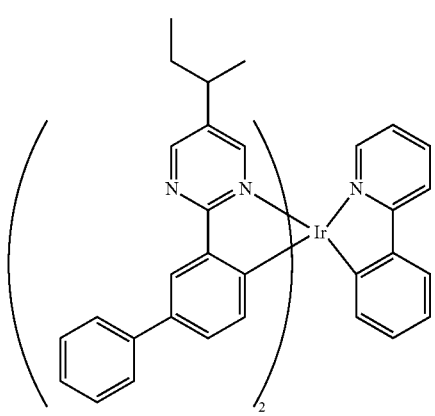 (K-8)

TABLE 1A-continued
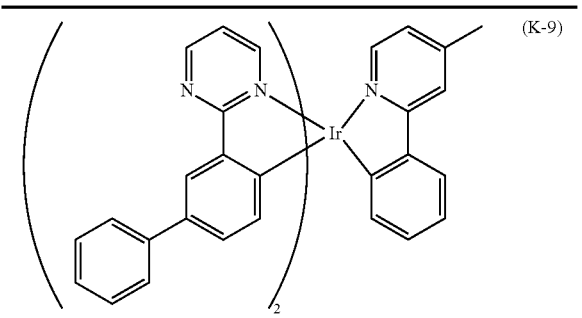
(K-9)
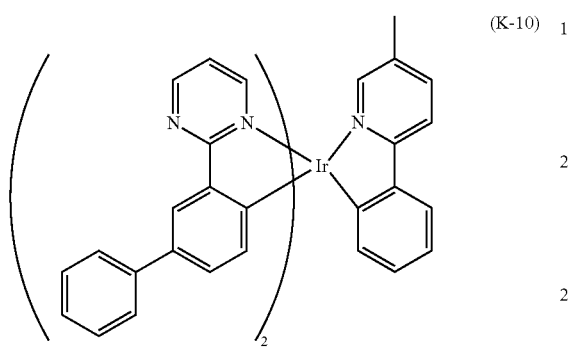
(K-10)
TABLE 1A-continued
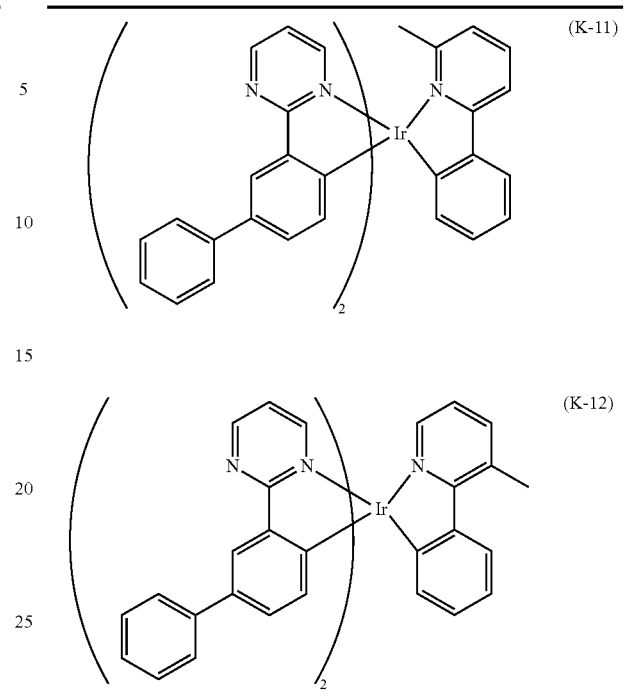
(K-11)
(K-12)
TABLE 1B
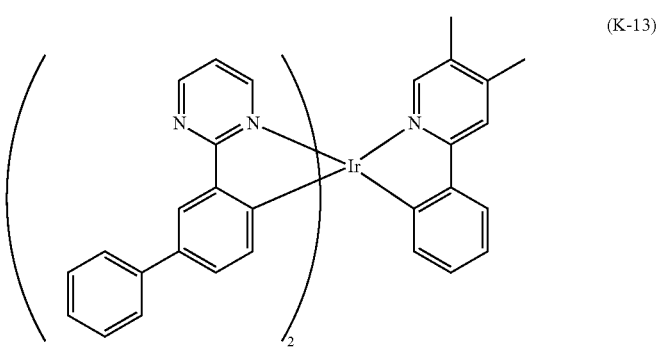
(K-13)
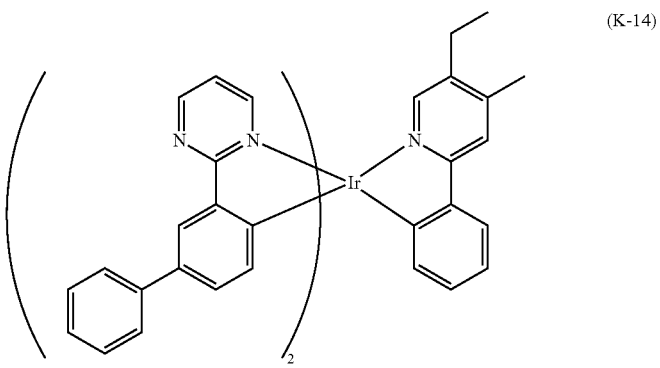
(K-14)

TABLE 1B-continued
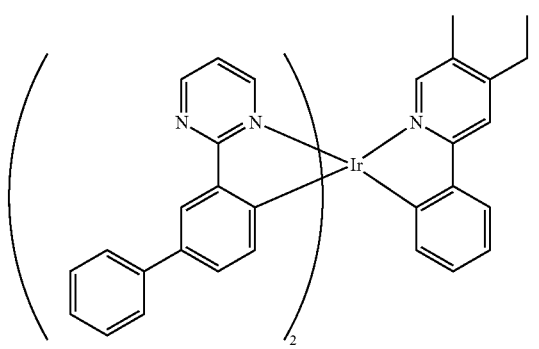
(K-15)
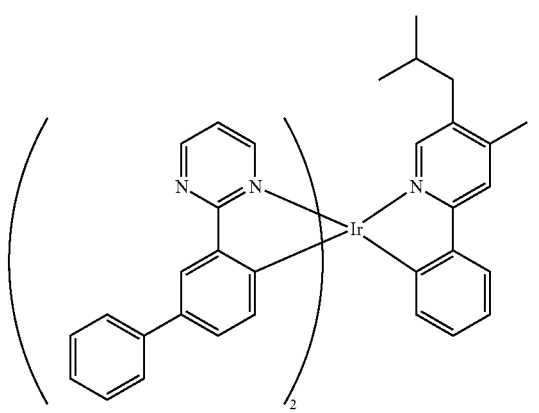
(K-16)
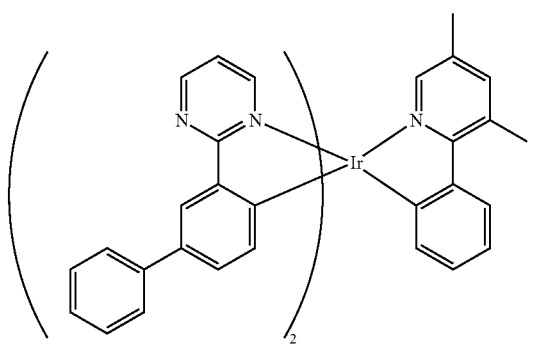
(K-17)
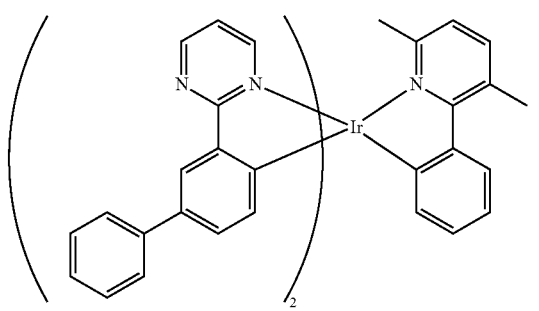
(K-18)

TABLE 1B-continued
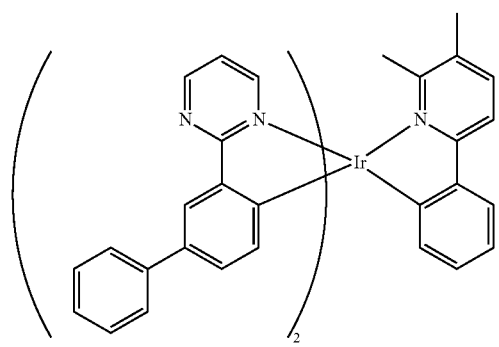
(K-19)
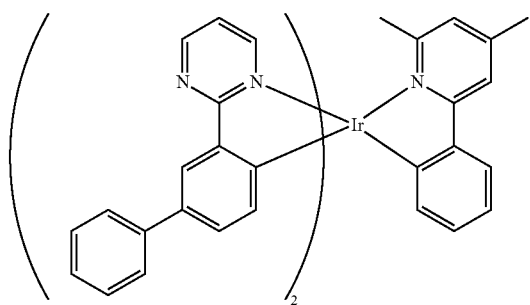
(K-20)
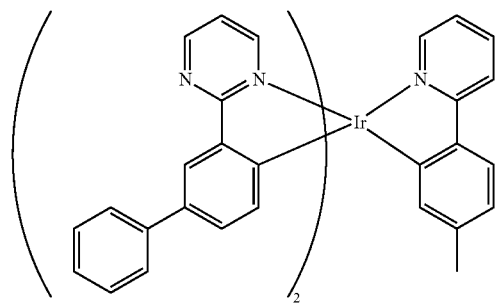
(K-21)
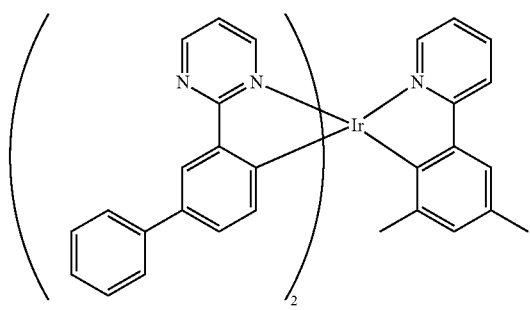
(K-22)
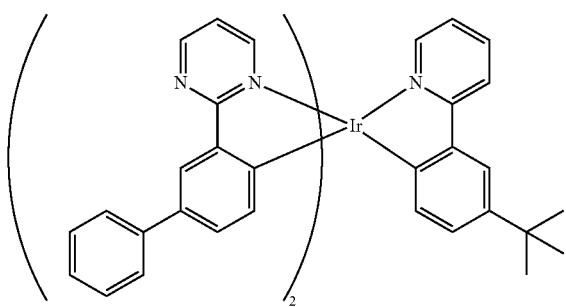
(K-23)

TABLE 1B-continued
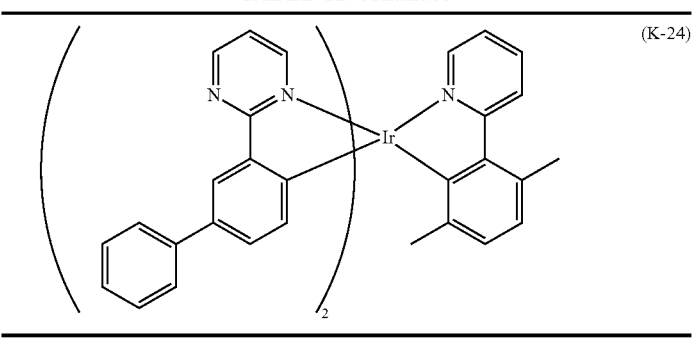
(K-24)
TABLE 2A
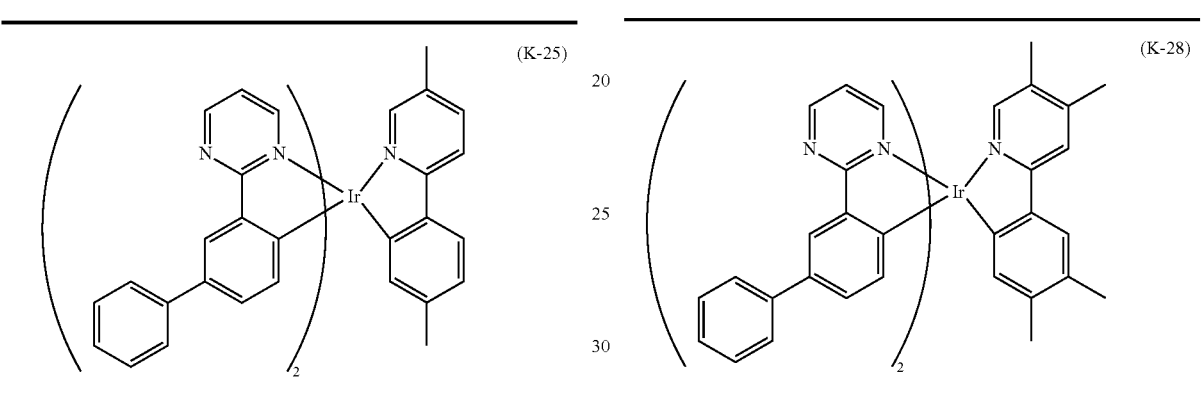
(K-25)
(K-28)
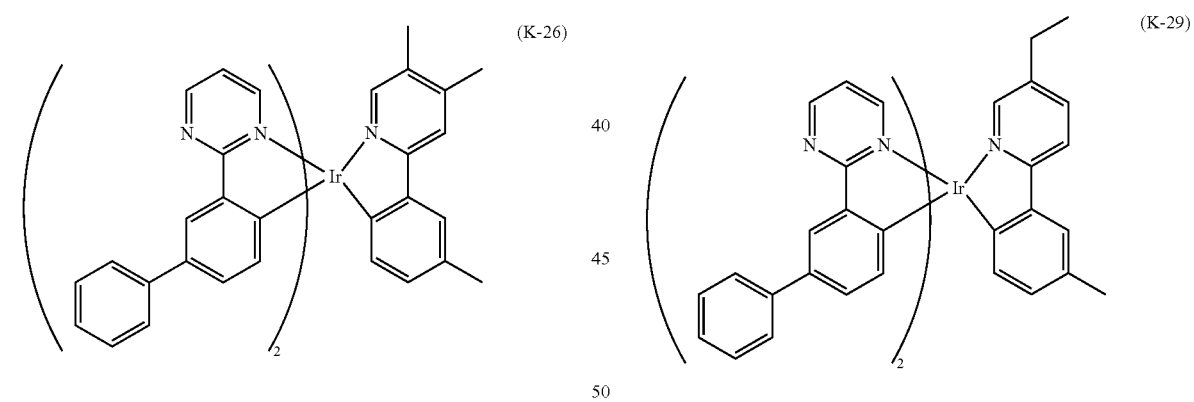
(K-26)
(K-29)
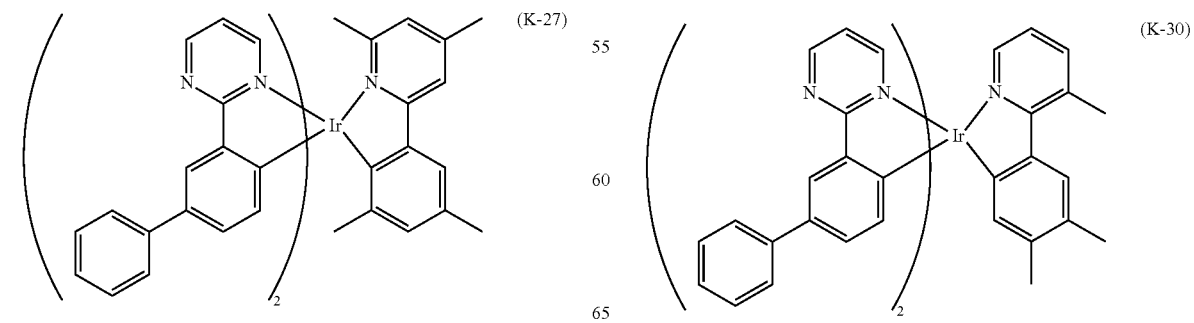
(K-27)
(K-30)

TABLE 2A-continued
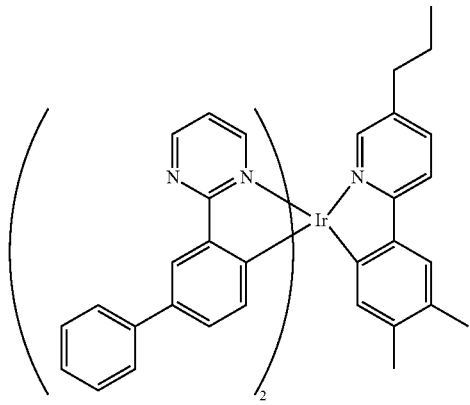 (K-31)
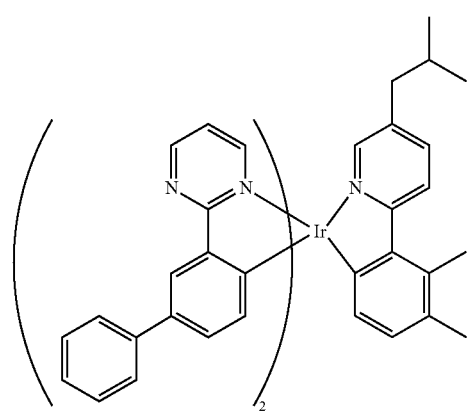 (K-32)
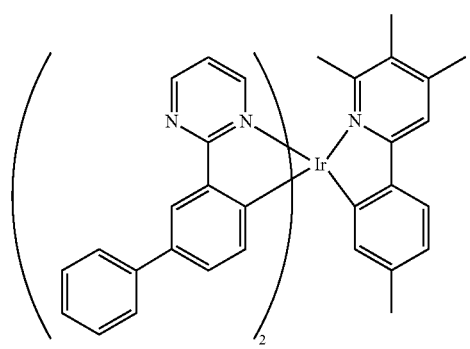 (K-33)
TABLE 2A-continued
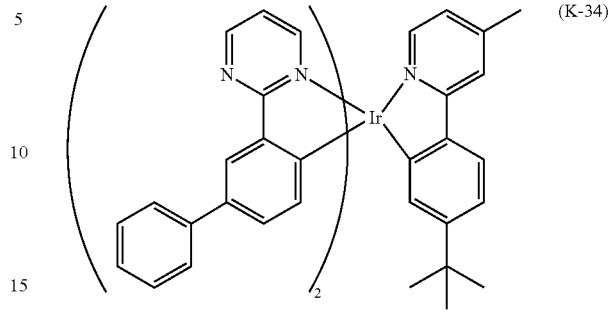 (K-34)
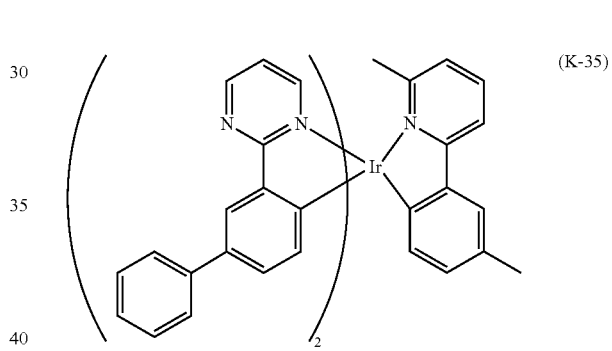 (K-35)
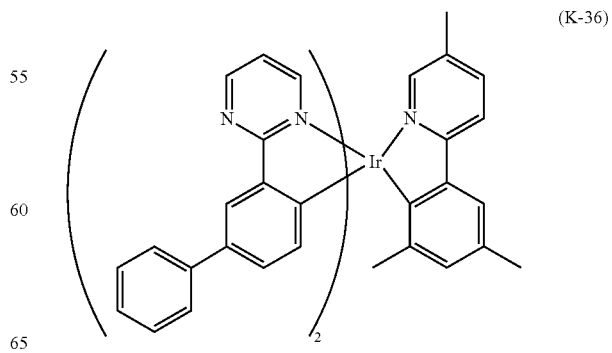 (K-36)

TABLE 2B
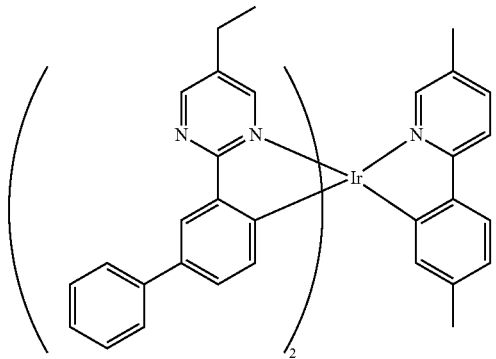
(K-37)
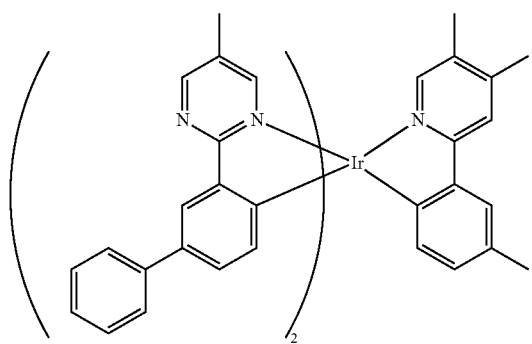
(K-38)
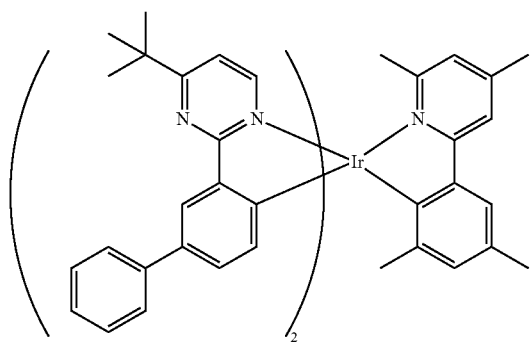
(K-39)
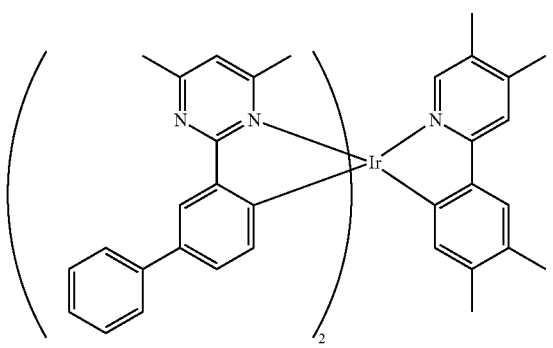
(K-40)

TABLE 2B-continued
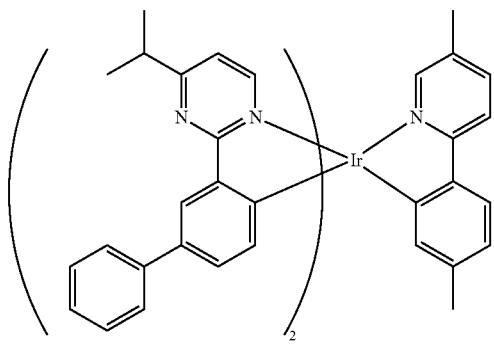
(K-41)
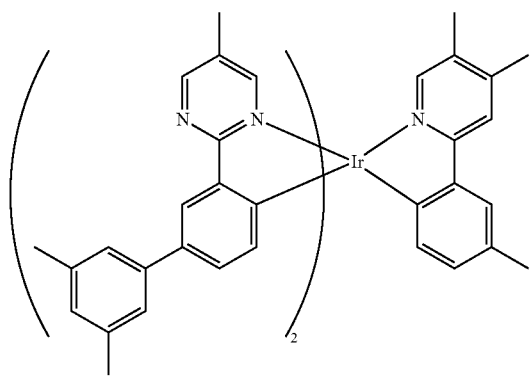
(K-42)
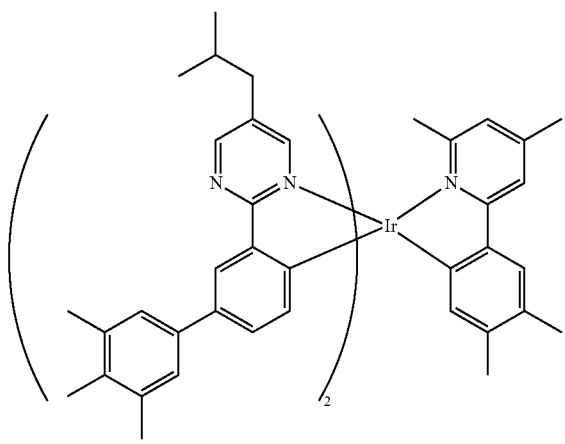
(K-43)
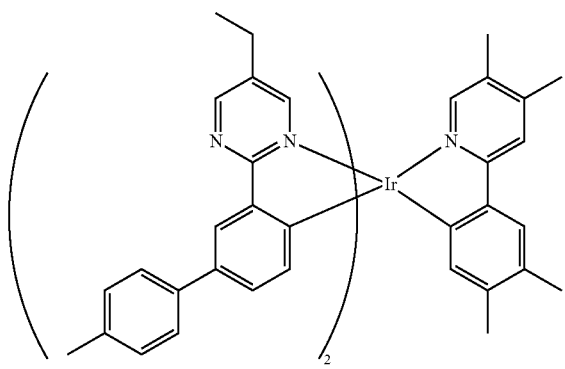
(K-44)

TABLE 2B-continued
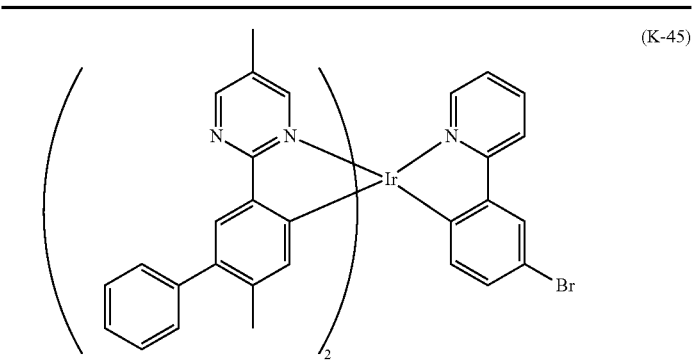
(K-45)
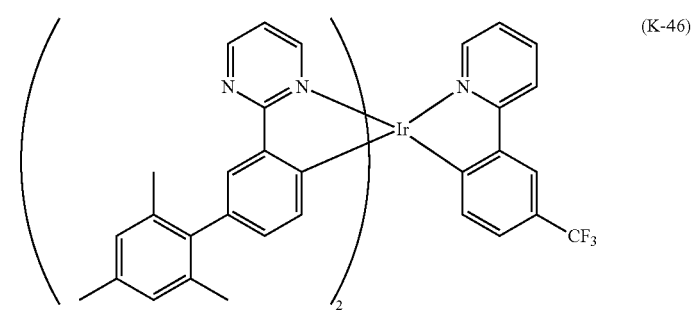
(K-46)
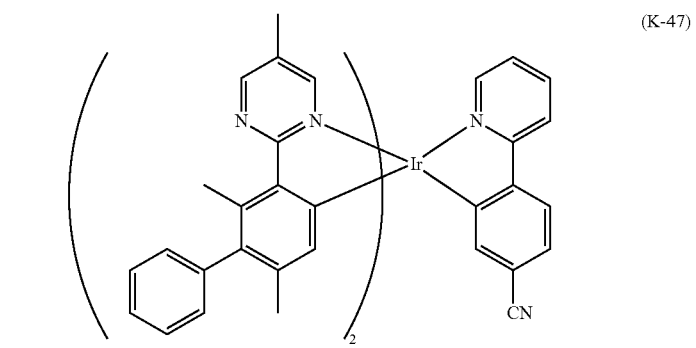
(K-47)
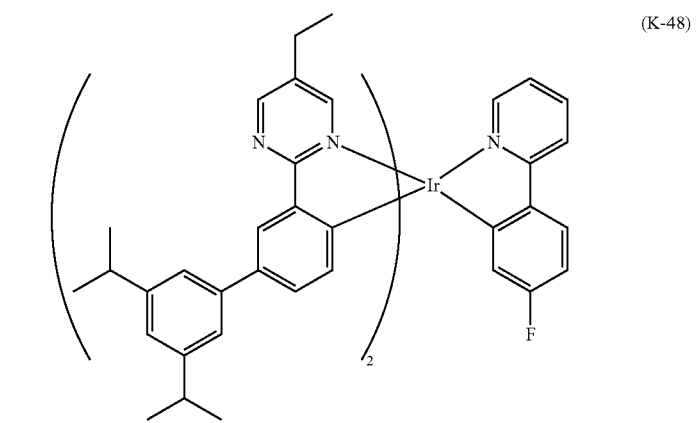
(K-48)

TABLE 3A
(K-49)
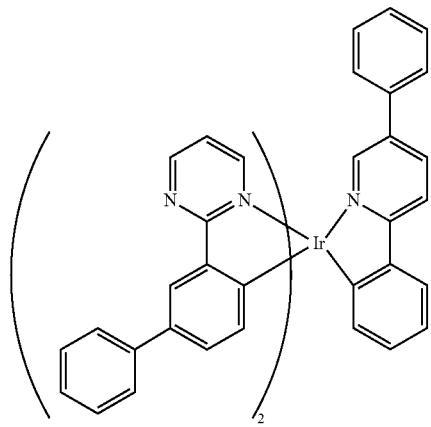
(K-50)
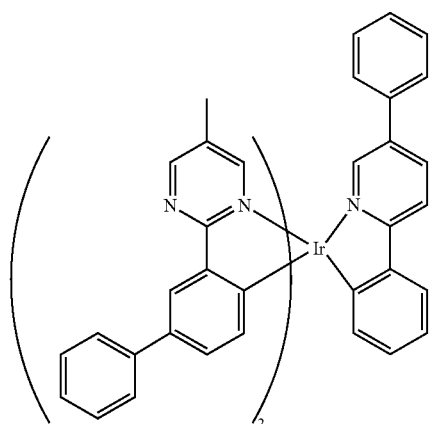
(K-51)
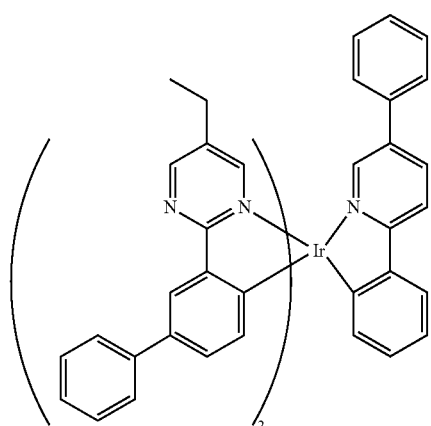
TABLE 3A-continued
(K-52)
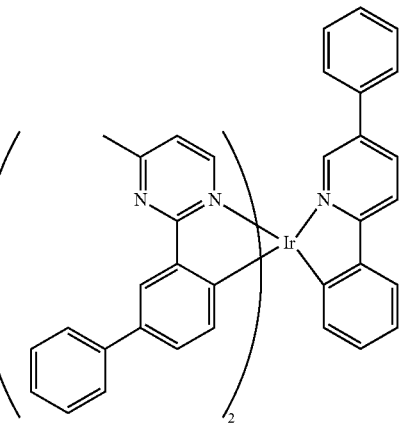
(K-53)
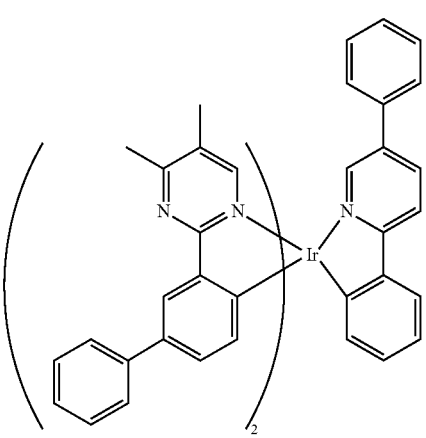
(K-54)
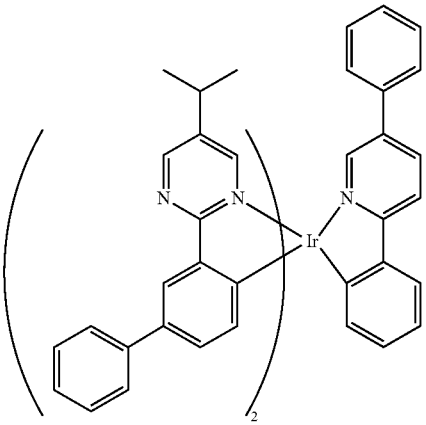

TABLE 3A-continued
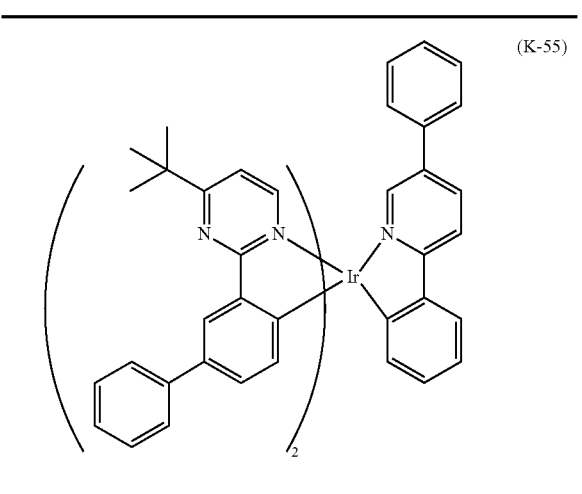
(K-55)
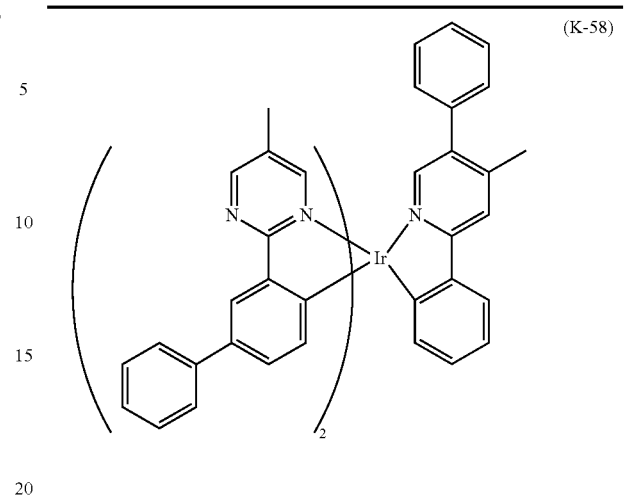
(K-58)
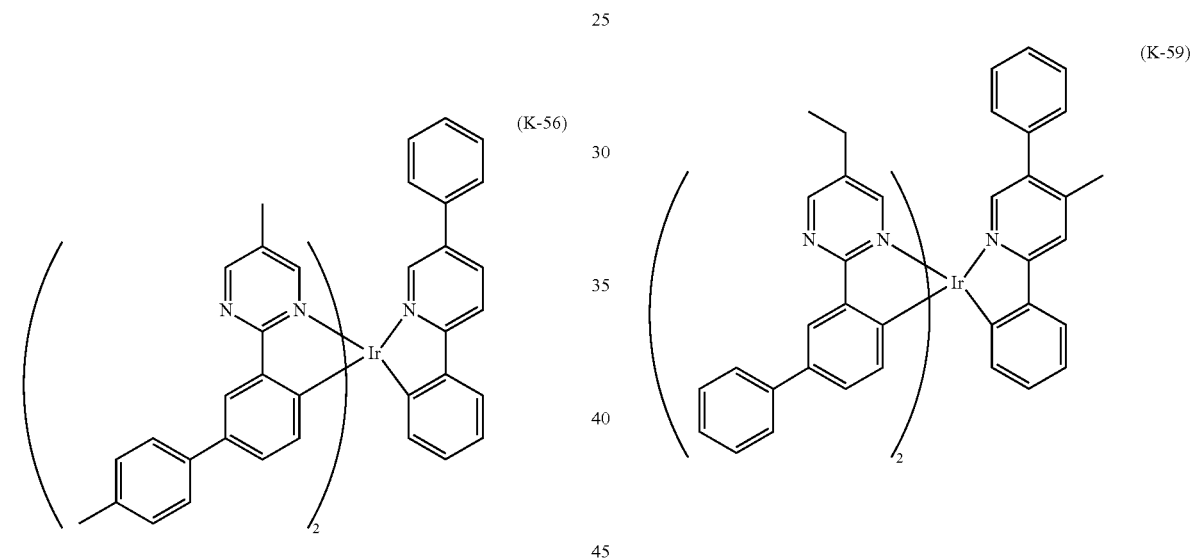
(K-56)
(K-59)
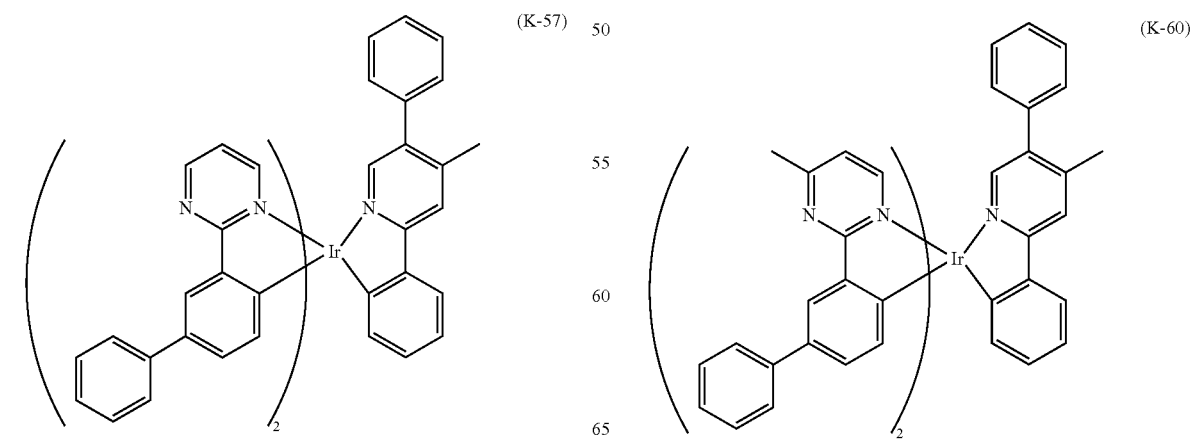
(K-57)
(K-60)

TABLE 3B
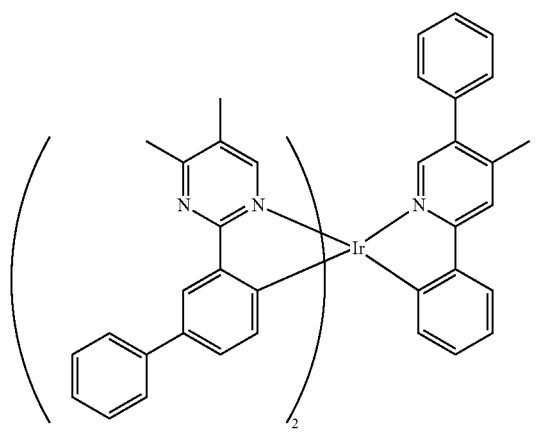
(K-61)
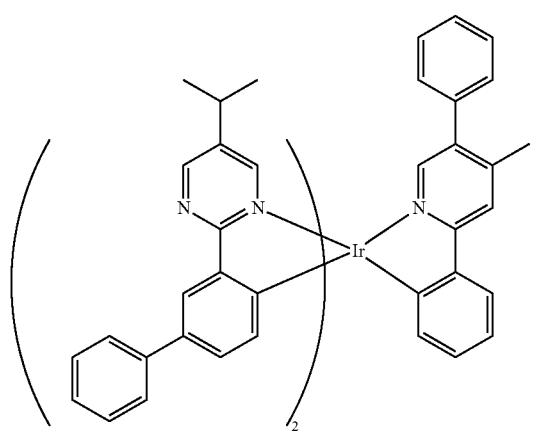
(K-62)
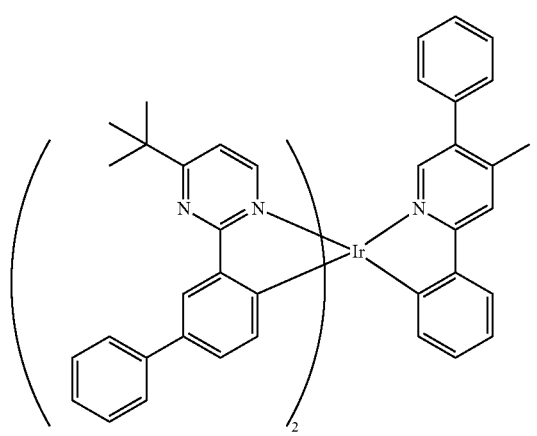
(K-63)

TABLE 3B-continued
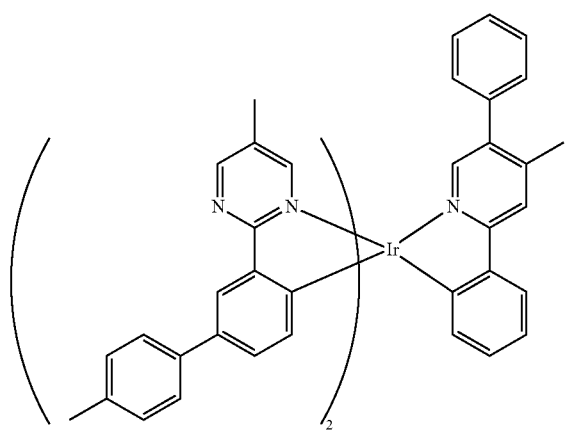
(K-64)
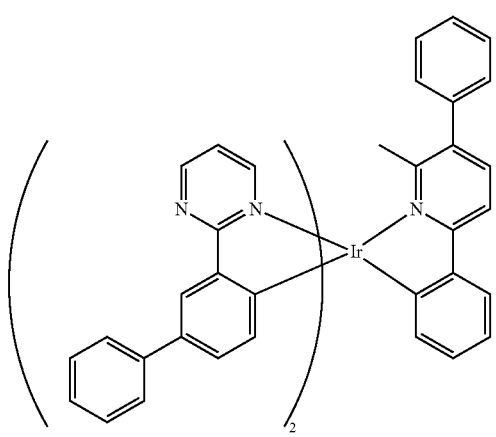
(K-65)
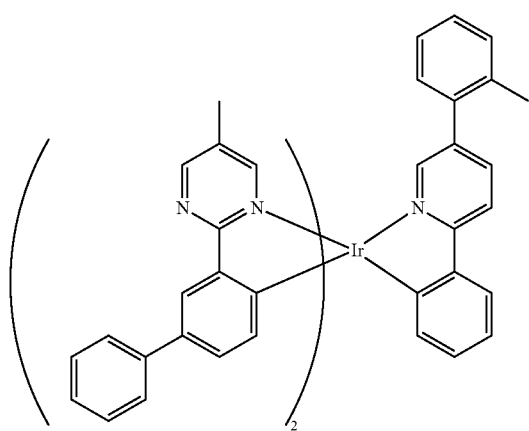
(K-66)

TABLE 3B-continued
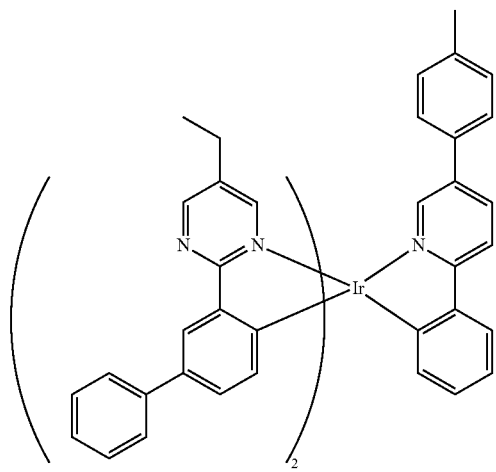
(K-67)
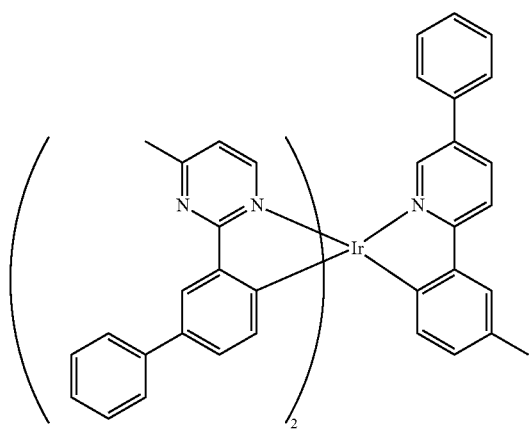
(K-68)
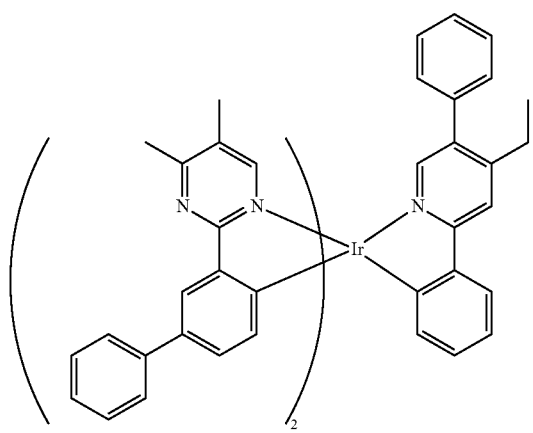
(K-69)

TABLE 3B-continued
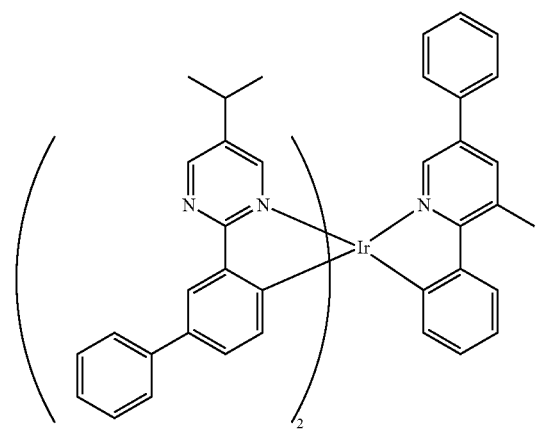
(K-70)
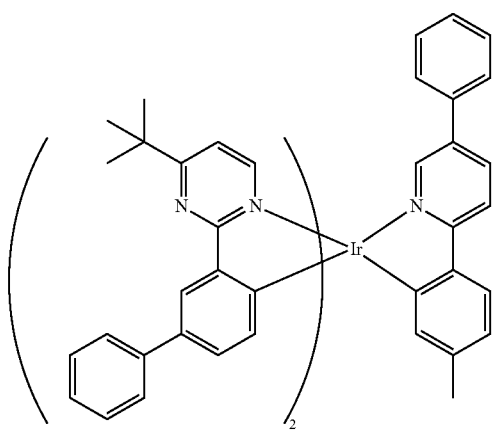
(K-71)
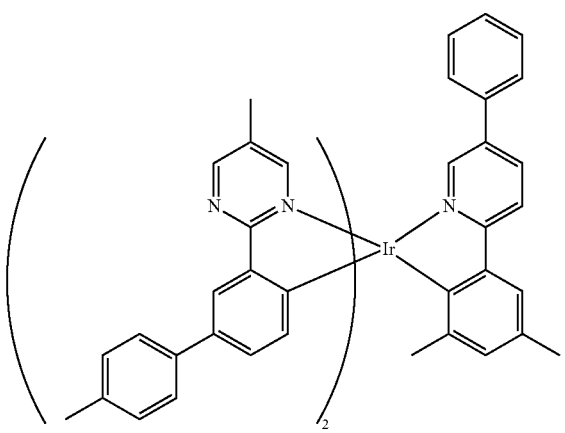
(K-72)

TABLE 4A
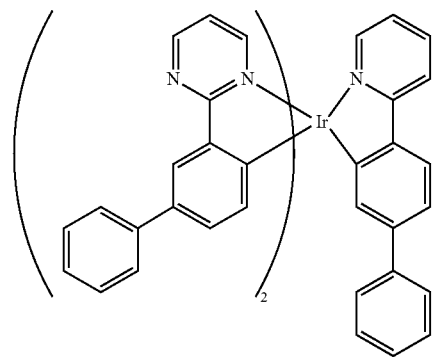
(K-73)
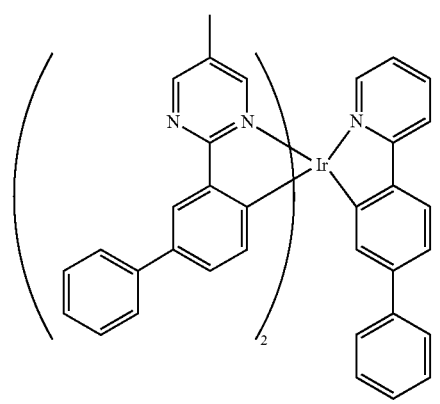
(K-74)
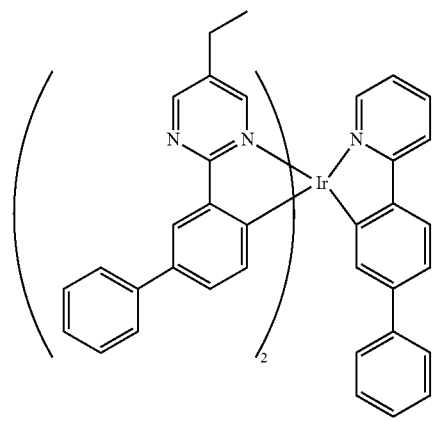
(K-75)
TABLE 4A-continued
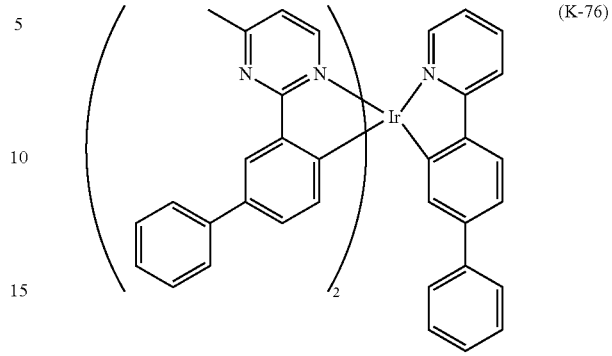
(K-76)
(K-77)
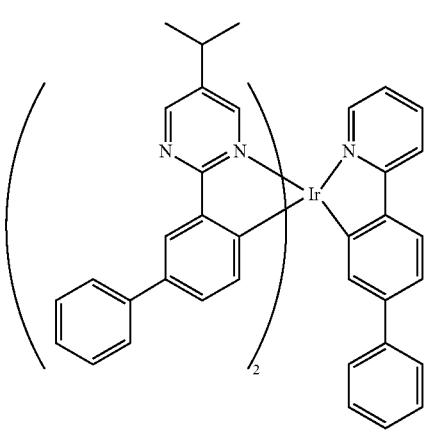
(K-78)

TABLE 4A-continued
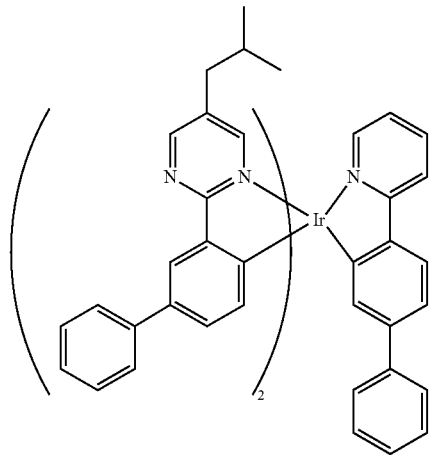 (K-79)
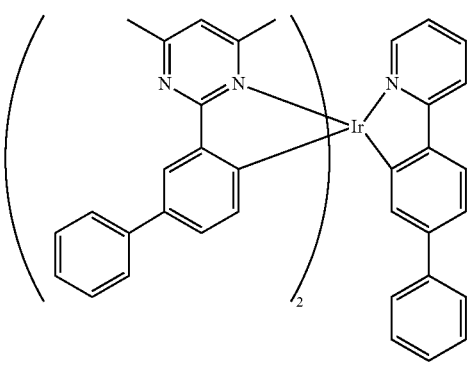 (K-80)
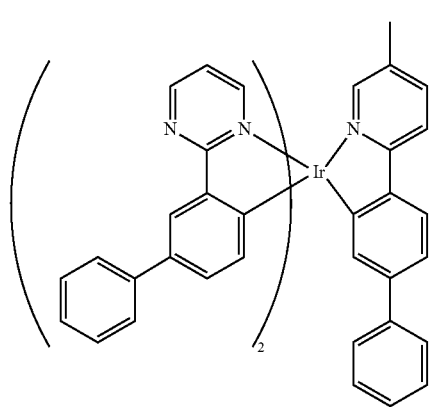 (K-81)
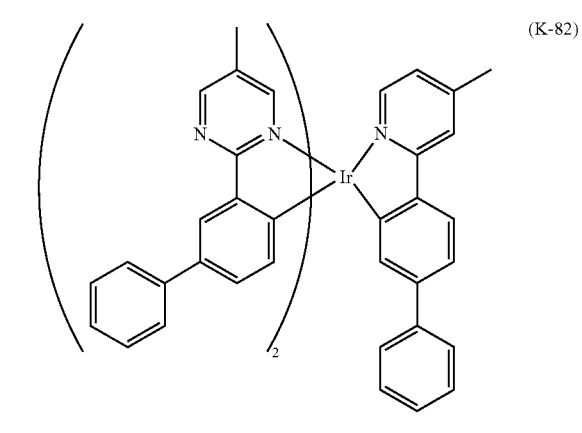 (K-82)
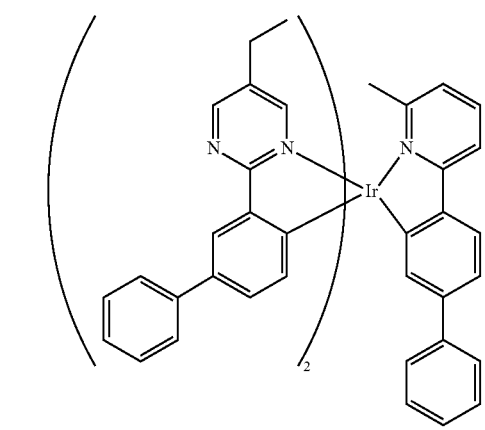 (K-83)
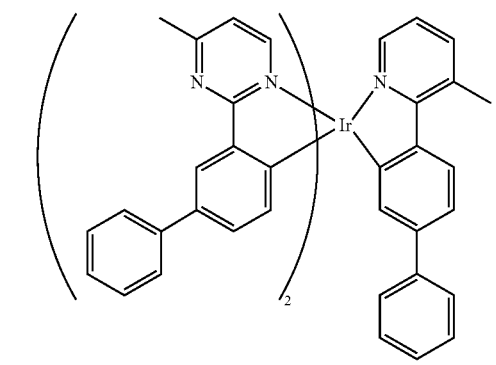 (K-84)

TABLE 4B
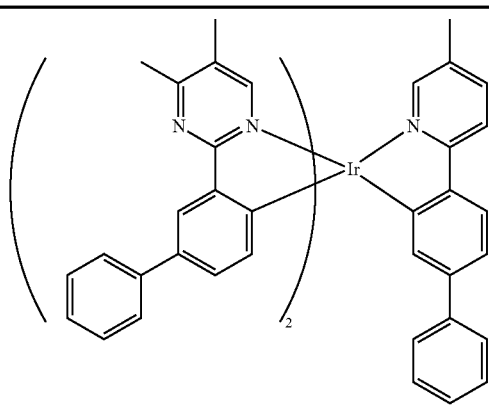
(K-85)
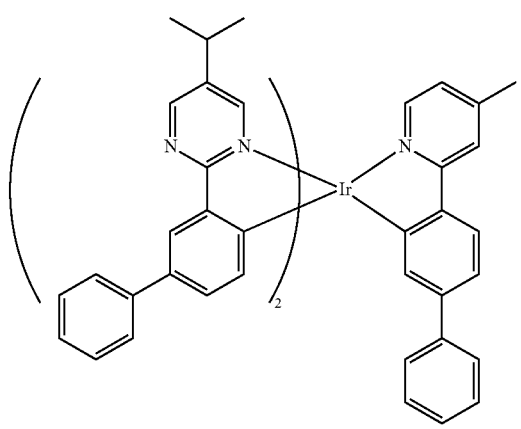
(K-86)
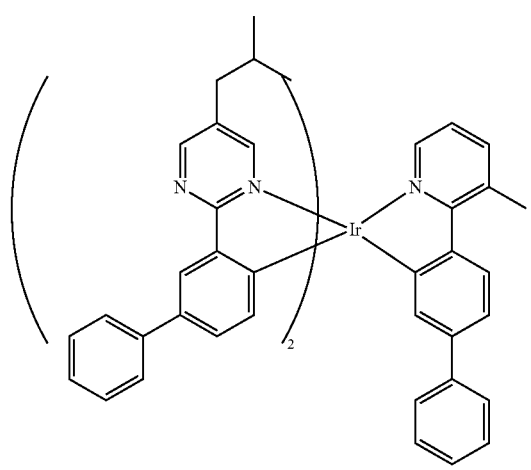
(K-87)

TABLE 4B-continued
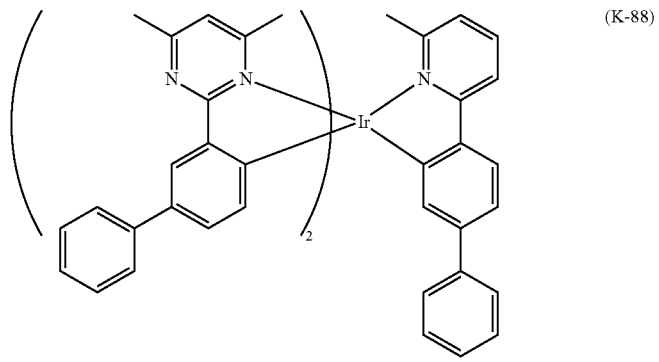
(K-88)
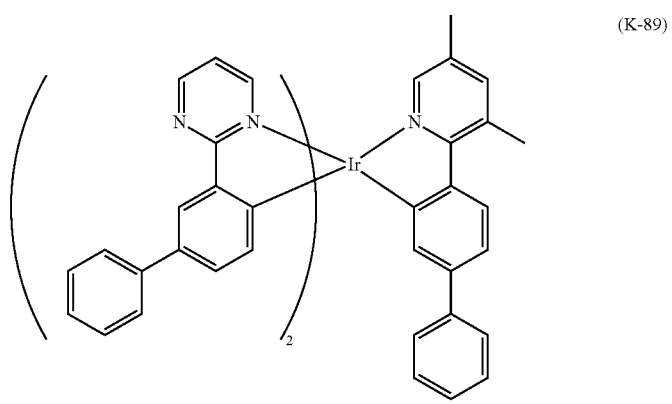
(K-89)
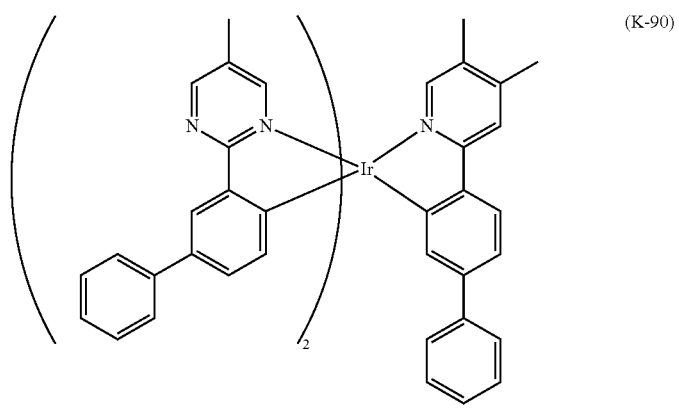
(K-90)
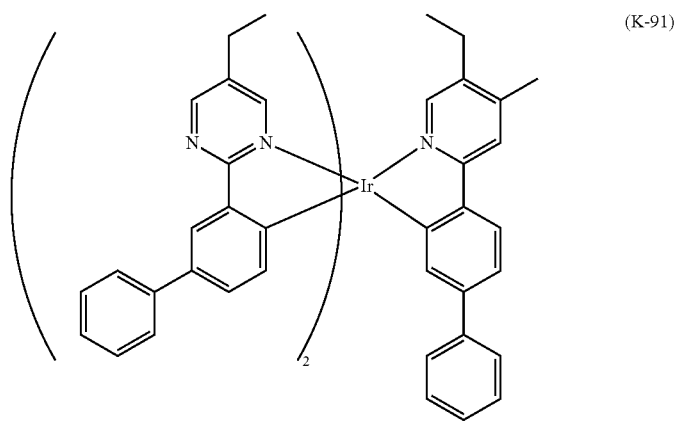
(K-91)

TABLE 4B-continued
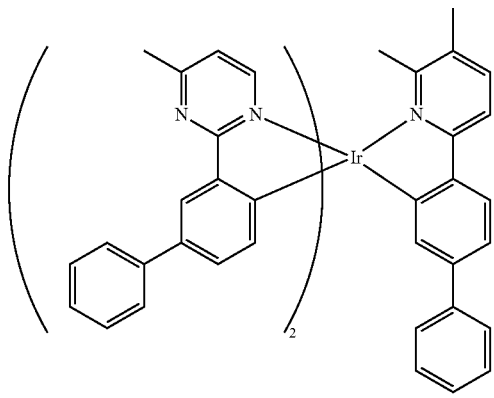
(K-92)
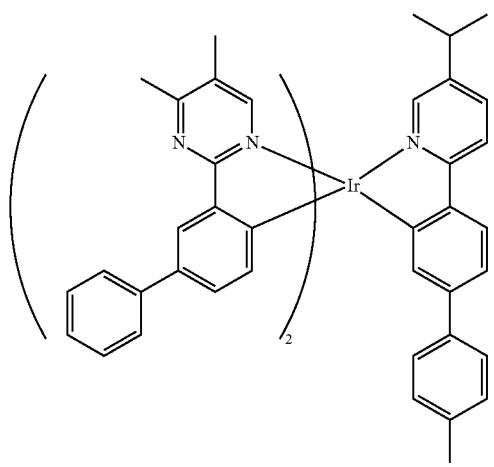
(K-93)
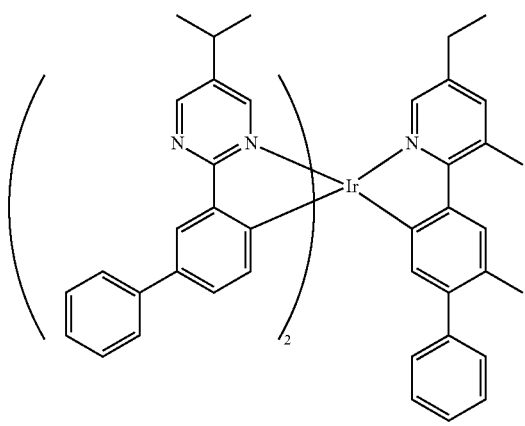
(K-94)

TABLE 4B-continued
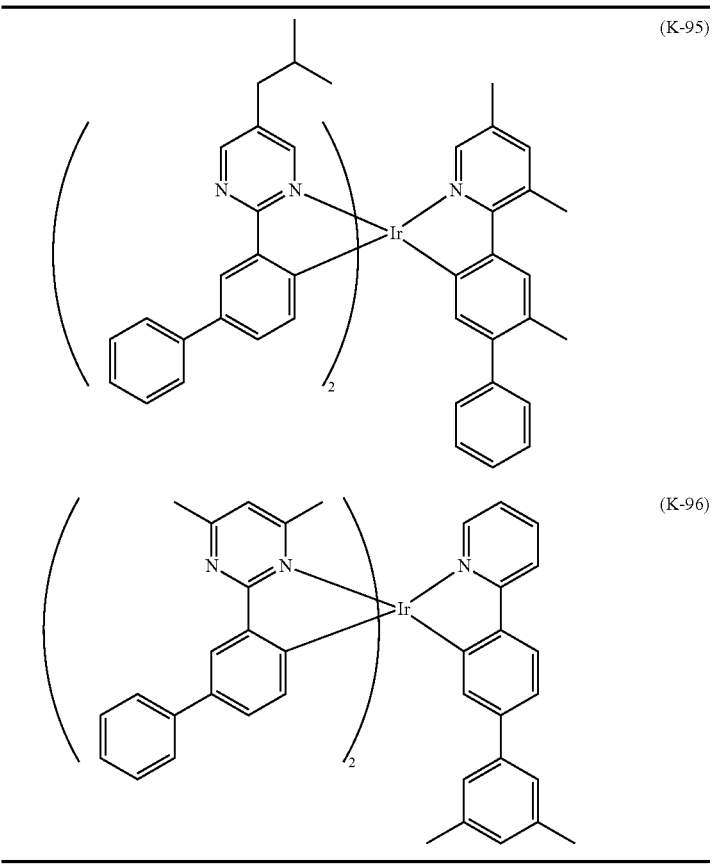
TABLE 5A
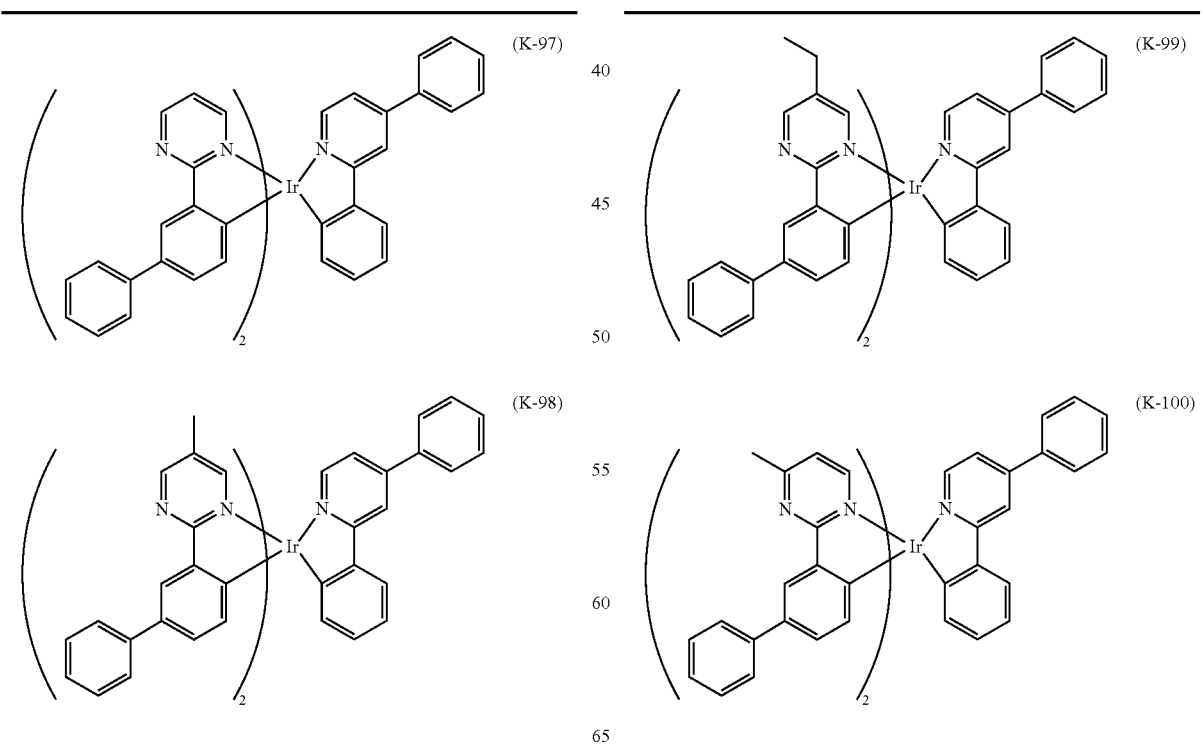

TABLE 5A-continued
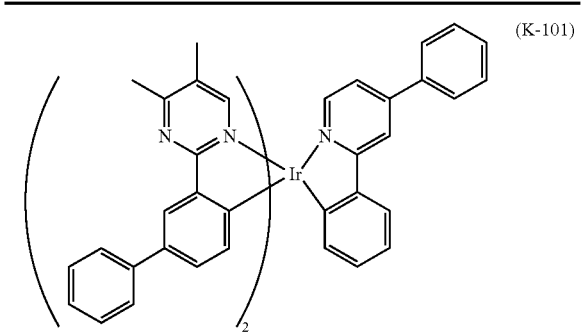
(K-101)
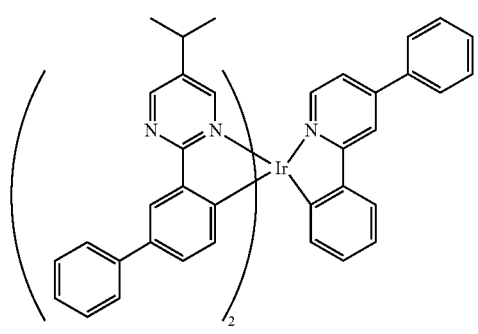
(K-102)
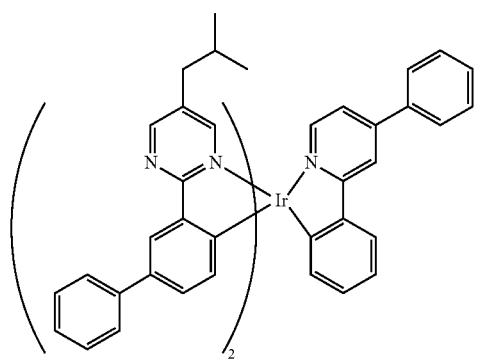
(K-103)
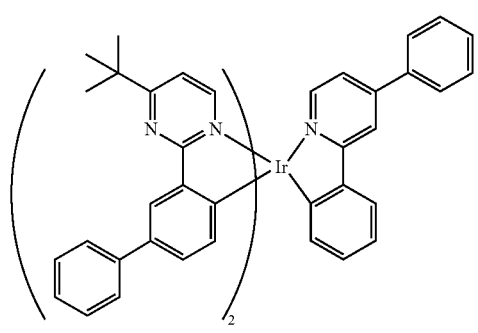
(K-104)
TABLE 5A-continued
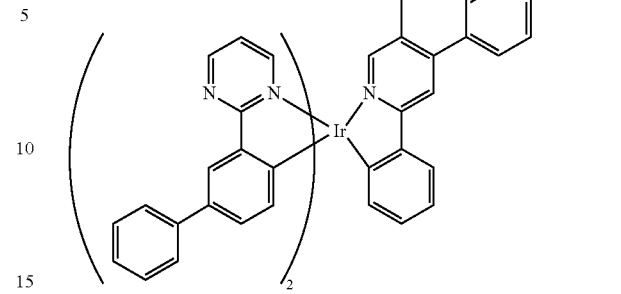
(K-105)
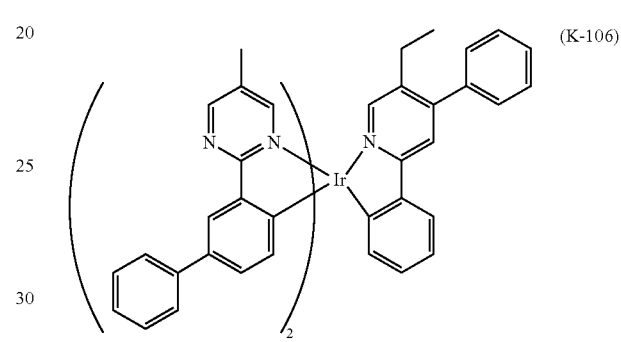
(K-106)
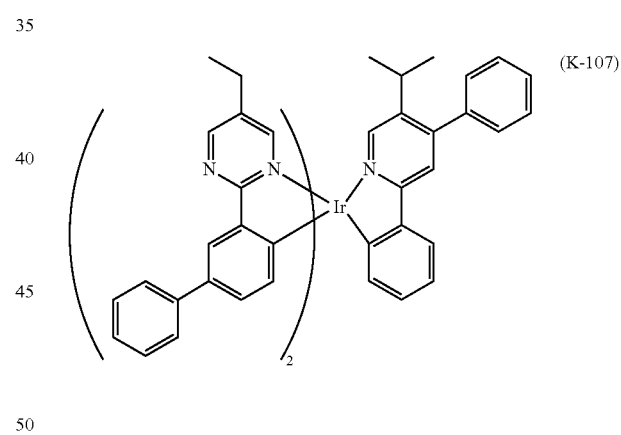
(K-107)
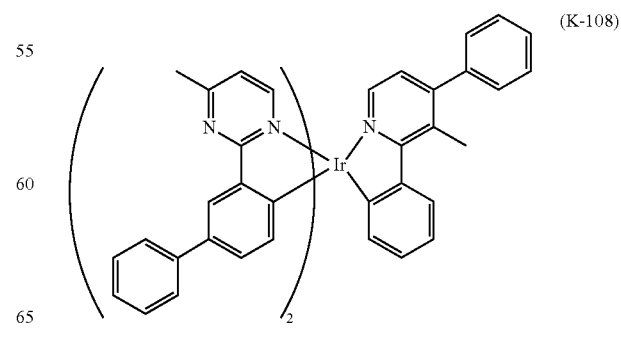
(K-108)

TABLE 5B
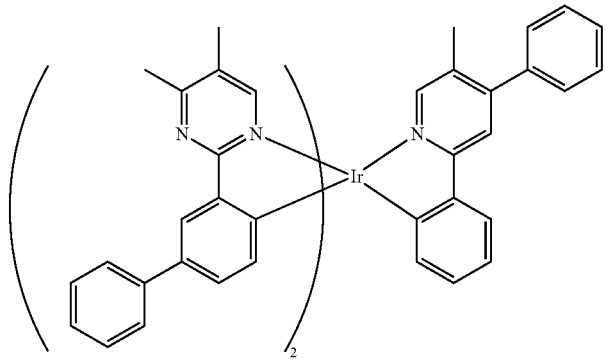
(K-109)
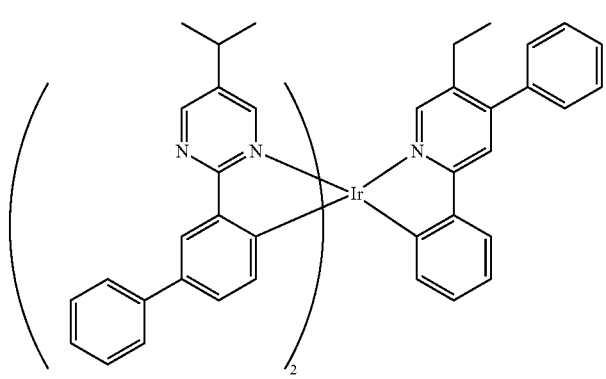
(K-110)
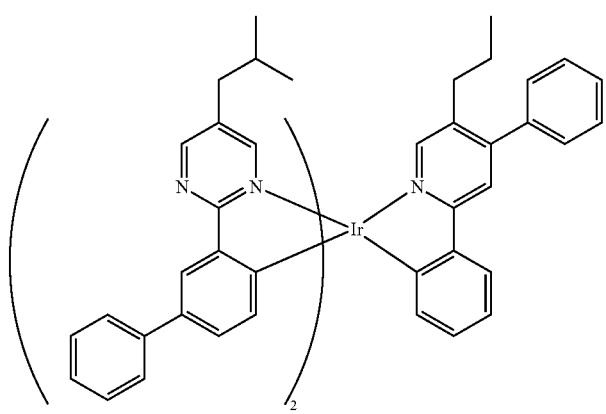
(K-111)
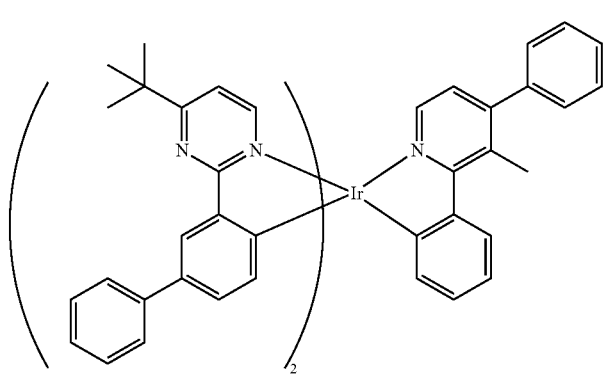
(K-112)

TABLE 5B-continued
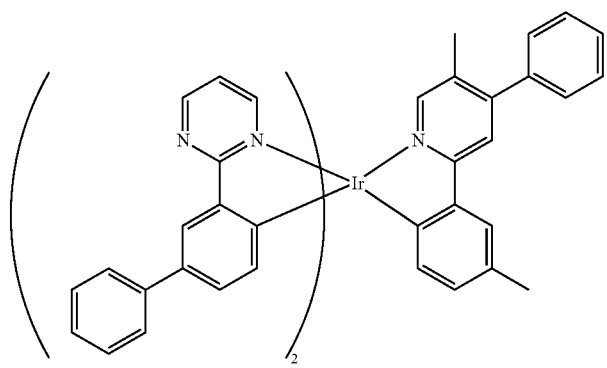
(K-113)
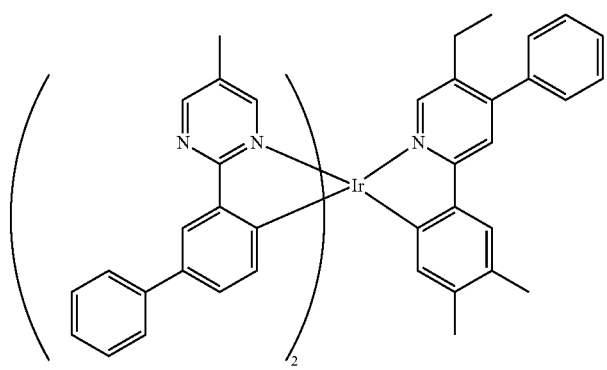
(K-114)
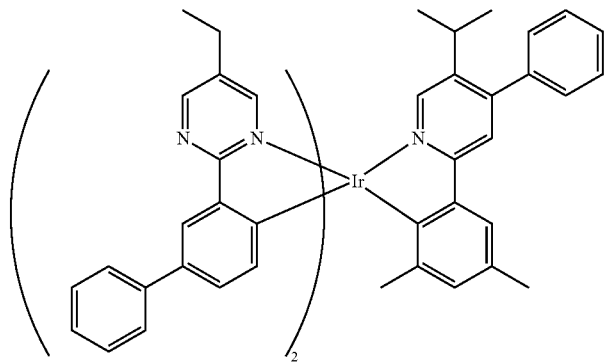
(K-115)
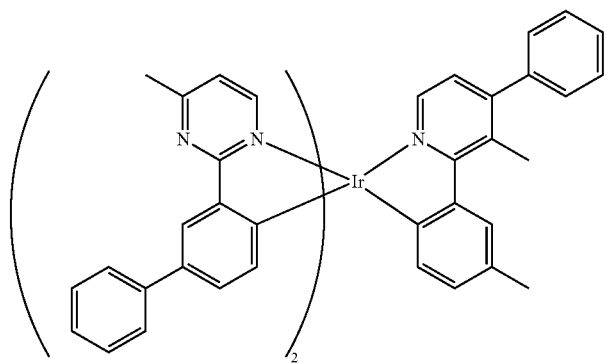
(K-116)

TABLE 5B-continued
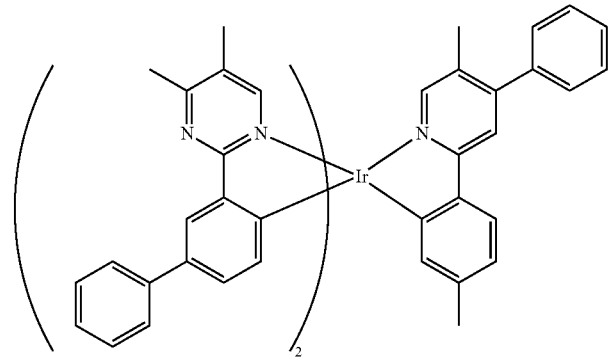
(K-117)
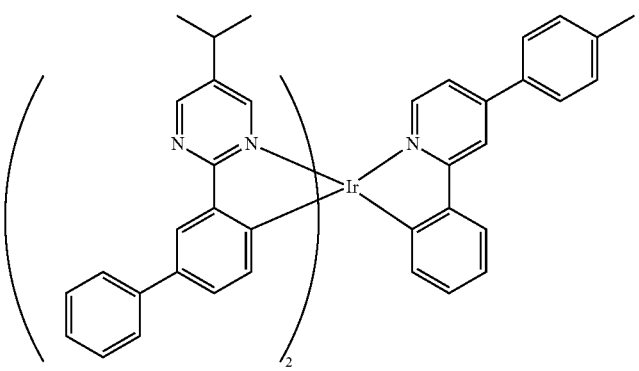
(K-118)
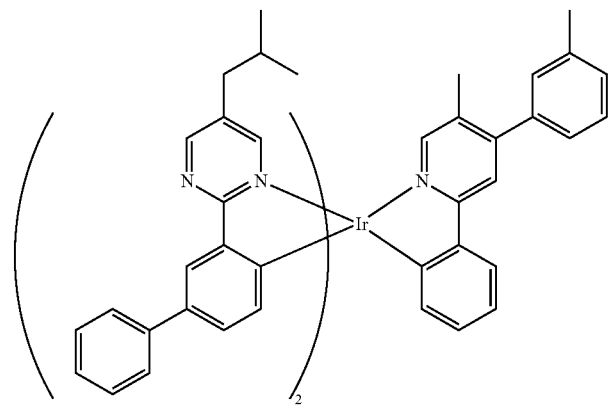
(K-119)
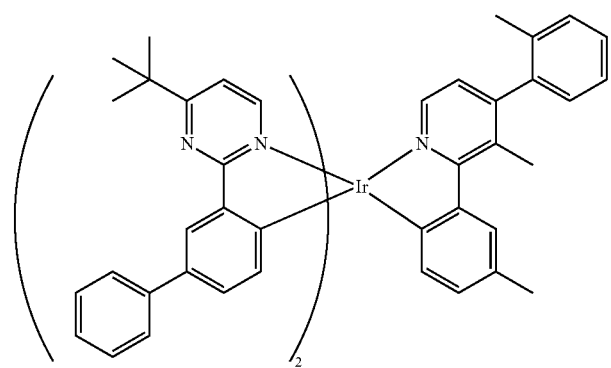
(K-120)

TABLE 6A
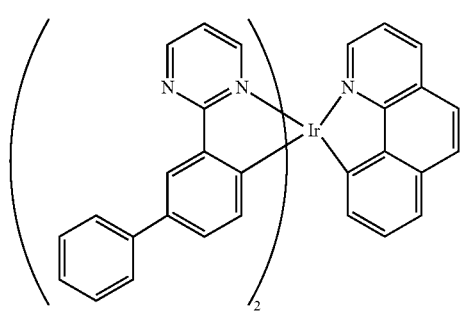 (K-121)
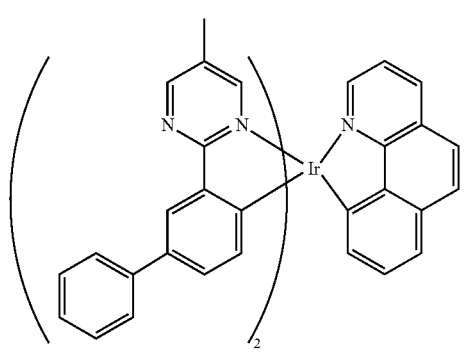 (K-122)
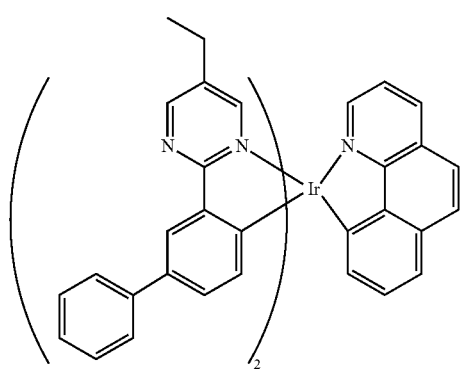 (K-123)
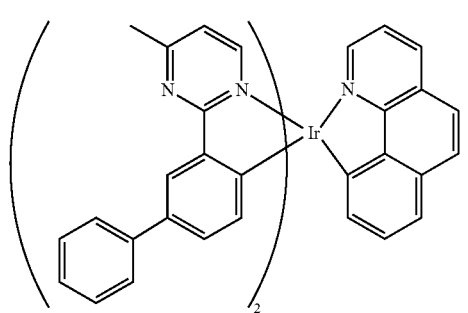 (K-124)
TABLE 6A-continued
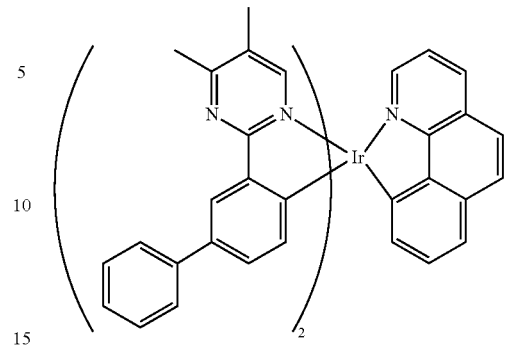 (K-125)
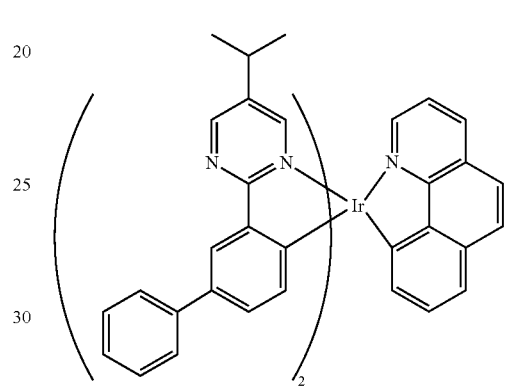 (K-126)
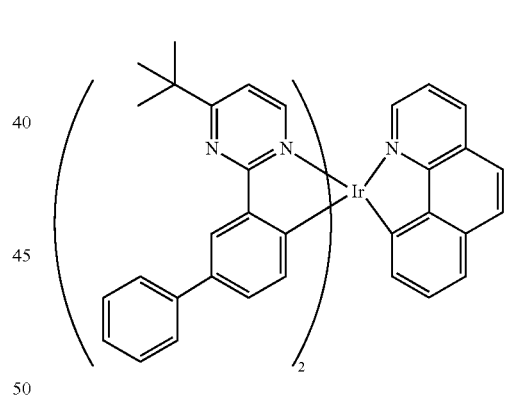 (K-127)
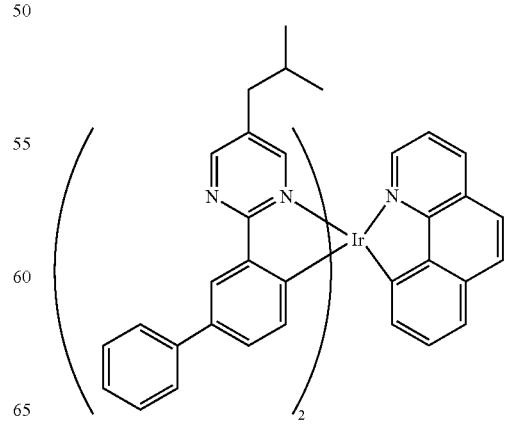 (K-128)

TABLE 6A-continued
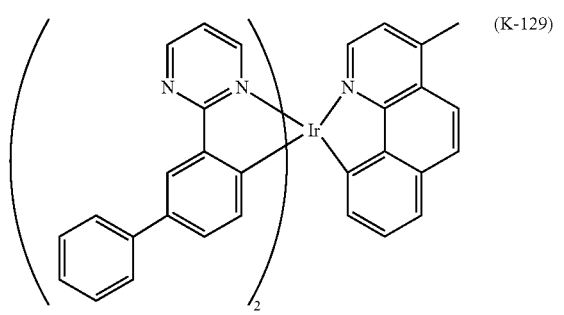
(K-129)
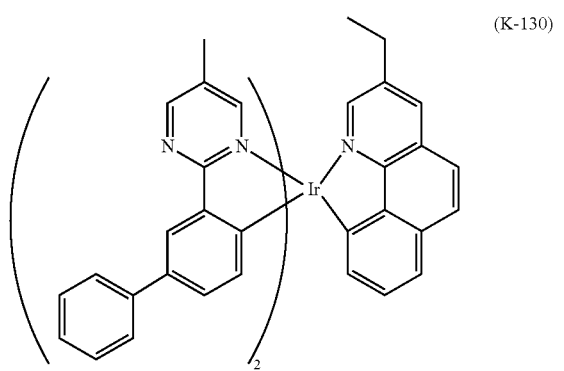
(K-130)
TABLE 6A-continued
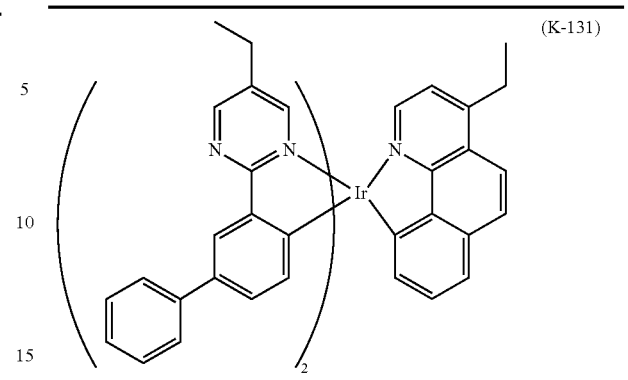
(K-131)
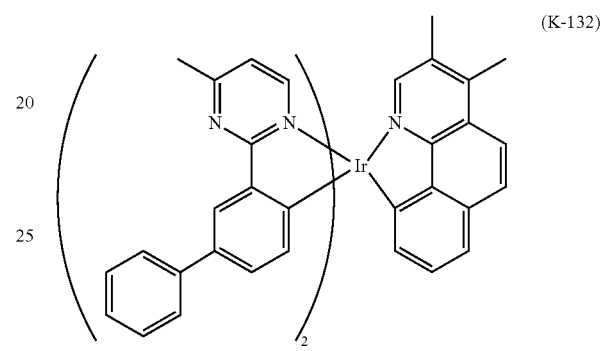
(K-132)
TABLE 6B
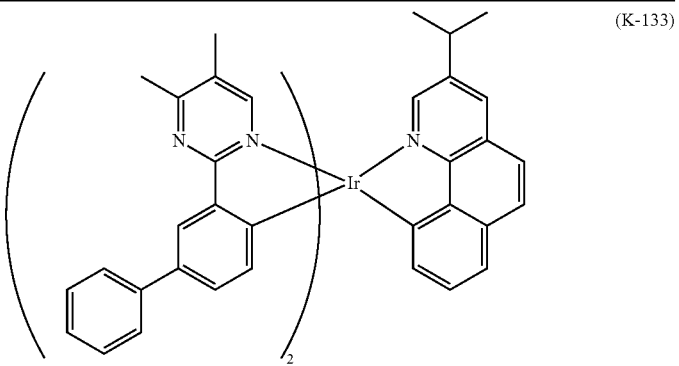
(K-133)
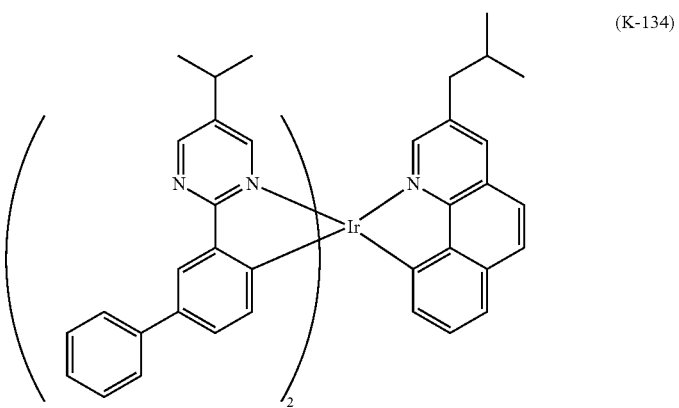
(K-134)

TABLE 6B-continued
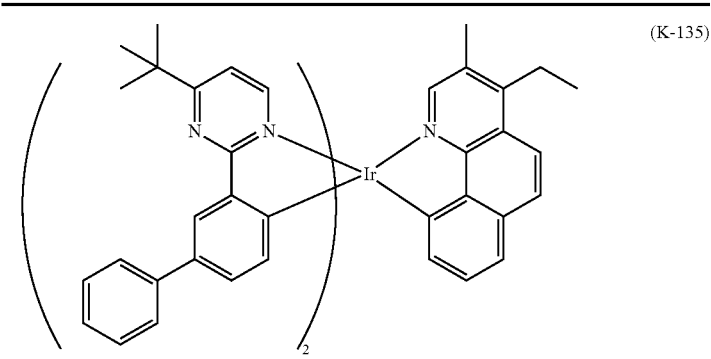
(K-135)
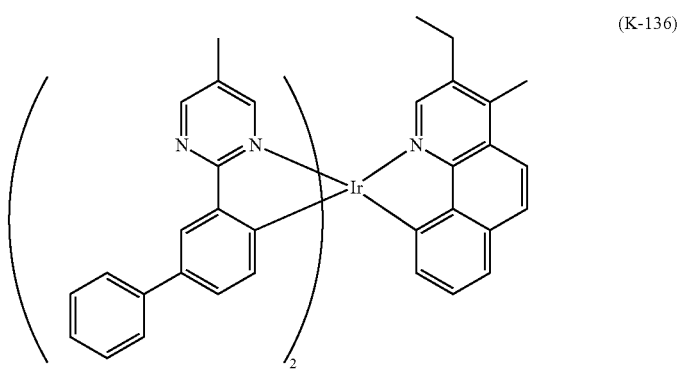
(K-136)
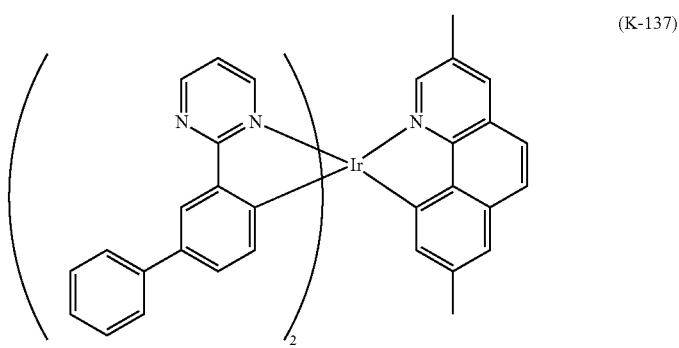
(K-137)
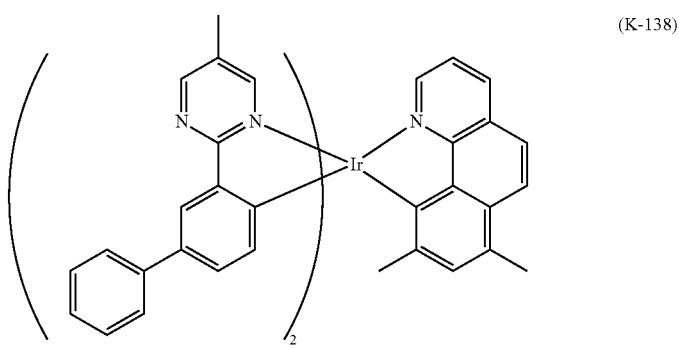
(K-138)

TABLE 6B-continued
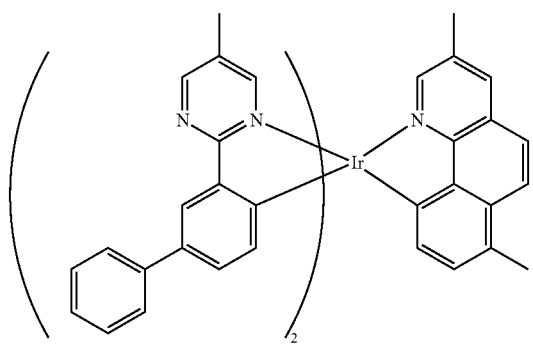
(K-139)
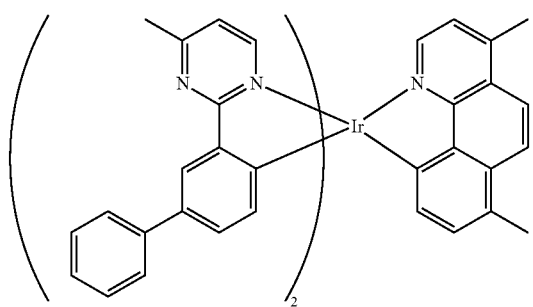
(K-140)
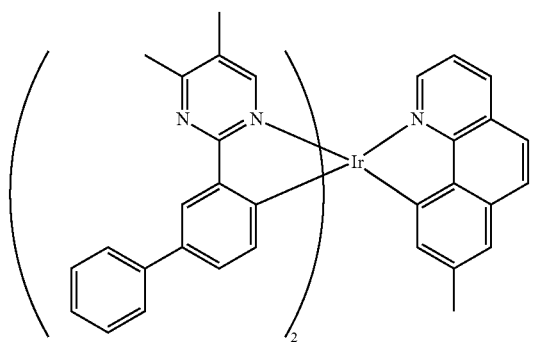
(K-141)
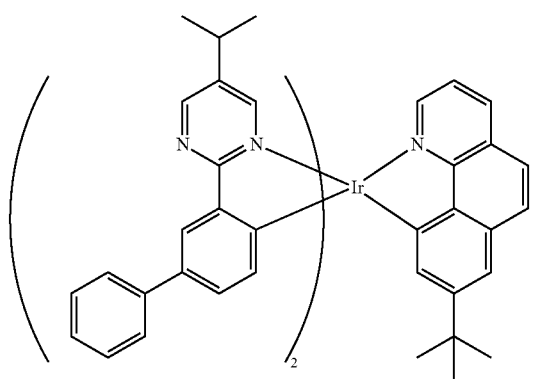
(K-142)

TABLE 6B-continued
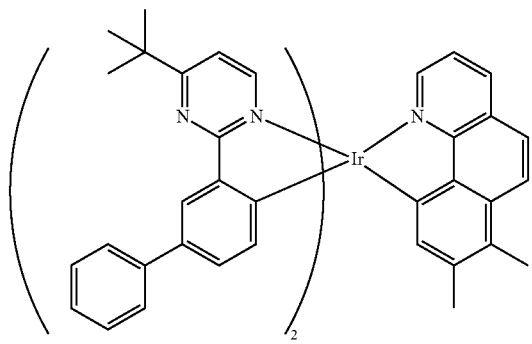
(K-143)
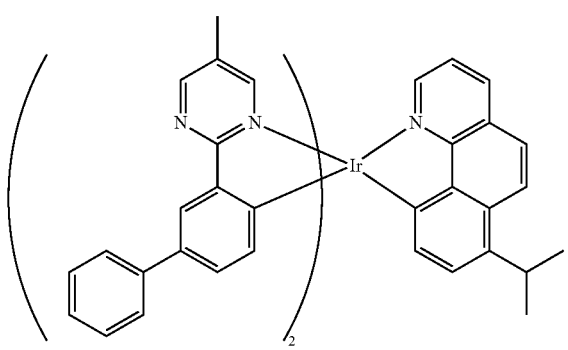
(K-144)
TABLE 7A
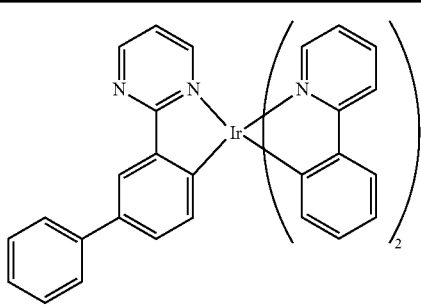
(K-145)
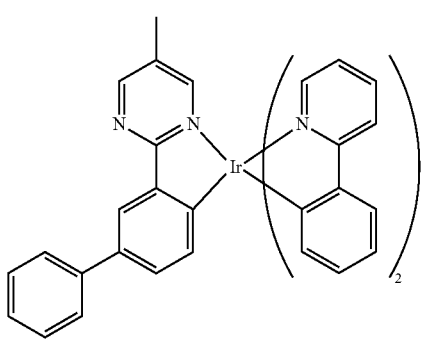
(K-146)
TABLE 7A-continued
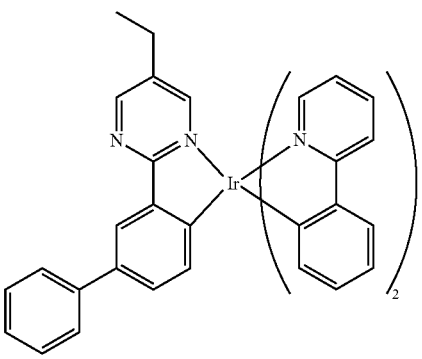
(K-147)
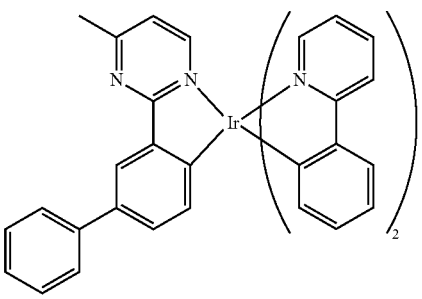
(K-148)

TABLE 7A-continued
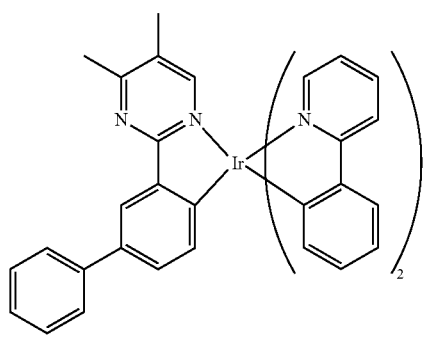
(K-149)
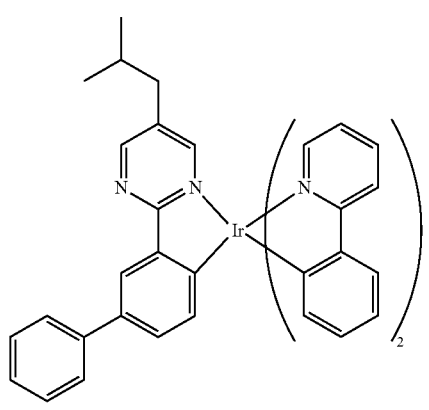
(K-150)
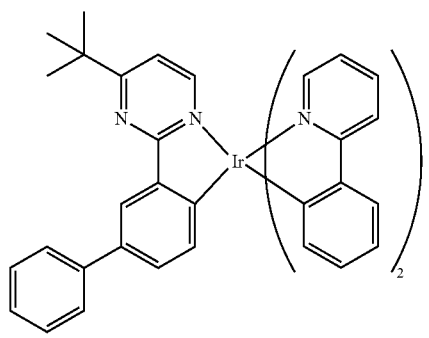
(K-151)
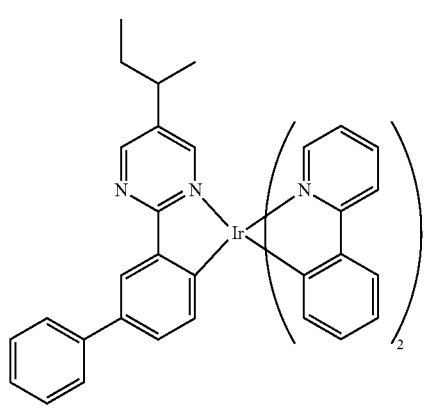
(K-152)
TABLE 7A-continued
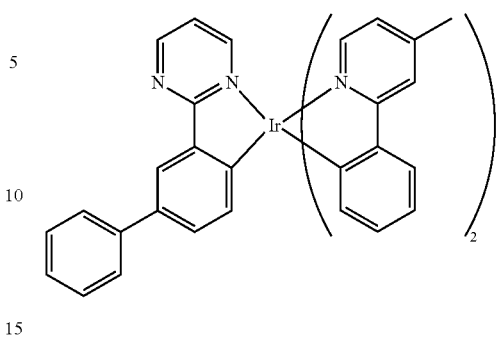
(K-153)
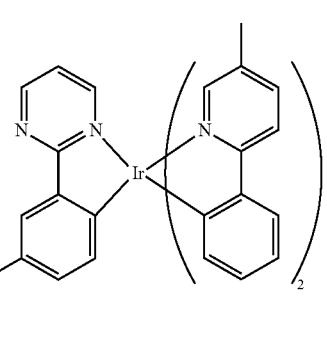
(K-154)
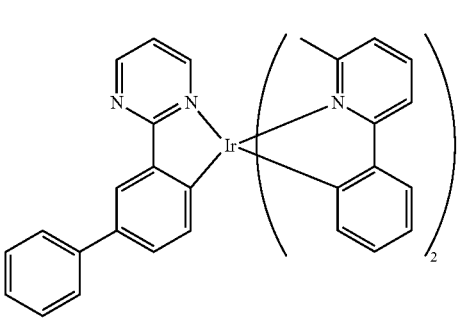
(K-155)
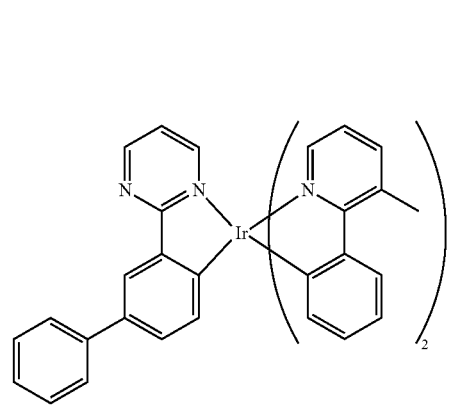
(K-156)

TABLE 7B
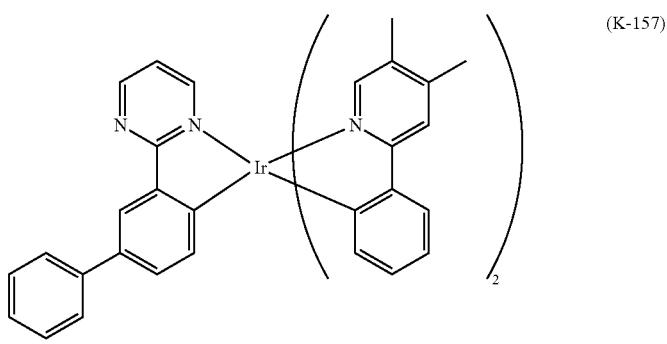
(K-157)
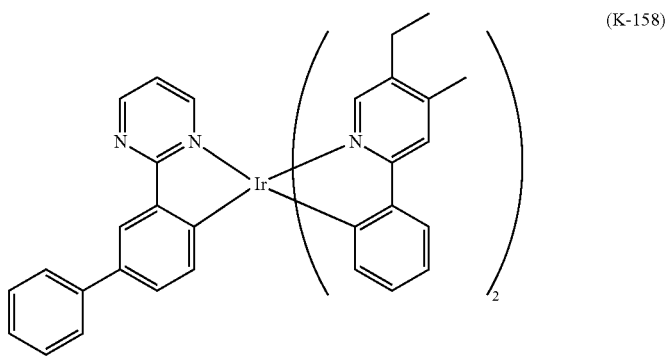
(K-158)
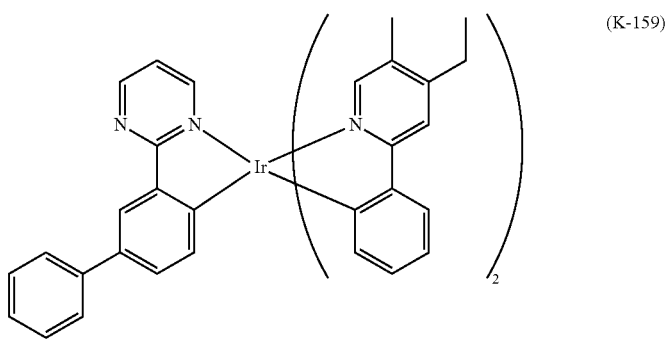
(K-159)
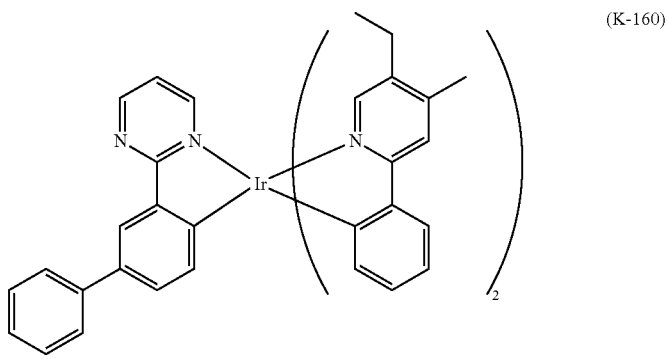
(K-160)

TABLE 7B-continued
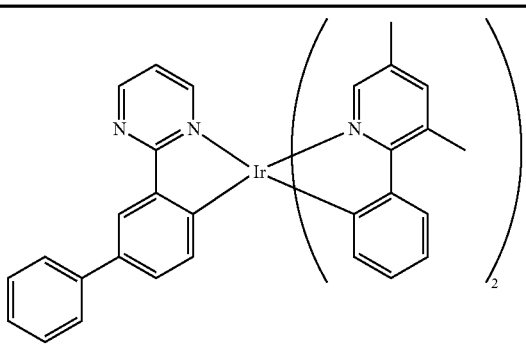
(K-161)
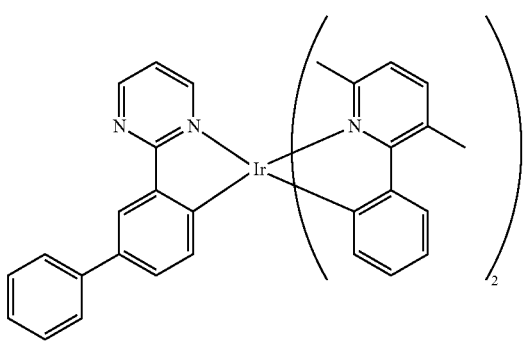
(K-162)
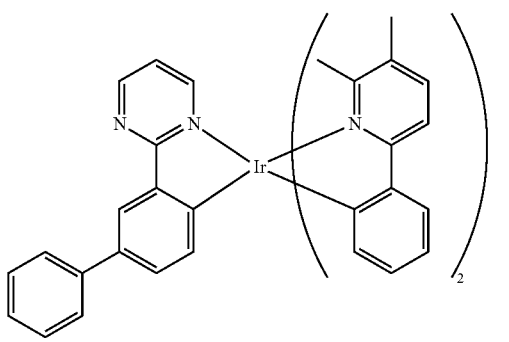
(K-163)
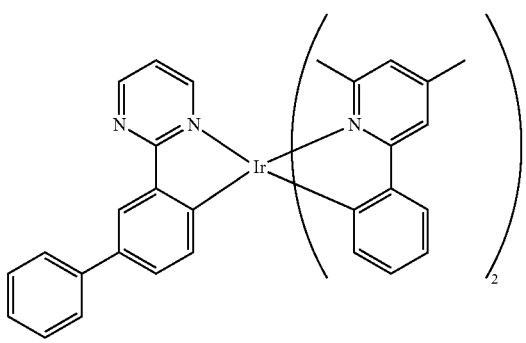
(K-164)
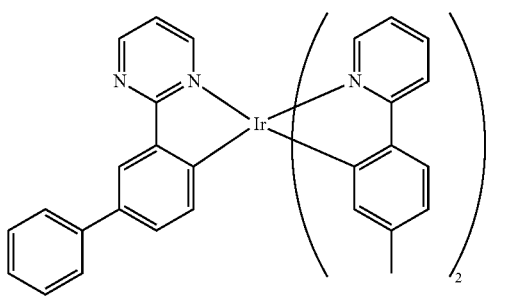
(K-165)

TABLE 7B-continued
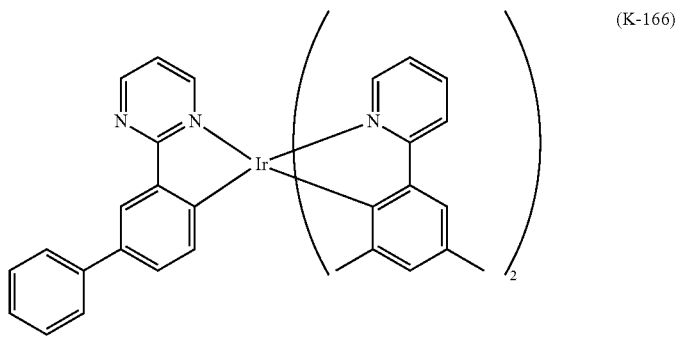
(K-166)
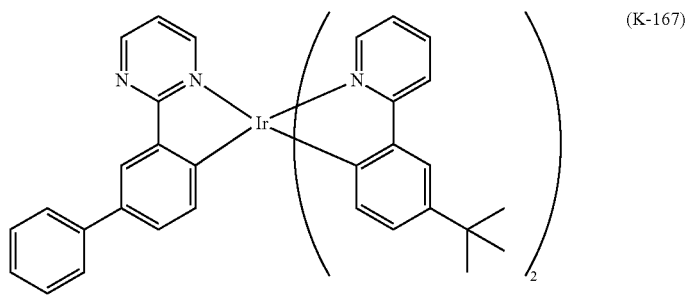
(K-167)
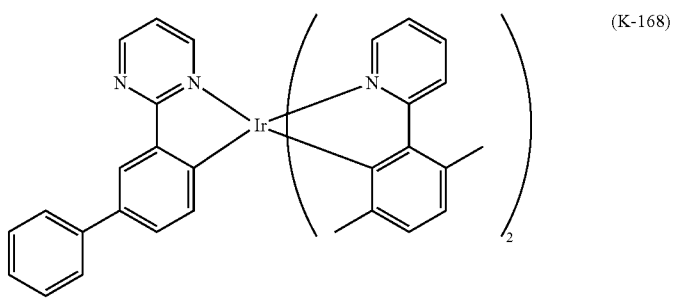
(K-168)
TABLE 8A
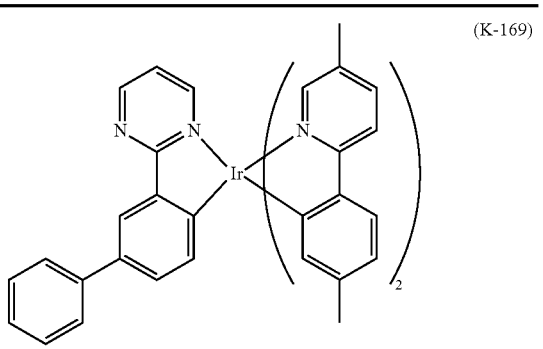
(K-169)
TABLE 8A-continued
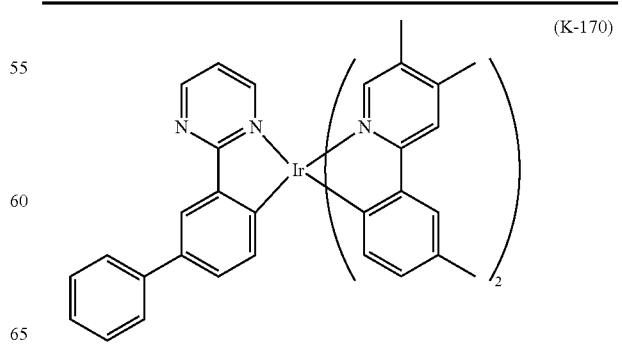
(K-170)

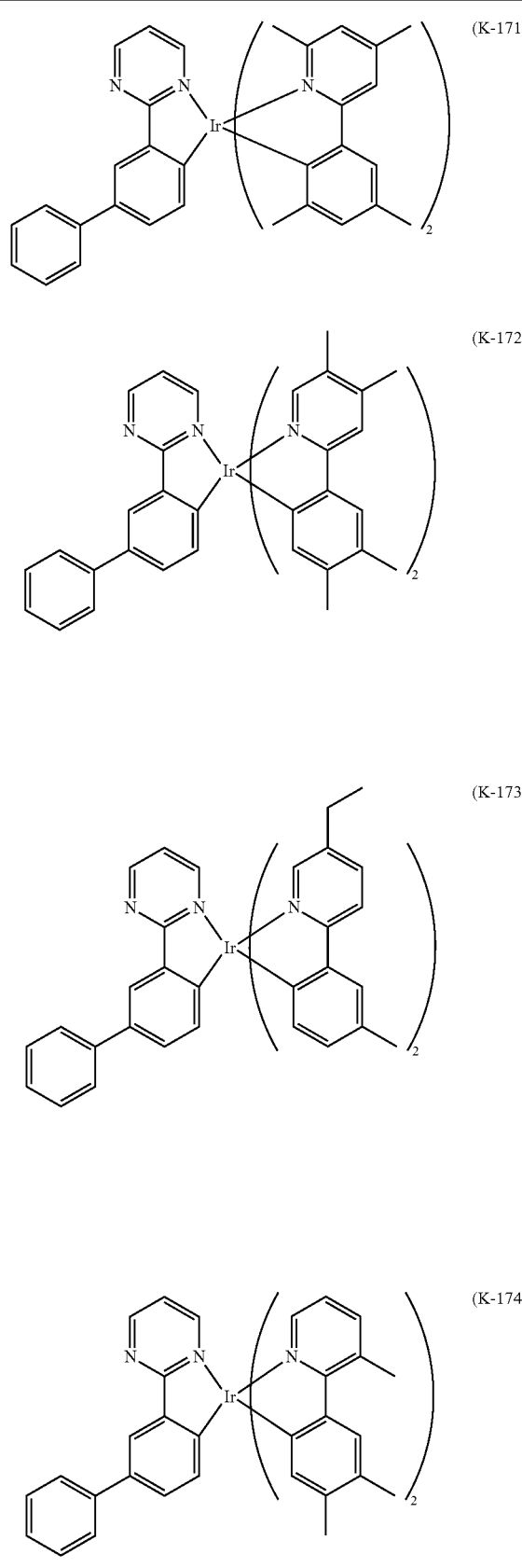

TABLE 8A-continued
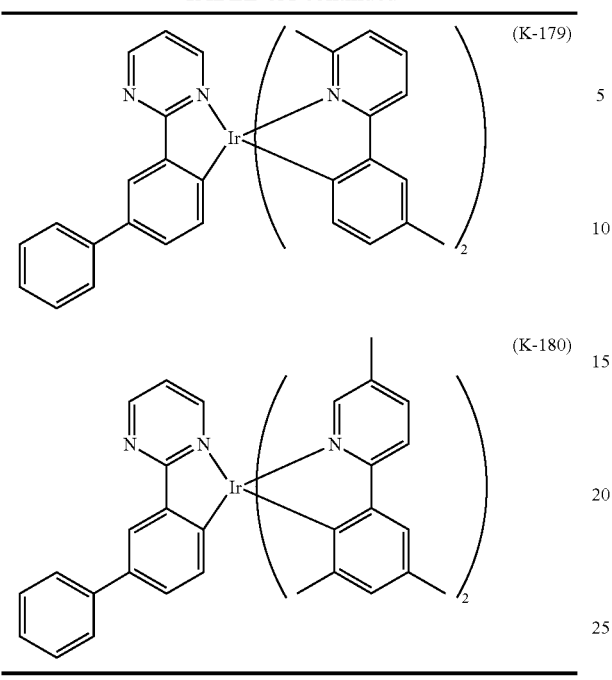
(K-179)
(K-180)
TABLE 8B
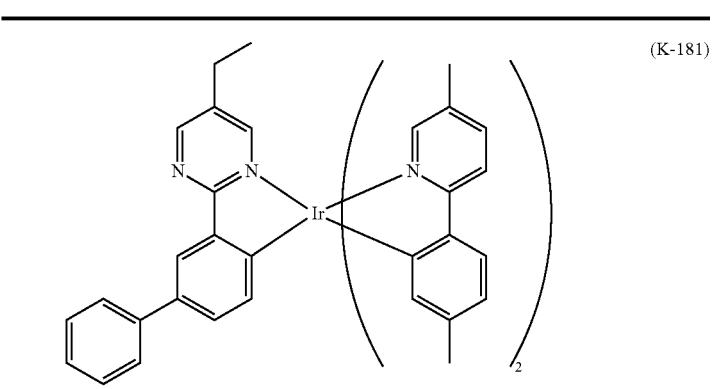
(K-181)
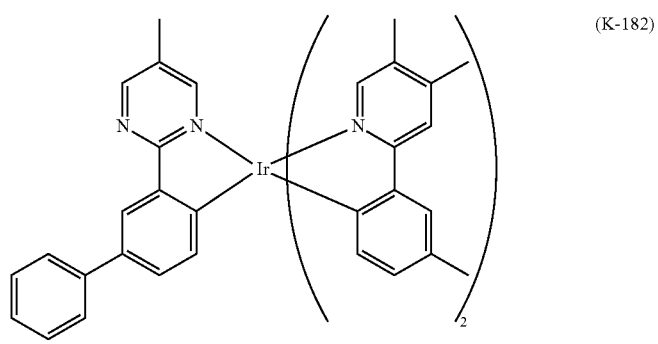
(K-182)

TABLE 8B-continued
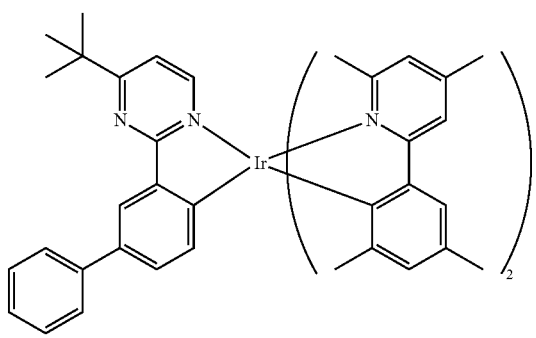
(K-183)
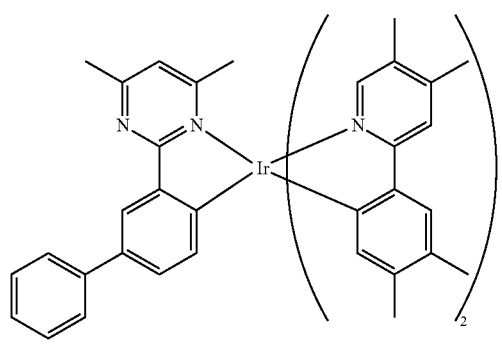
(K-184)
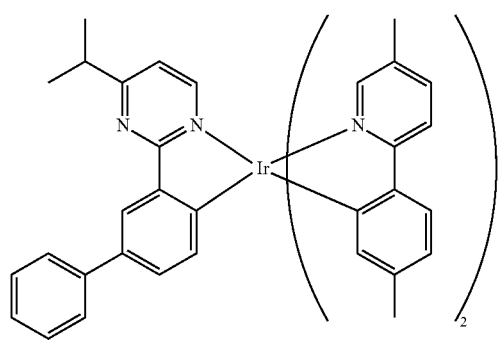
(K-185)
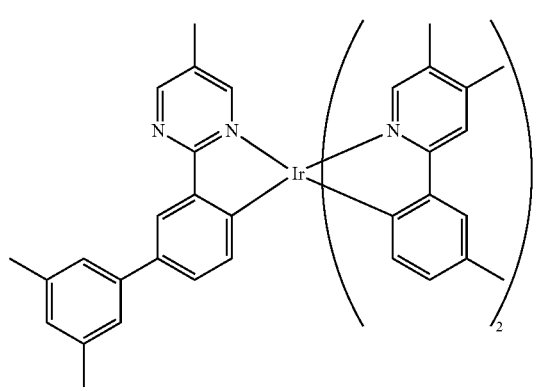
(K-186)

TABLE 8B-continued
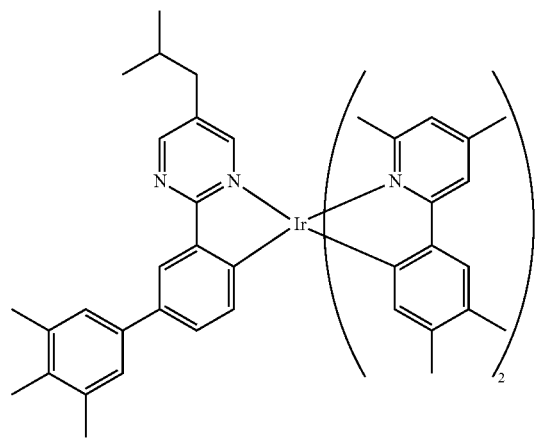
(K-187)
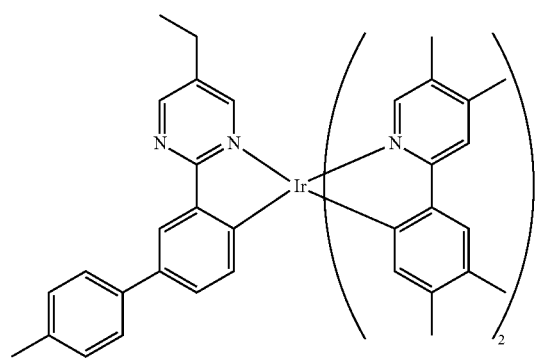
(K-188)
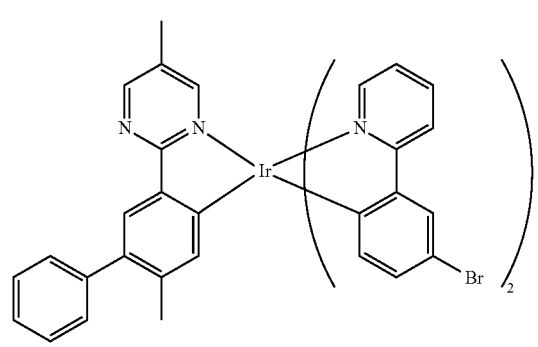
(K-189)
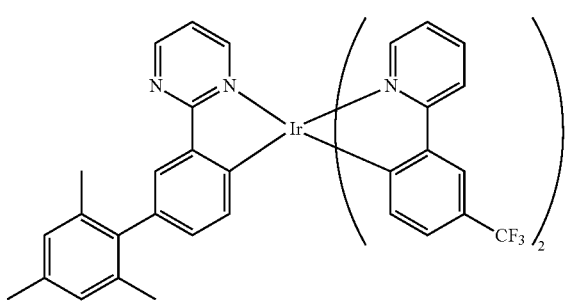
(K-190)

TABLE 8B-continued
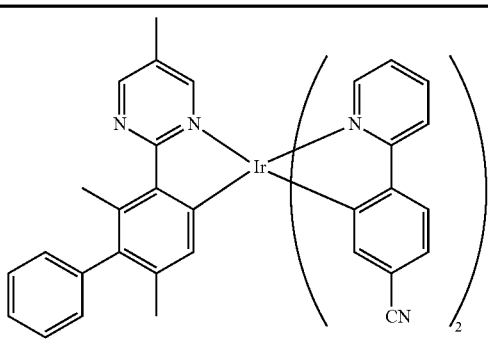
(K-191)
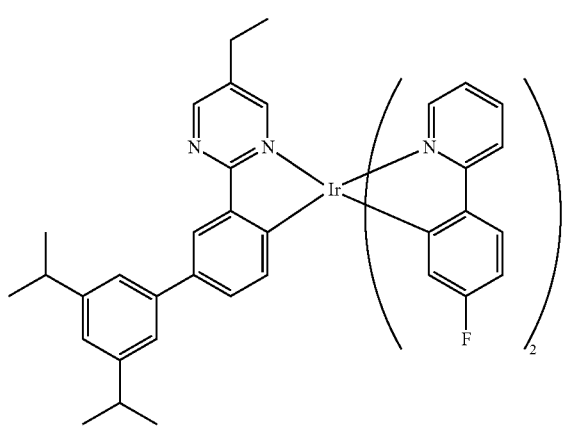
(K-192)
| TABLE 9A | TABLE 9A-continued |
|---|---|
| 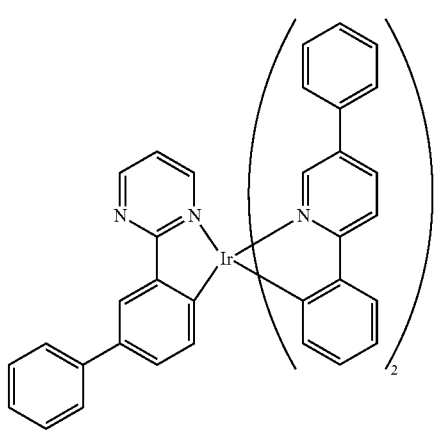 (K-193) | 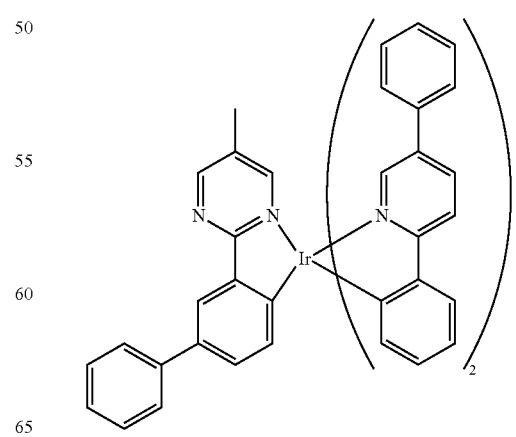 (K-194) |

TABLE 9A-continued
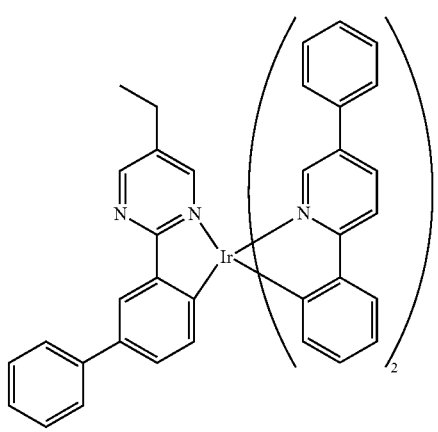 (K-195)
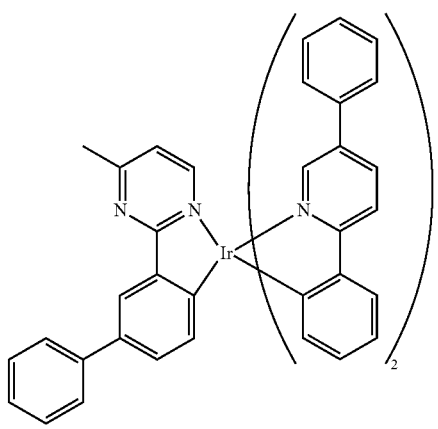 (K-196)
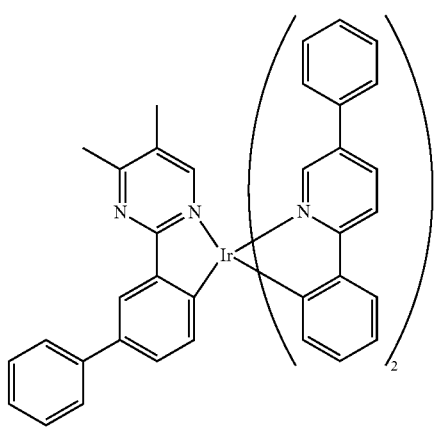 (K-197)
TABLE 9A-continued
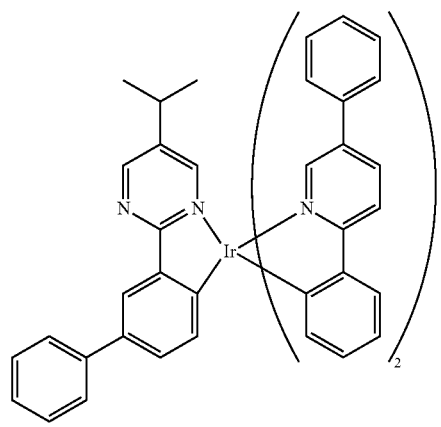 (K-198)
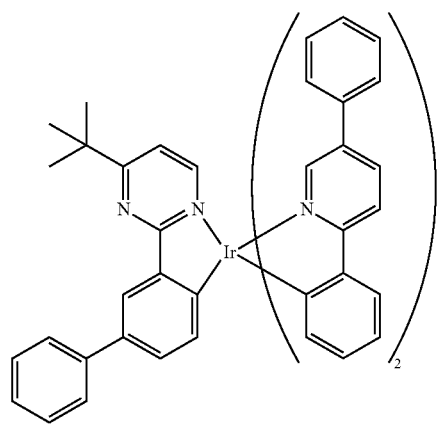 (K-199)
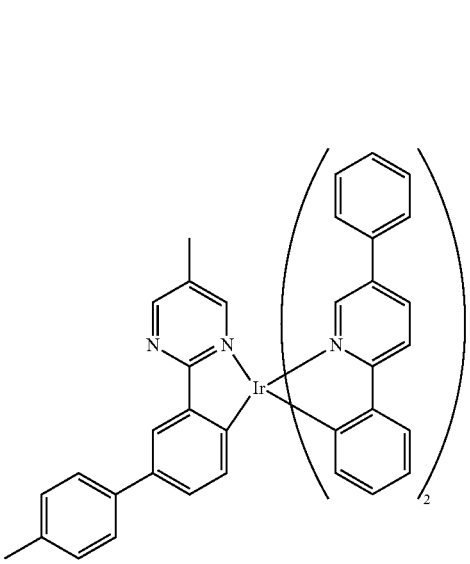 (K-200)

TABLE 9A-continued
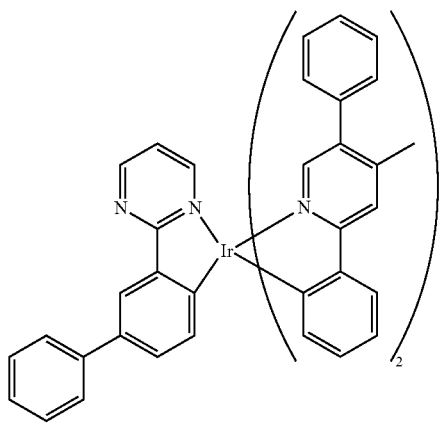
(K-201)
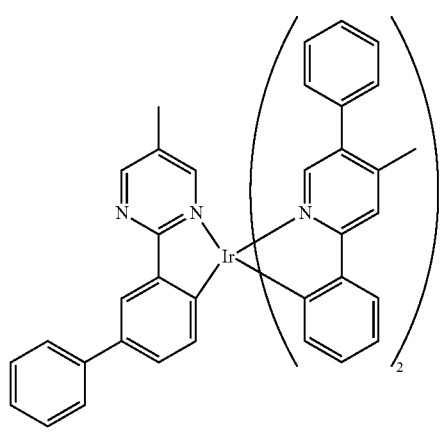
(K-202)
TABLE 9A-continued
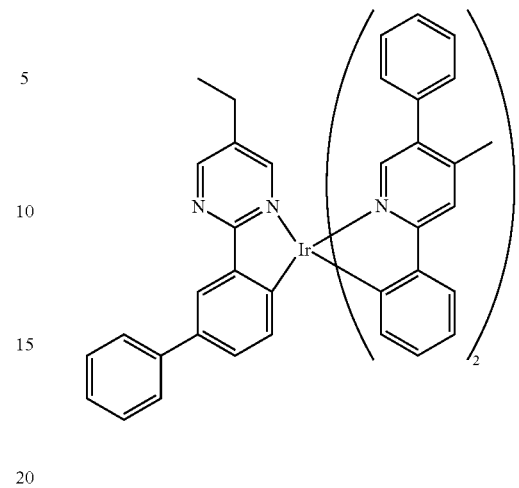
(K-203)
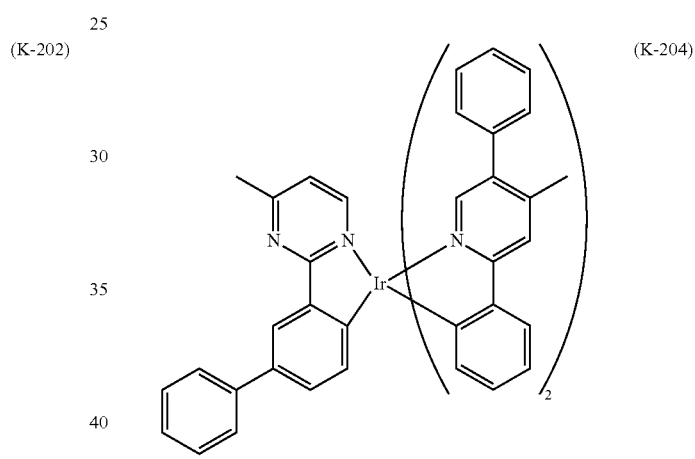
(K-204)
TABLE 9B
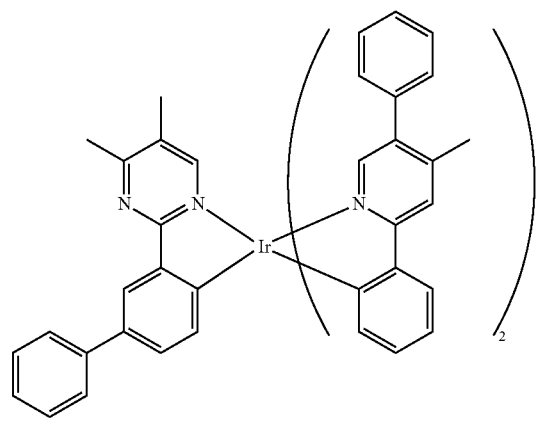
(K-205)

TABLE 9B-continued
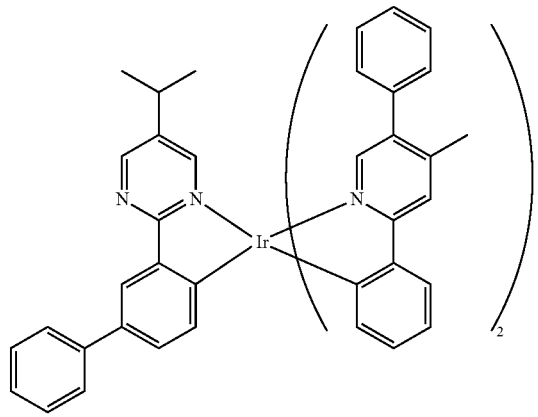
(K-206)
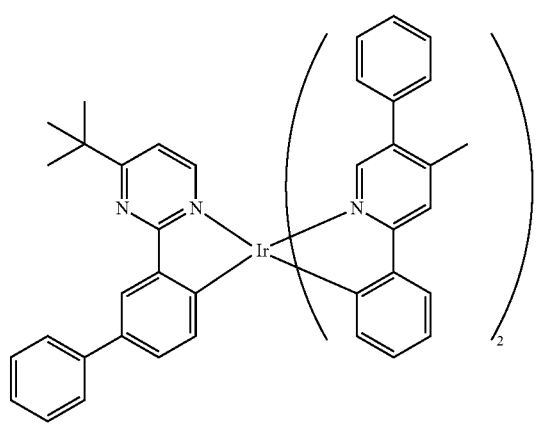
(K-207)
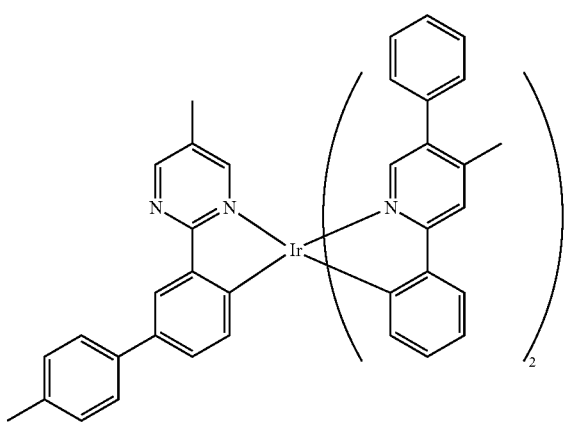
(K-208)

TABLE 9B-continued
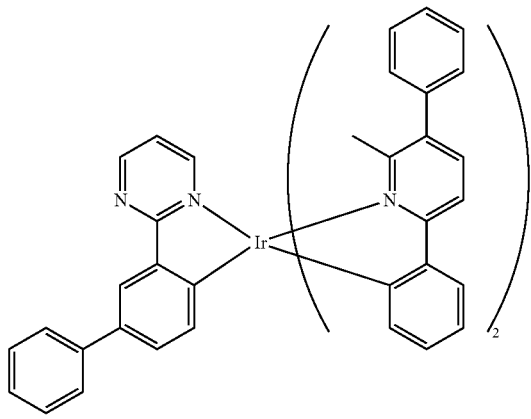
(K-209)
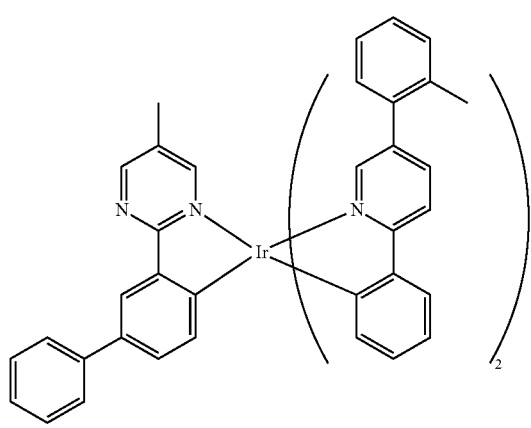
(K-210)
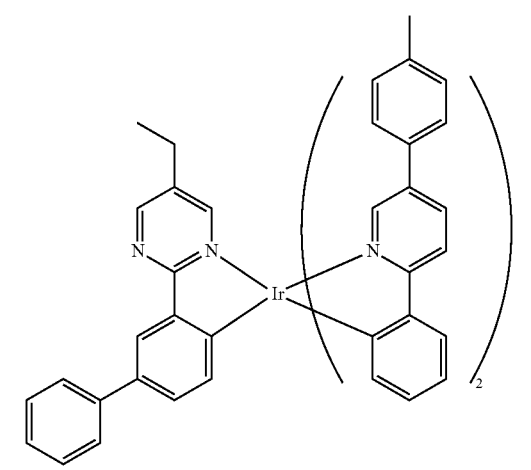
(K-211)

TABLE 9B-continued
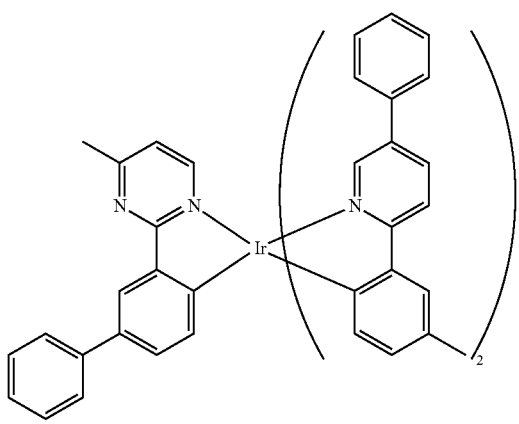
(K-212)
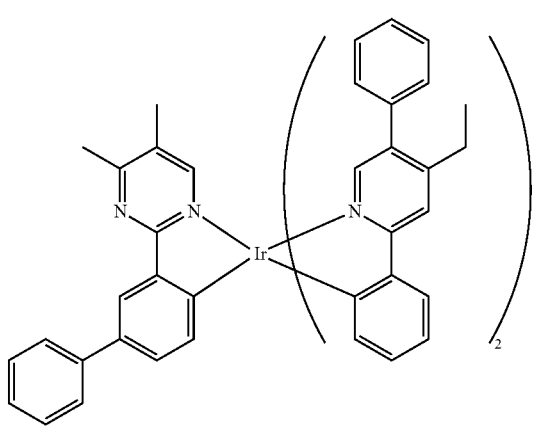
(K-213)
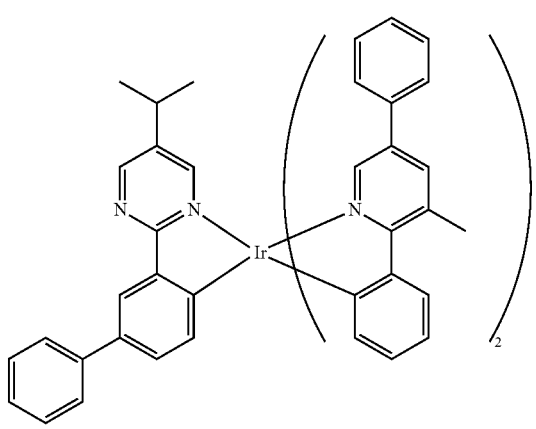
(K-214)

TABLE 9B-continued
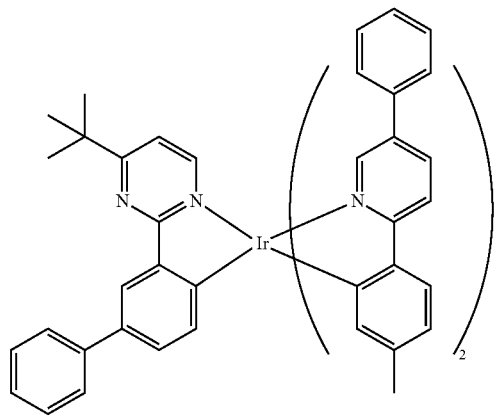
(K-215)
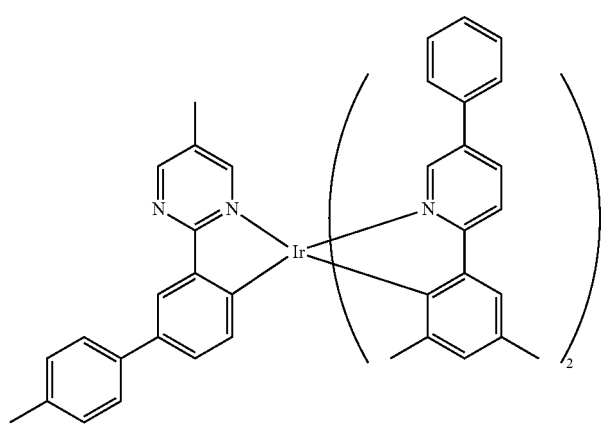
(K-216)
| TABLE 10A | TABLE 10A-continued |
|---|---|
| 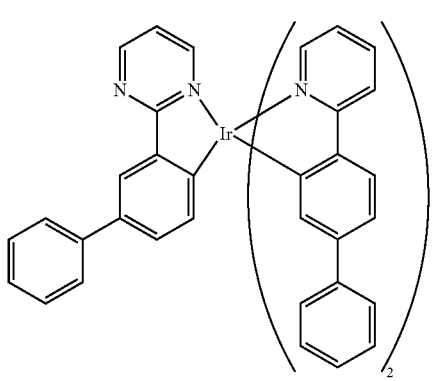 (K-217) | 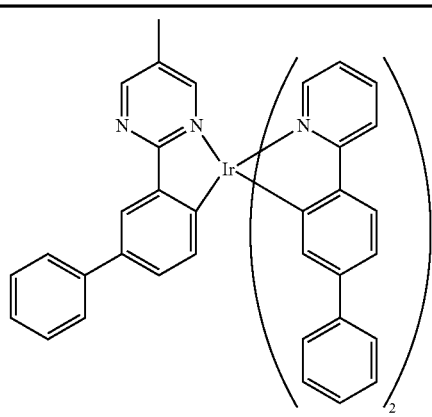 (K-218) |

TABLE 10A-continued (K-219)

(K-220)

(K-221)

TABLE 10A-continued (K-222)

(K-223)

(K-224)

TABLE 10A-continued
(K-225) 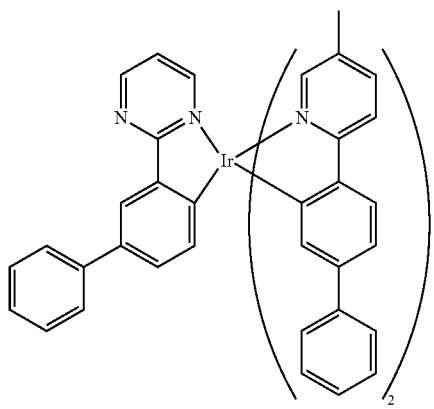
(K-227) 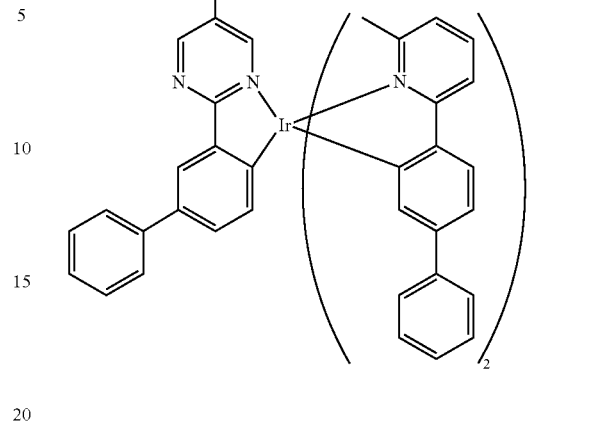
(K-226) 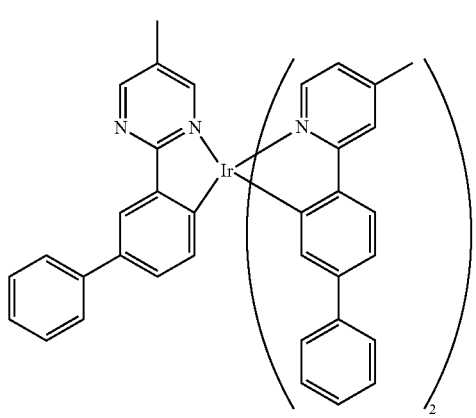
(K-228) 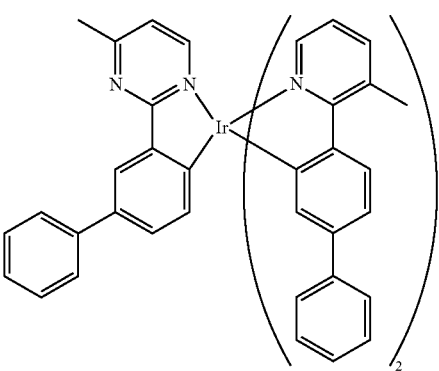
TABLE 10B
(K-229) 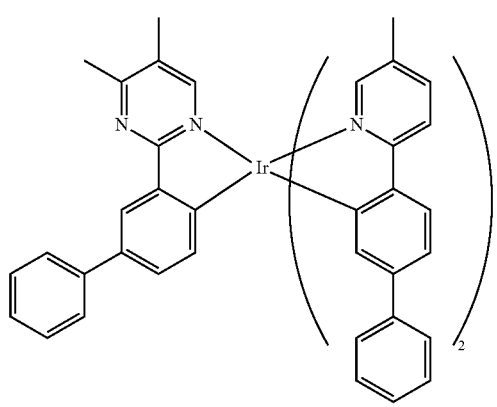

TABLE 10B-continued
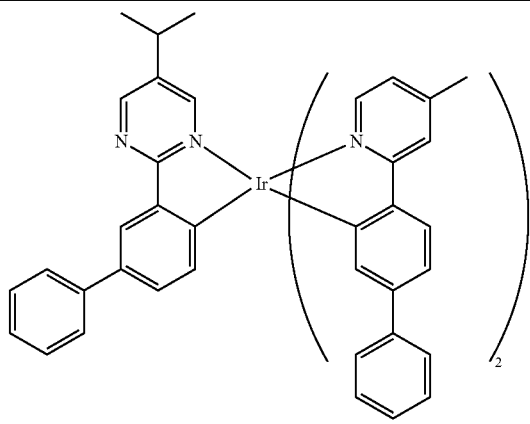
(K-230)
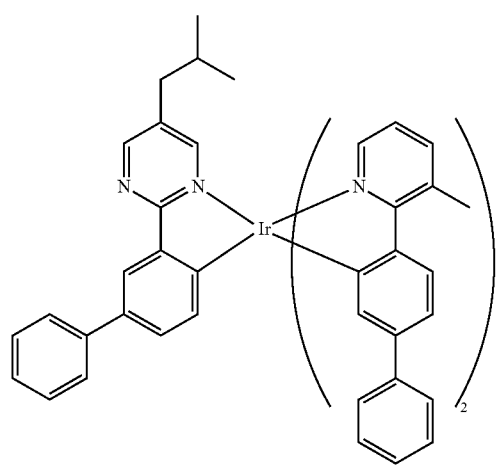
(K-231)
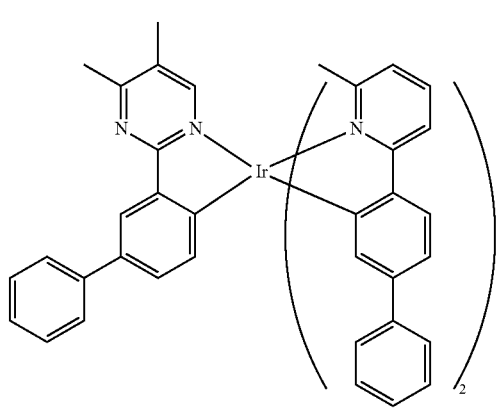
(K-232)

TABLE 10B-continued
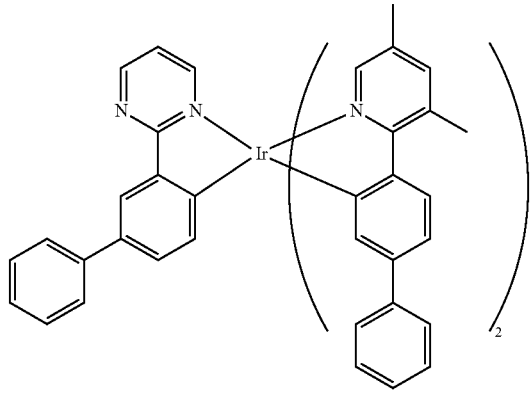
(K-233)
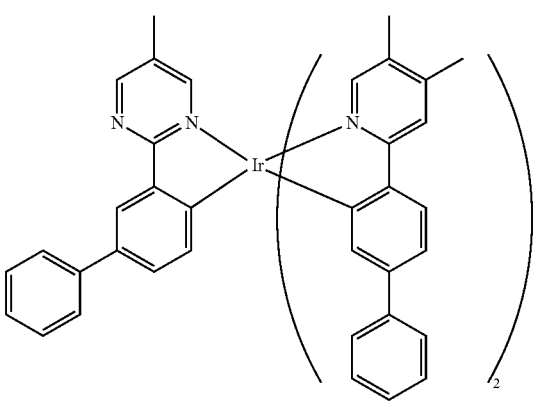
(K-234)
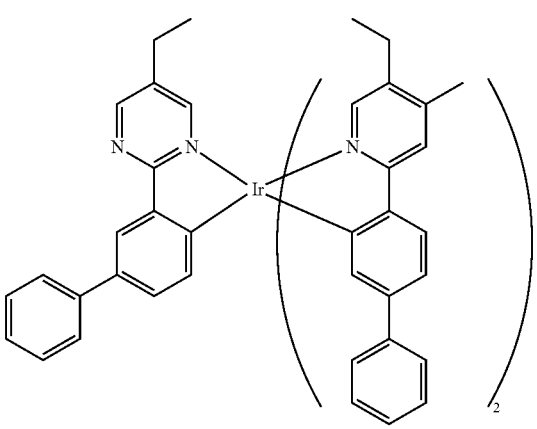
(K-235)
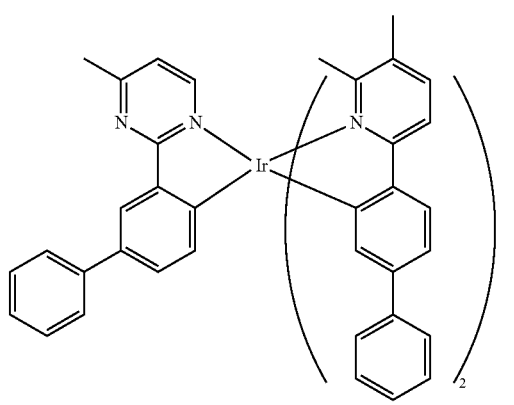
(K-236)

TABLE 10B-continued
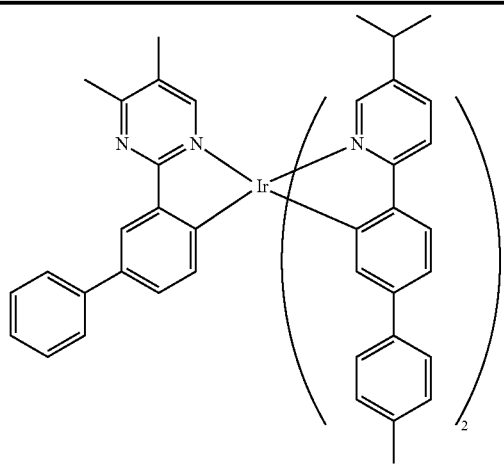
(K-237)
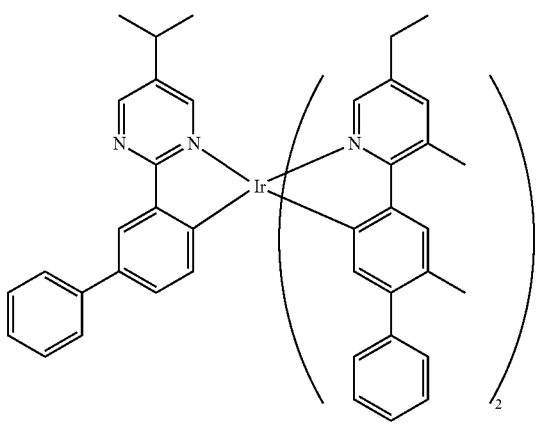
(K-238)
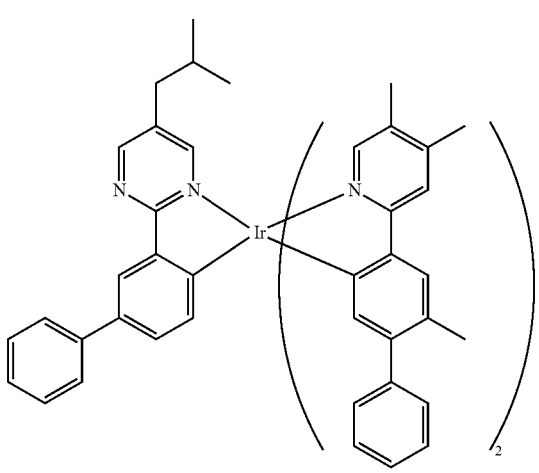
(K-239)

TABLE 10B-continued
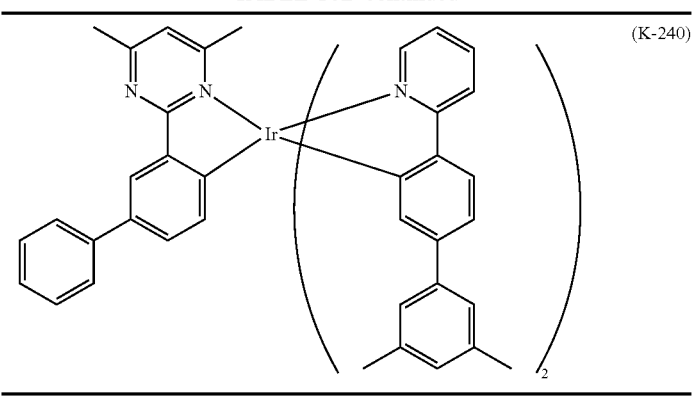
(K-240)
TABLE 11A
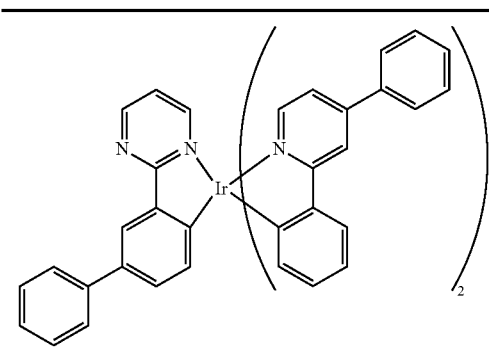
(K-241)
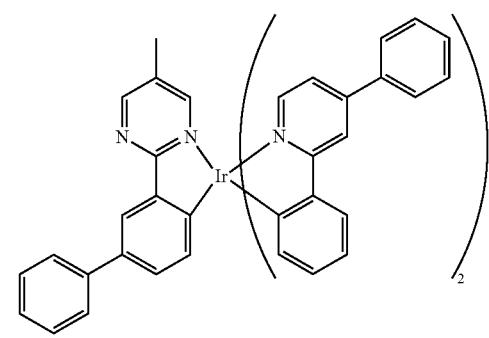
(K-242)
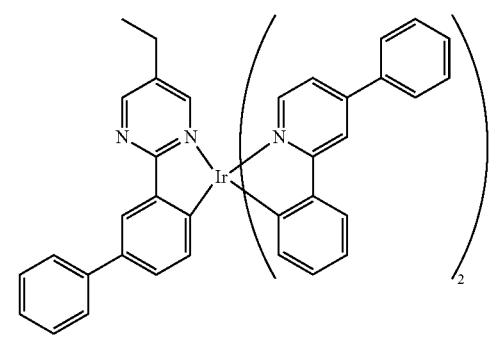
(K-243)
TABLE 11A-continued
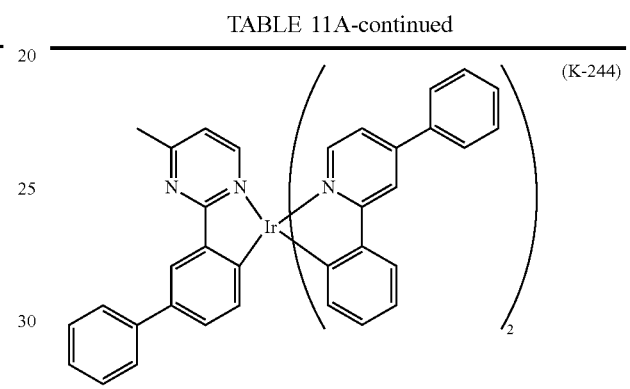
(K-244)
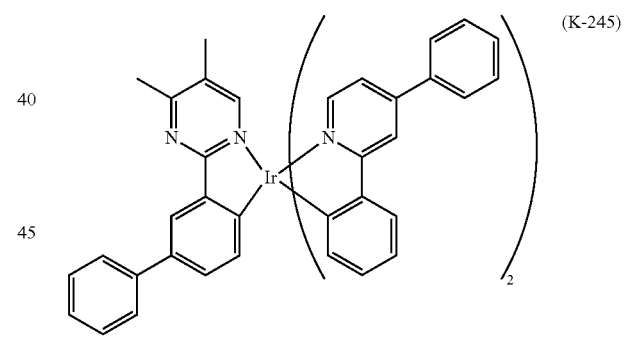
(K-245)
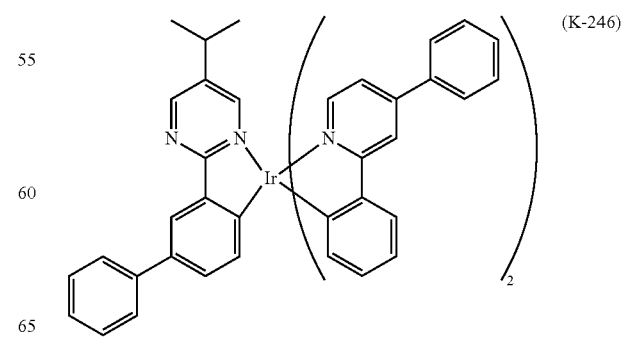
(K-246)

TABLE 11A-continued
(K-247)
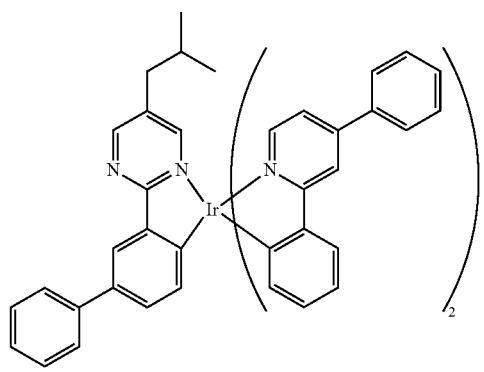
(K-250)
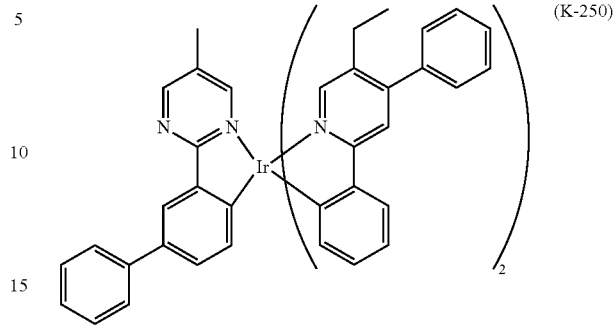
(K-248)
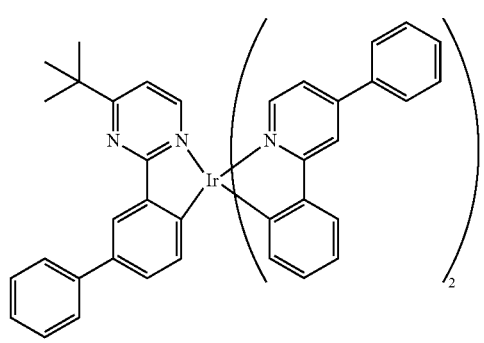
(K-251)
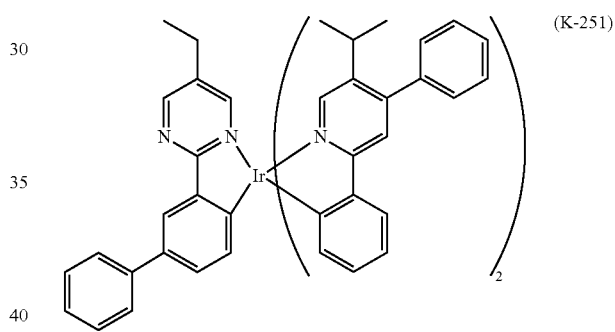
(K-249)
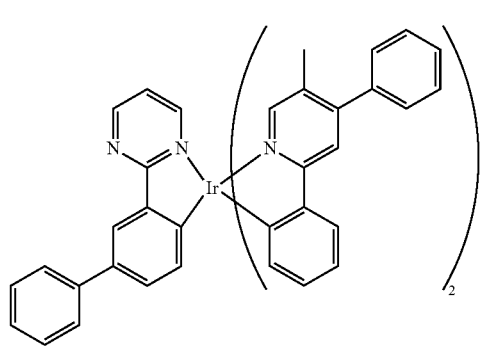
(K-252)
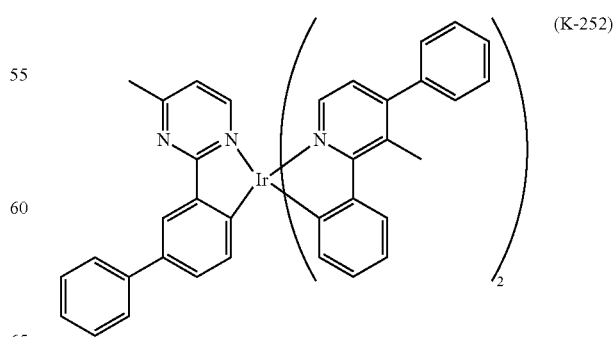

TABLE 11B
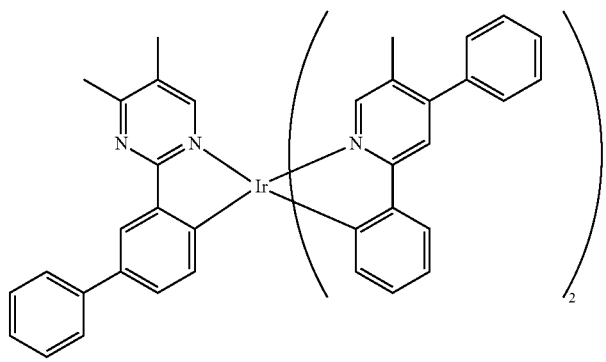
(K-253)
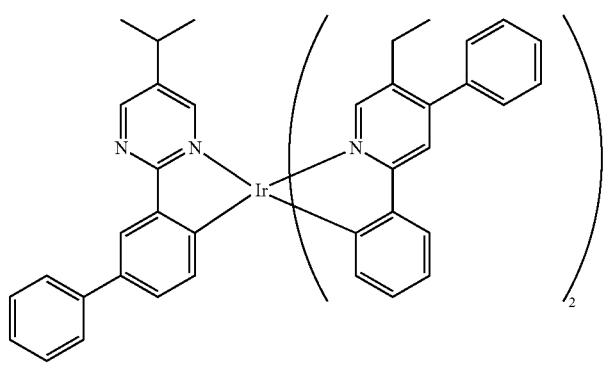
(K-254)
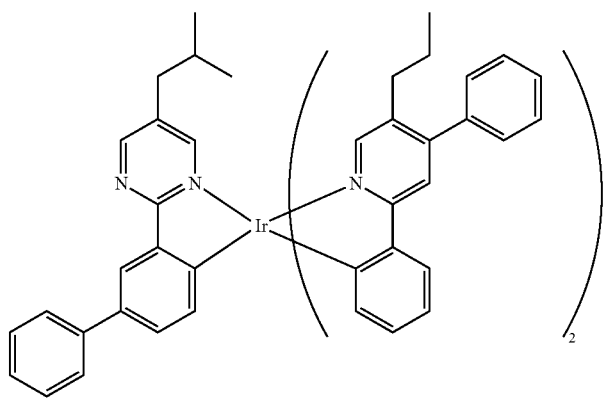
(K-255)
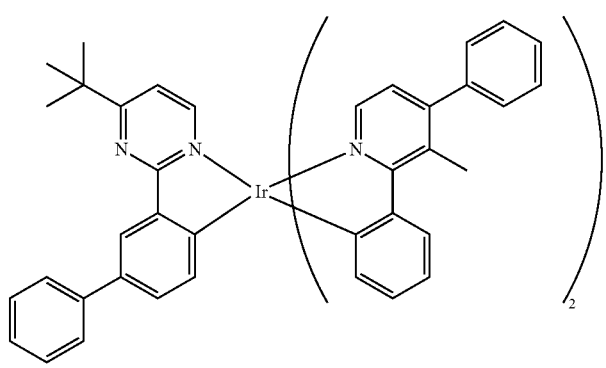
(K-256)

TABLE 11B-continued
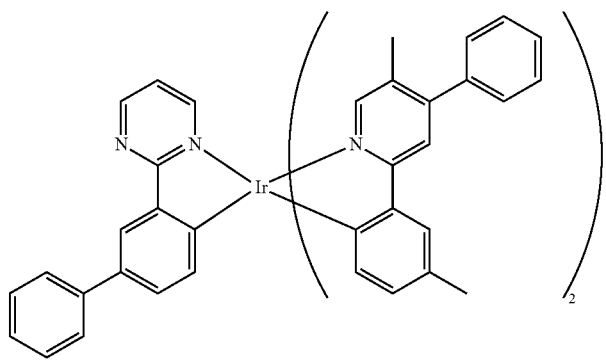
(K-257)
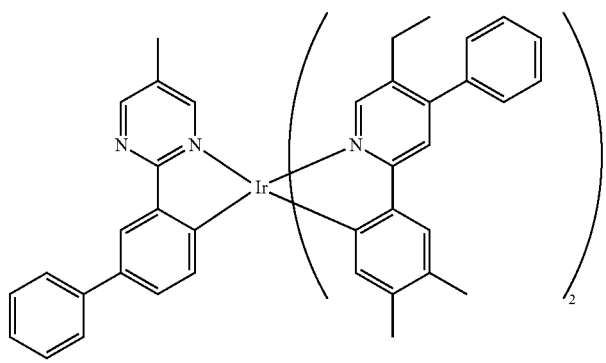
(K-258)
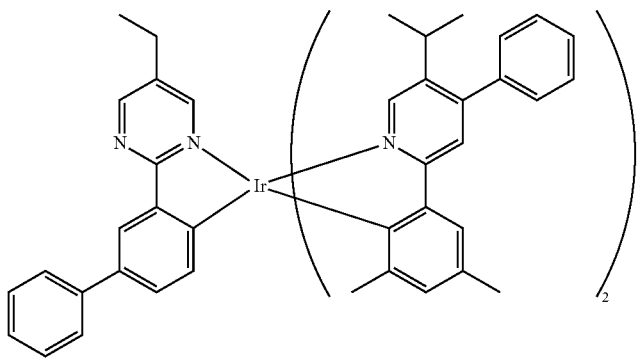
(K-259)
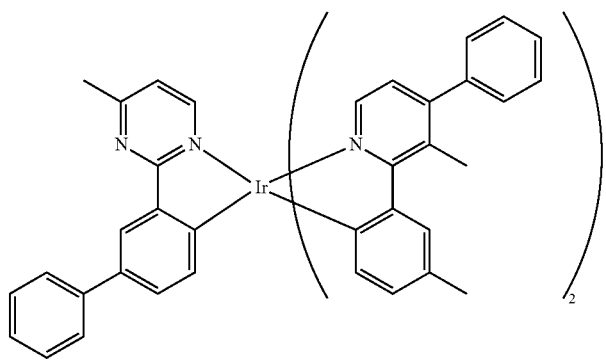
(K-260)

TABLE 11B-continued
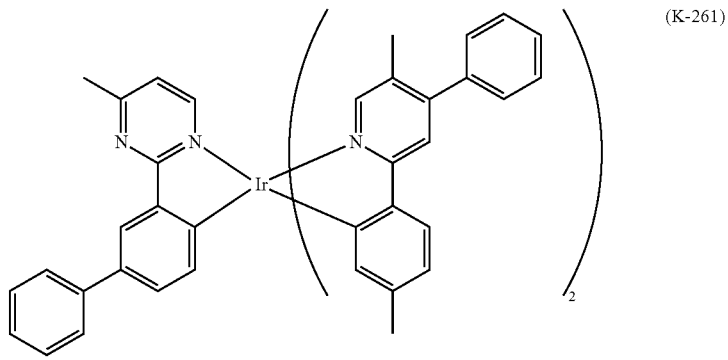
(K-261)
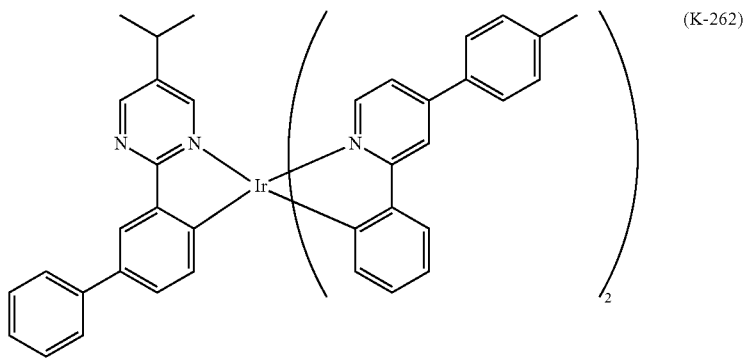
(K-262)
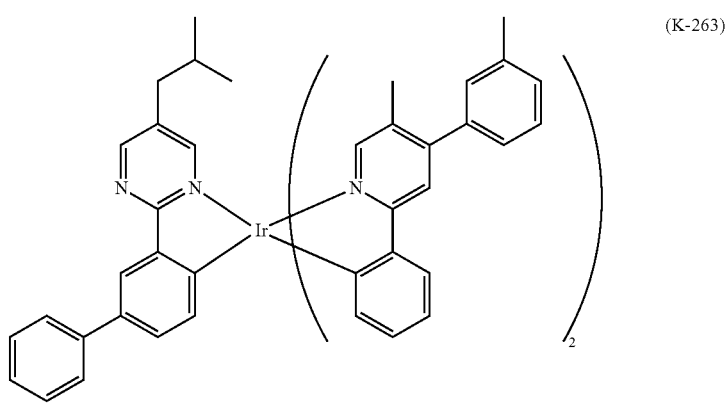
(K-263)
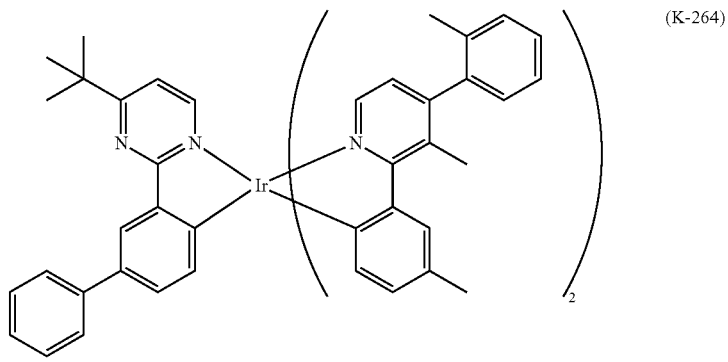
(K-264)

TABLE 12A
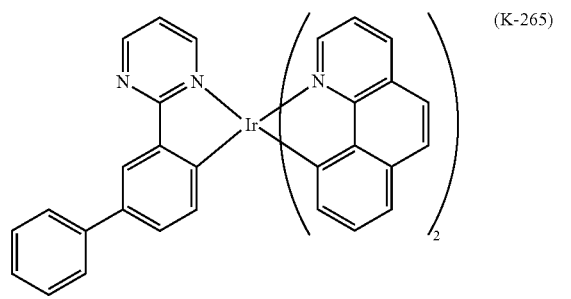 (K-265)
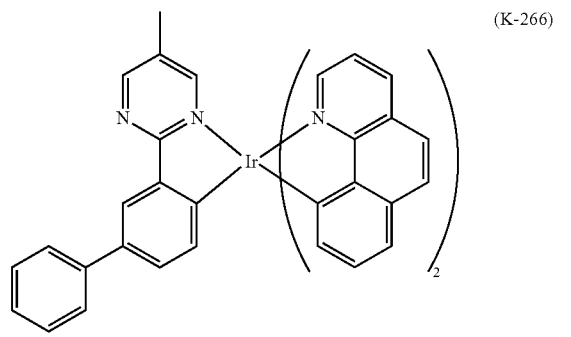 (K-266)
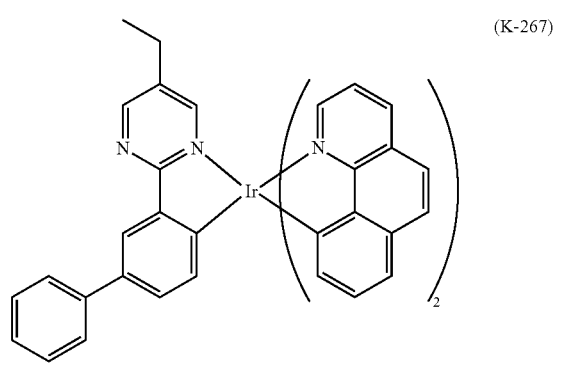 (K-267)
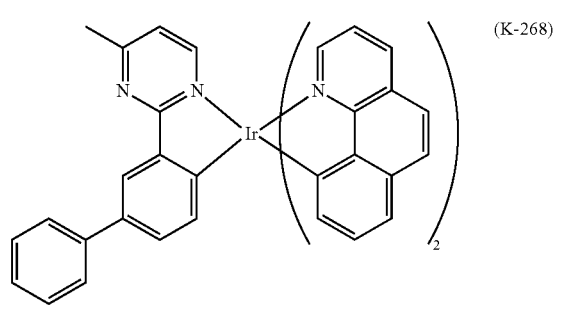 (K-268)
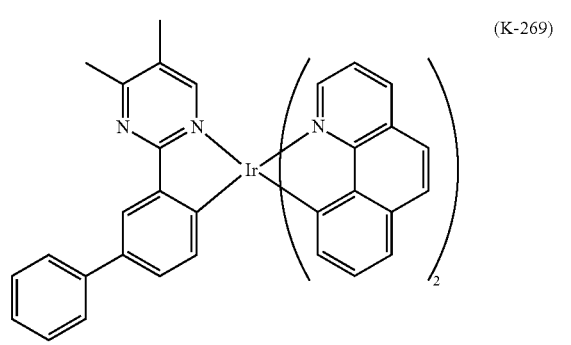 (K-269)
TABLE 12A-continued
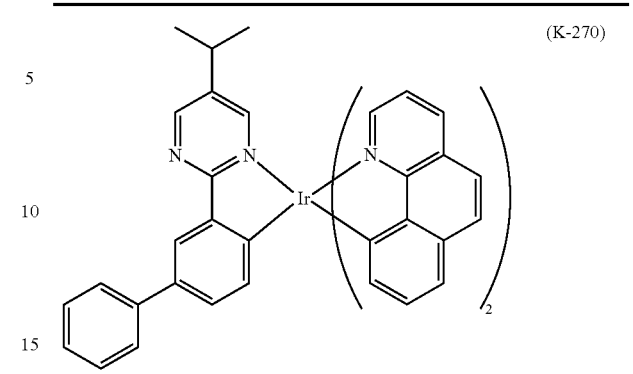 (K-270)
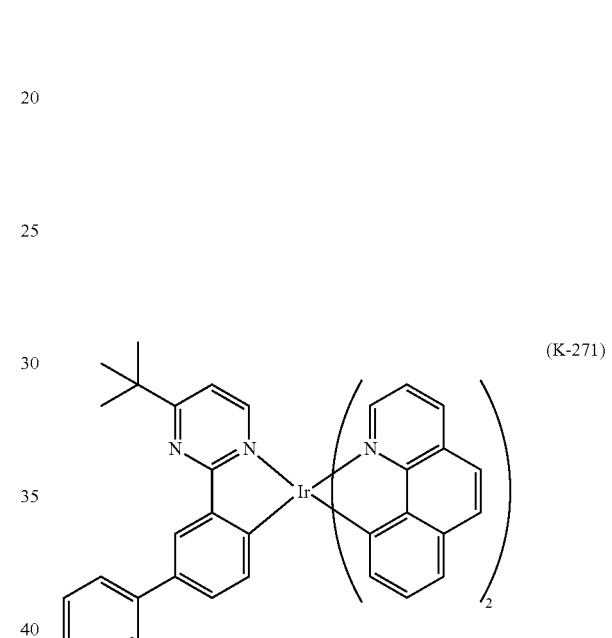 (K-271)
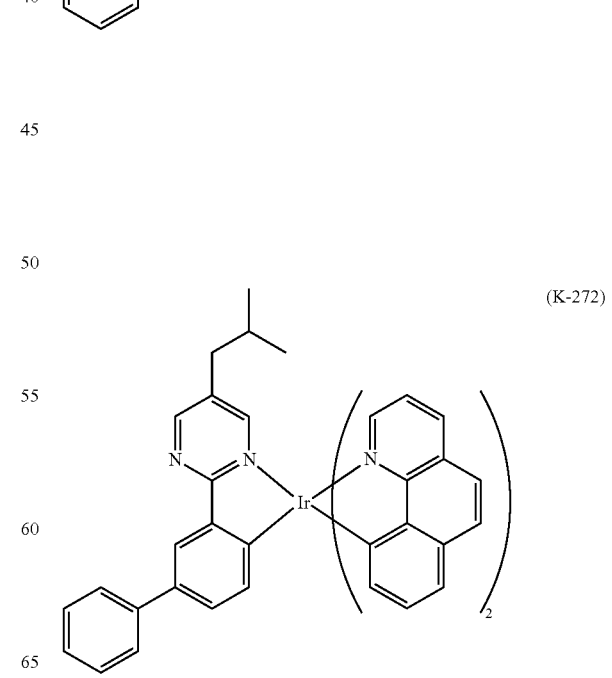 (K-272)

TABLE 12A-continued
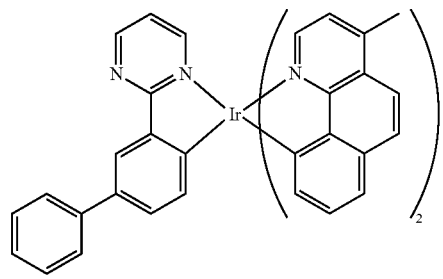
(K-273)
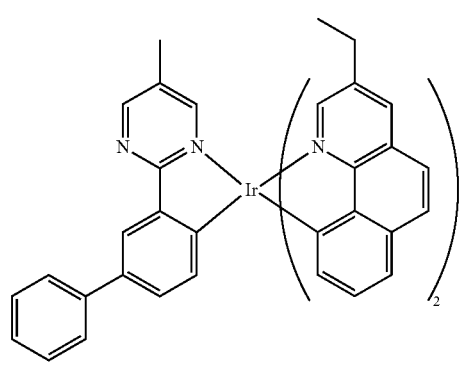
(K-274)
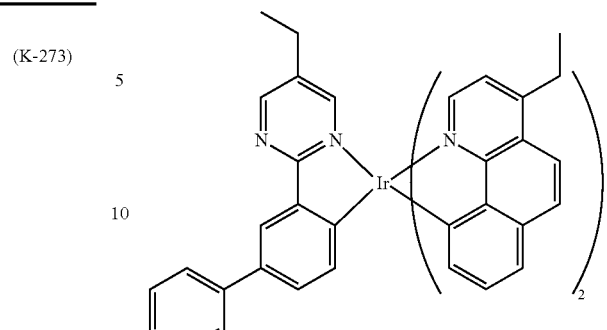
(K-275)
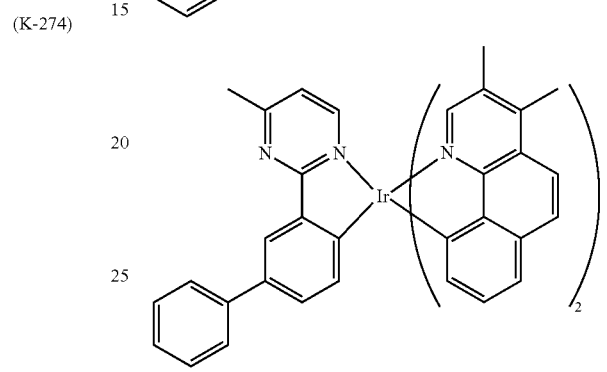
(K-276)
TABLE 12B
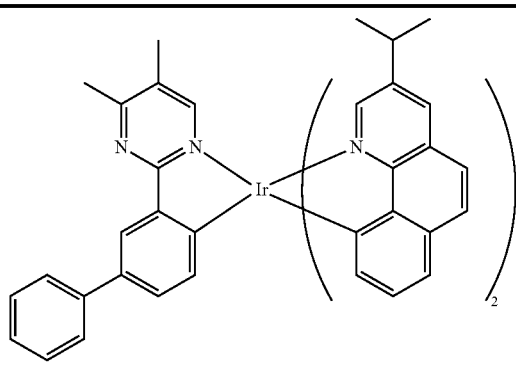
(K-277)
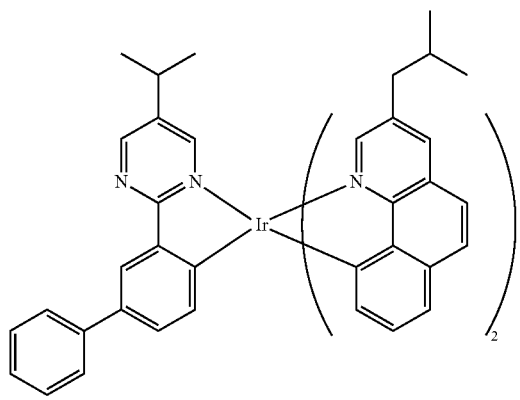
(K-278)

TABLE 12B-continued
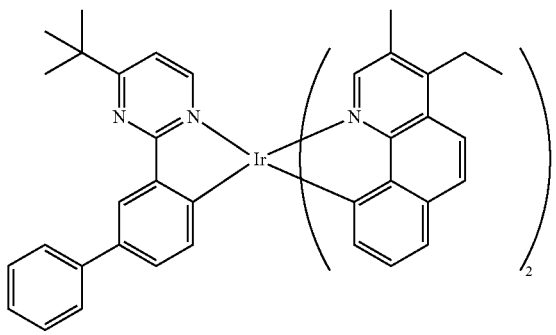
(K-279)
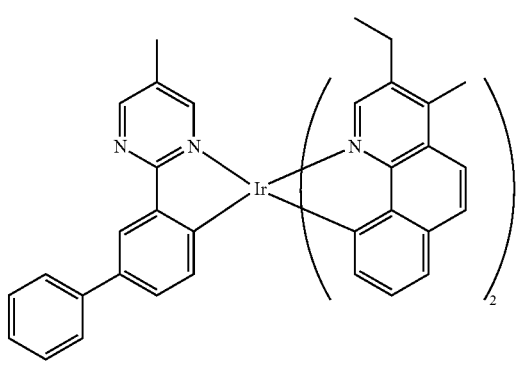
(K-280)
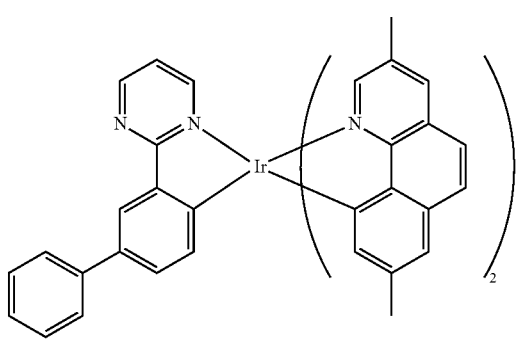
(K-281)
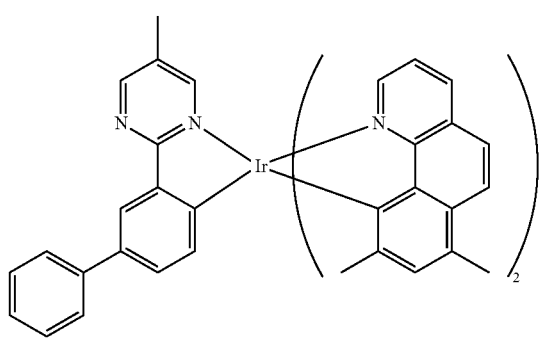
(K-282)

TABLE 12B-continued
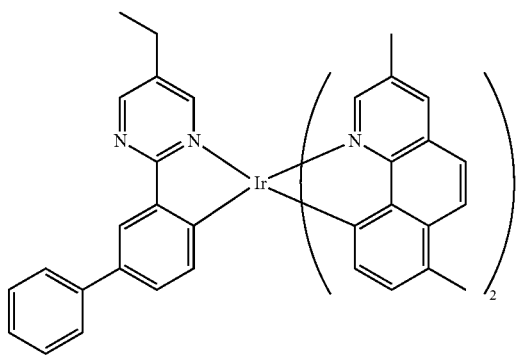
(K-283)
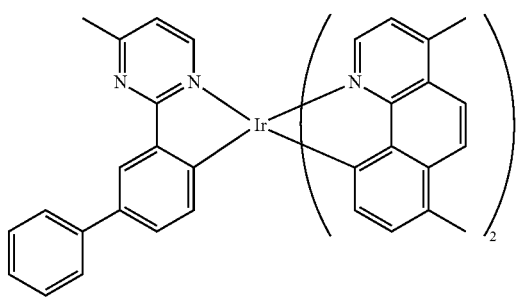
(K-284)
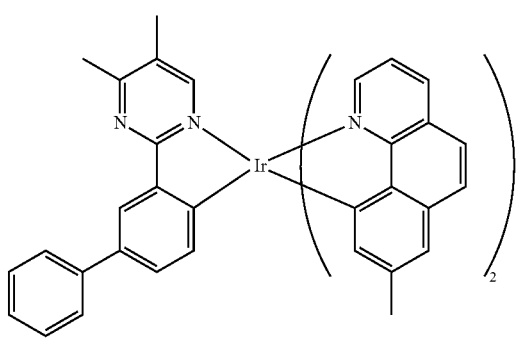
(K-285)
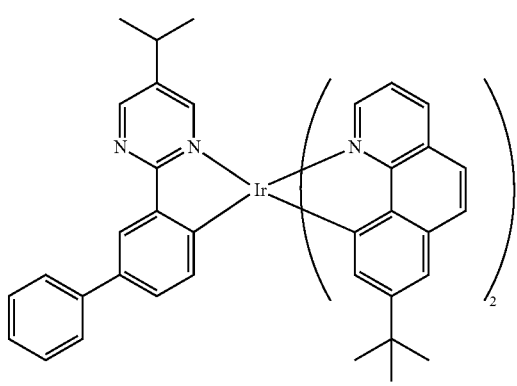
(K-286)

TABLE 12B-continued
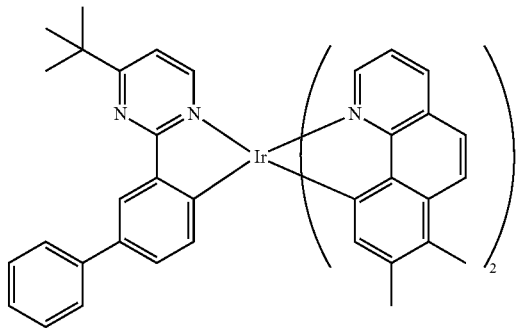
(K-287)
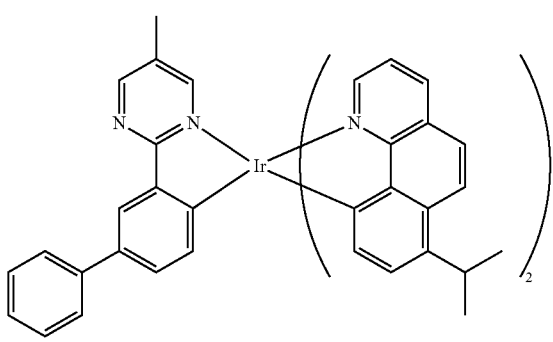
(K-288)
TABLE 13
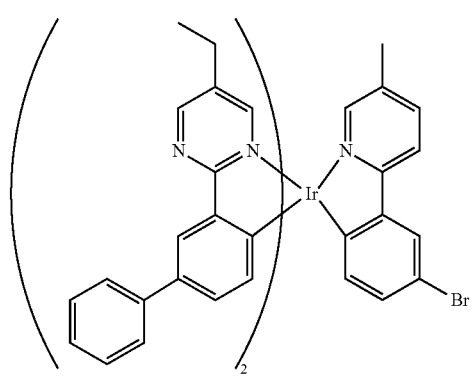
(K-289)
(K-290)
TABLE 13-continued
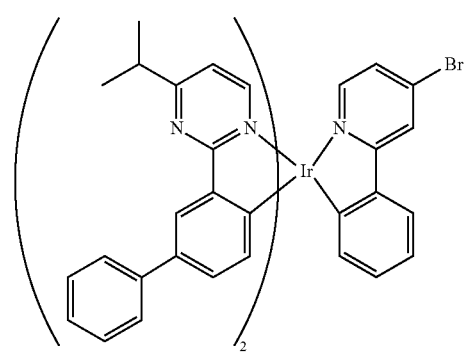
(K-291)
(K-292)

TABLE 13-continued

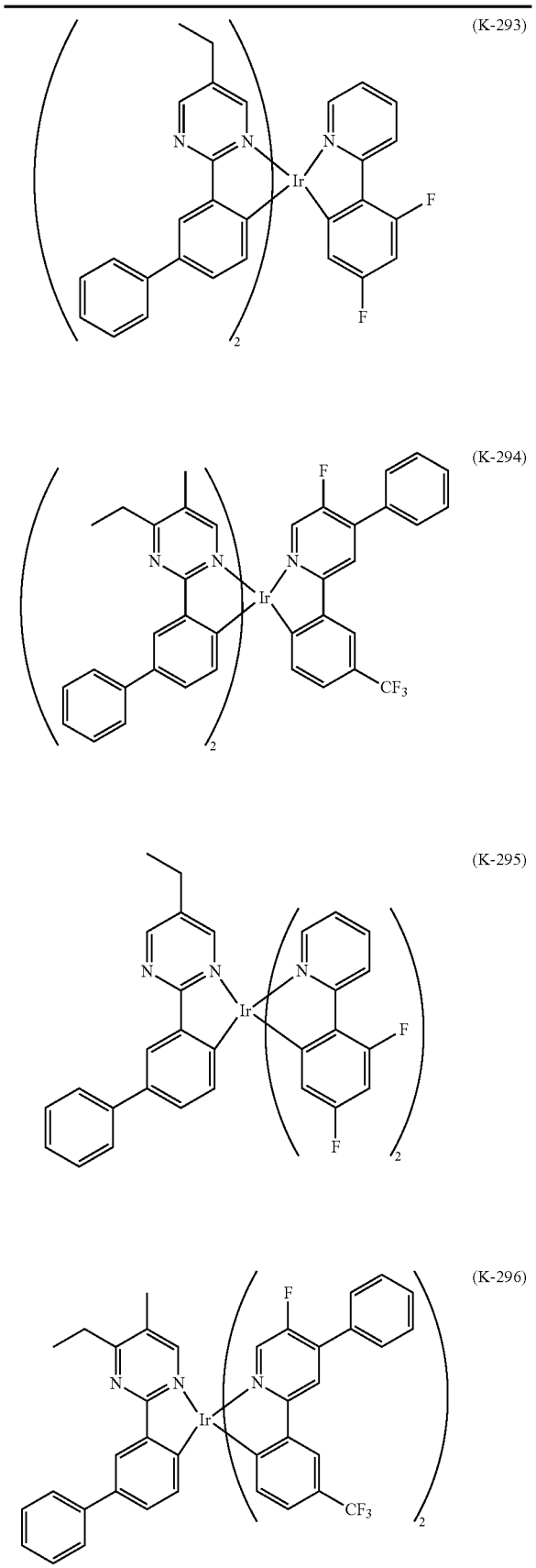
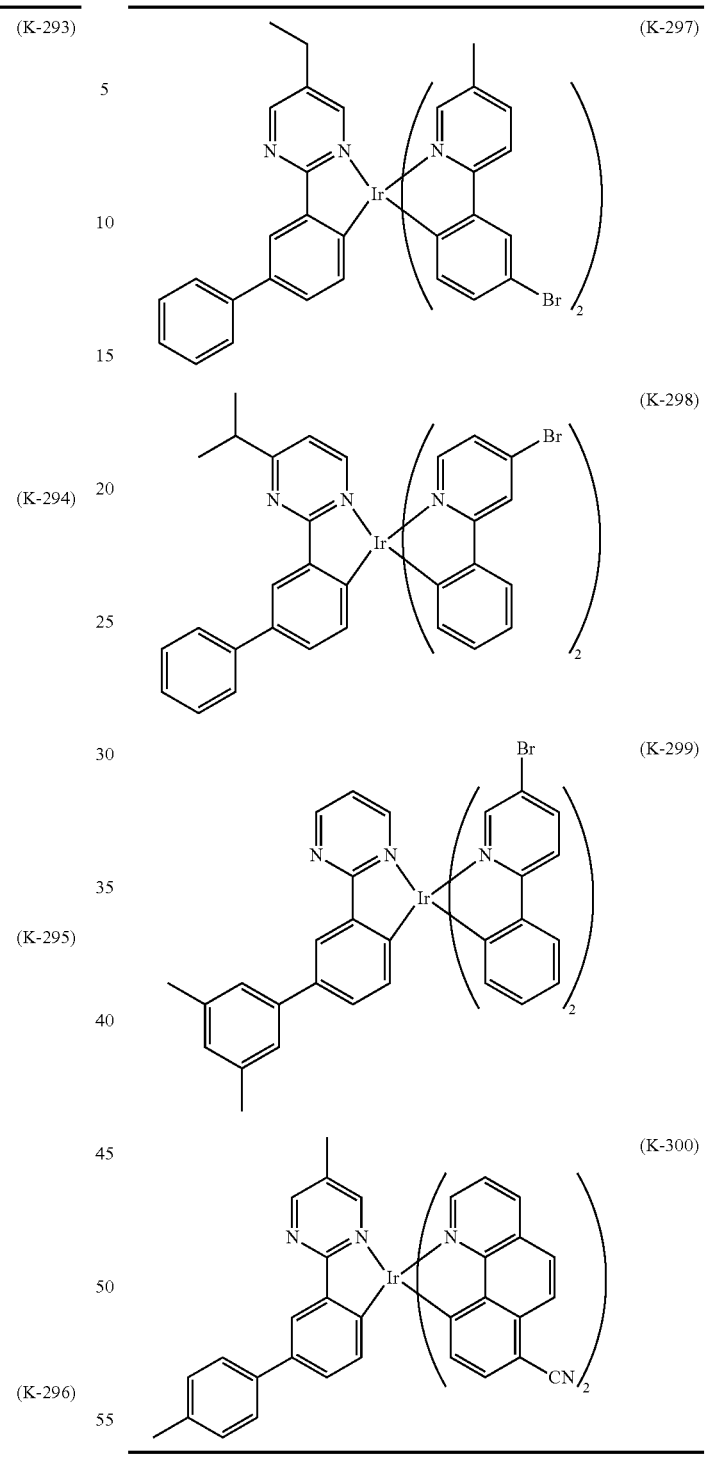

Furthermore, as described above, the iridium complex of the present invention which is represented by General Formula (1) can exhibit phosphorescence as light emission at room temperature, and thus it can be used as a light emitting material or a light emitting substance of an organic light emitting device. Furthermore, by using a light emitting material consisting of the iridium complex of the present invention, an organic light emitting device (preferably, organic electroluminescent light emitting device) can be produced.

Furthermore, by using the iridium complex of the present invention which is represented by General Formula (1), an organic light emitting device, a light emitting instrument, or a lighting instrument with high light emission efficiency can be achieved. It is also possible to achieve an organic light emitting device, a light emitting instrument, or a lighting instrument with low power consumption.

For using the iridium complex of the present invention which is represented by General Formula (1), it is preferable to carry out layer forming by vacuum vapor deposition as the iridium complex is thermally stable and has an excellent sublimability.

Next, the explanations are given for an organic electroluminescent light emitting device that is produced by using the iridium complex of the present invention which is represented by General Formula (1). The organic electroluminescent light emitting device is an device in which plural layers of an organic compound are laminated between a positive electrode and a negative electrode, and it preferably contains, as a light emitting material of a light emitting layer, the iridium complex which is represented by General Formula (1). Furthermore, the light emitting layer generally consists of a light emitting material and a host material.

Representative device constitution of the organic electroluminescent light emitting device of the present invention includes the following constitutions, for example; however, the present invention is not limited to them.
(1) Positive electrode/light emitting layer/negative electrode
(2) Positive electrode/light emitting layer/electron transport layer/negative electrode
(3) Positive electrode/hole transport layer/light emitting layer/negative electrode
(4) Positive electrode/hole transport layer/light emitting layer/electron transport layer/negative electrode
(5) Positive electrode/hole transport layer/light emitting layer/electron transport layer/electron injection layer/negative electrode
(6) Positive electrode/hole injection layer/hole transport layer/light emitting layer/electron transport layer/negative electrode
(7) Positive electrode/hole injection layer/hole transport layer/light emitting layer/electron transport layer/electron injection layer/negative electrode Furthermore, between the light emitting layer and negative electrode, a hole blocking layer (also referred to as a hole barrier layer) may be formed. Furthermore, between the light emitting layer and positive electrode, an electron blocking layer (also referred to as an electron barrier layer) may be formed.

Hereinbelow, explanations are given for each layer constituting the organic electroluminescent light emitting device of the present invention.

<Light Emitting Layer>

The light emitting layer is a layer in which an electron and a hole injected from an electrode bind to each other again and exhibits light emission via excitons, and the part for having light emission may be inside the layer of a light emitting layer or at an interface between the light emitting layer and an adjacent layer.

Film thickness of the light emitting layer is preferably in the range of 2 nm to 1000 nm, more preferably in the range of 2 to 200 nm, and even more preferably in the range of 3 to 150 nm.

According to the present invention, the light emitting layer preferably contains a light emitting material and a host material.

As for the light emitting material, the iridium complex of the present invention which is represented by General Formula (1) may be contained either singly or in combination of two or more types, and it is also possible that other light emitting material is contained therein. Among the compounds that are contained in the light emitting layer, the total content of the iridium complex of the present invention which is represented by General Formula (1) is, in terms of mass ratio, preferably 1 to 50%, more preferably 1 to 30%, and particularly preferably 5 to 20%.

Specific examples of other light emitting material include an anthracene derivative, a pyrene derivative, a chrysene derivative, a fluoranthene derivative, a perylene derivative, a fluorene derivative, an arylacetylene derivative, a styrylarylene derivative, a styrylamine derivative, an arylamine derivative, a boron complex, a squarylium derivative, an oxobenzanthracene derivative, a fluorescein derivative, a polythiophene derivative, a rare earth complex-based compound, an iridium complex, and a platinum complex.

The host material is a compound which is mainly responsible for injection and transport of charges in a light emitting layer. Furthermore, those having mass ratio of 20% or more in the layer are preferred among the compounds that are to be contained in a light emitting layer. More preferably, it is 50% or more, and particularly preferably 80% or more. The upper limit of content of the host material in the compounds that are to be contained in a light emitting layer is preferably 99% or less, in terms of mass ratio, more preferably 95% or less, and particularly preferably 90% or less.

The excited state energy (i.e., $T_1$ level) of a host material is preferably higher than the excited state energy (i.e., $T_1$ level) of the iridium complex of the present invention represented by General Formula (1), which is contained in the same layer.

The host material may be used either singly or plural kinds thereof may be used. By using plural kinds of a host material, charge transfer adjustment can be made so that an organic electroluminescent light emitting device with high efficiency can be achieved.

The host material which can be used in the present invention is not particularly limited, and it may be a low molecular weight compound or a high molecular weight compound having repeating units.

Specific examples of the host material include a triarylamine derivative, a phenylene derivative, a condensed-ring aromatic compound (for example, a naphthalene derivative, a phenanthrene derivative, a fluorene derivative, a pyrene derivative, a tetracene derivative, a coronene derivative, a chrysene derivative, a perylene derivative, a 9,10-diphenylanthracene derivative, rubrene, or the like), a quinacridone derivative, an acridone derivative, a coumarin derivative, a pyran derivative, Nile red, a pyrazine derivative, a benzimidazole derivative, a benzothiazole derivative, a benzoxazole derivative, a stilbene derivative, an organometallic complex (for example, an organoaluminum complex like tris(8-quinolinolate) aluminum, an organoberyllium complex, an organoiridium complex, or an organoplatinum complex, or the like), or a polymer derivative such as poly (phenylenevinylene) derivative, a poly(fluorene) derivative, a poly(phenylene) derivative, a poly(thienylenevinylene) derivative, or a poly(acetylene) derivative.

<Electron Transport Layer>

The electron transport layer consists of a material which has the function of transporting electrons, and it only needs to have a function of delivering the electrons injected from a negative electrode to a light emitting layer.

Film thickness of the electron transport layer is not particularly limited, and it is generally in the range of 2 to 5000 nm, more preferably in the range of 2 to 500 nm, and even more preferably in the range of 5 to 200 nm.

As the material used for an electron transport layer (hereinbelow, referred to as an electron transport material), it only needs to have any one of electron injection property, electron transport property, and hole barrier property, and it can be used by selecting from any of conventionally known compounds.

Specific examples of the electron transport material include a nitrogen-containing aromatic heterocyclic derivative (carbazole derivative, an organoaluminum complex like tris(8-quinolinolate) aluminum, an azacarbazole derivative (1 or more carbon atoms constituting the carbazole ring are substituted with a nitrogen atom), a pyridine derivative, a pyrimidine derivative, a triazine derivative, a quinoline derivative, a quinoxaline derivative, a phenanthroline derivative, an oxazole derivative, a thiazole derivative, an oxadiazole derivative, a triazole derivative, a benzimidazole derivative, a benzoxazole derivative, or the like), a dibenzofuran derivative, a dibenzothiophene derivative, or an aromatic hydrocarbon ring derivative (a naphthalene derivative, an anthracene derivative, triphenylene, or the like).

<Hole Blocking Layer>

The hole blocking layer is a layer having the function of an electron transport layer in broad sense, preferably consists of a material which has the function of transporting electrons and low capability of transporting holes, and by blocking holes while transporting electrons, can increase the probability of re-binding between electrons and holes.

The hole blocking layer is preferably formed such that it is adjacent to the negative electrode side of a light emitting layer.

Film thickness of the hole blocking layer is preferably in the range of 3 to 100 nm, and more preferably in the range of 5 to 30 nm.

As for the material which is used for the electron blocking layer, materials used for the electron transport layer that are described above are preferably used, and the aforementioned host materials are also preferably used as a material of a hole blocking layer.

<Electron Injection Layer>

The electron injection layer (also referred to as a "negative electrode buffer layer") is a layer formed between a negative electrode and a light emitting layer to lower the drive voltage or to enhance the light emission luminance.

Film thickness of the electron injection layer is preferably in the range of 0.1 to 5 nm, and more preferably in the range of 0.1 to 1 nm.

Specific examples of the material which is preferably used for the electron injection layer include a metal (strontium, aluminum, or the like), an alkali metal compound (lithium fluoride, sodium fluoride, or the like), an alkali earth metal compound (magnesium fluoride, calcium fluoride, or the like), a metal oxide (aluminum oxide or the like), or a metal complex (lithium 8-hydroxyquinolate (Liq) or the like). Furthermore, the aforementioned electron transport materials can be also used. Further examples of the electron injecting material include a lithium complex of phenanthroline derivative (LiPB) or a lithium complex of phenoxypyridine (LiPP).

<Hole Transport Layer>

The hole transport layer consists of a material which has a function of transporting holes, and it only needs to have a function of delivering holes that are injected from a positive electrode to a light emitting layer.

Film thickness of the hole transport layer is not particularly limited, and it is generally in the range of 2 to 5000 nm, more preferably in the range of 5 to 500 nm, and even more preferably in the range of 5 to 200 nm.

As for the material which is used for a hole transport layer (hereinbelow, referred to as a hole transport material), it only needs to have any one of the hole injection property, hole transport property, and electron barrier property, and any one can be used by selecting from conventionally known compounds.

Specific examples of the hole transport material include a porphyrin derivative; a phthalocyanine derivative; an oxazole derivative; a phenylenediamine derivative; a stilbene derivative; a triarylamine derivative; a carbazole derivative; an indolocarbazole derivative; an acene derivatives such as anthracene or naphthalene; a fluorene derivative; a fluorenone derivative; a polymer material or an oligomer having polyvinylcarbazole or aromatic amine introduced to a main chain or side chain; polysilane; a conductive polymer or a conductive oligomer (for example, PEDOT:PSS, aniline copolymer, polyaniline, polythiophene, or the like).

<Electron Blocking Layer>

The electron blocking layer is a layer having the function of a hole transport layer in broad sense, preferably consists of a material which has a function of transporting holes and low capability of transporting electrons, and by transporting holes while blocking electrons, can increase the probability of re-binding between electrons and holes.

Film thickness of the electron blocking layer is preferably in the range of 3 to 100 nm, and more preferably in the range of 5 to 30 nm.

Furthermore, the constitution of the aforementioned hole transport layer can be also used for the electron blocking layer if necessary.

<Hole Injection Layer>

In the present invention, the hole injection layer (also referred to as a "positive electrode buffer layer") is a layer formed between a positive electrode and a light emitting layer to lower the drive voltage or to enhance the light emission luminance.

As the material which is used for the hole injection layer, a phthalocyanin derivative represented by copper phthalocyanin, a hexaazatriphenylene derivative, a metal oxide represented by vanadium oxide, amorphous carbon, a conductive polymer such as polyaniline (emeraldine) or polythiophene, a cyclometallated complex represented by tris(2-phenylpyridine)) iridium complex, a triarylamine derivative, or the like is preferable.

The organic electroluminescent light emitting device of the present invention is preferably supported on a substrate. Materials of a substrate are not particularly limited, and examples thereof include glass such as alkali glass, alkali-free glass, or quartz glass, and transparent plastics that are typically used for an organic electroluminescent light emitting device of a related art.

Specific examples of the material constituting a positive electrode which can be used include a metal simple substance such as gold, platinum, silver, copper, nickel, palladium, cobalt, selenium, vanadium, or tungsten, or an alloy thereof, and a metal oxide such as tin oxide, zinc oxide, indium oxide, tin indium oxide (ITO), or zinc indium oxide. Furthermore, a conductive polymer such as polyaniline, polypyrrole, polythiophene, or polyphenylene sulfide can be also used. Those electrode materials may be used either singly or in combination of two or more types thereof. Furthermore, the positive electrode may be composed of a single layer or plural layers.

As the material for constituting a negative electrode, examples include a metal simple substance such as lithium, sodium, potassium, calcium, magnesium, aluminum, indium, ruthenium, titanium, manganese, yttrium, silver, lead, tin, or chrome. Furthermore, it is also possible to have an alloy by combining those metals. For example, an alloy like lithium-indium, sodium-potassium, magnesium-silver, aluminum-lithium, aluminum-magnesium or magnesium-indium may be used. Furthermore, a metal oxide like indium tin oxide (ITO) can be used. Those electrode materials may be used either singly or in combination of two or more types thereof. Furthermore, the negative electrode may be either a monolayer structure or a multilayer structure.

An organic light emitting device including the iridium complex of the present invention which is represented by General Formula (1) can be produced by a vacuum vapor deposition method, a solution coating method, a transfer method using laser or the like, or a spray method. In particular, it is preferable that light emitting layer containing the iridium complex of the present invention which is represented by General Formula (1) is formed by a vacuum vapor deposition method.

When each layer like hole transport layer, light emitting layer, or electron transport layer is formed by a vacuum vapor deposition method, conditions for vacuum vapor deposition are not particularly limited; however, it is preferable that vapor deposition is carried out at vapor deposition rate of 0.01 to 50 nm/second or so under vacuum of $10^{-4}$ to $10^{-5}$ Pa or so, with boat temperature of 50 to 500° C. or so and substrate temperature of −50 to 300° C. or so. In a case in which each layer like hole transport layer, light emitting layer, or electron transport layer is formed by using plural materials, it is preferable to carry out co-vapor deposition while controlling the temperature of each of boats that are added with the materials.

EXAMPLES

Hereinbelow, the present invention is explained in greater detail by showing Examples; however, the present invention should not be construed as being limited to the Examples. Incidentally, the compounds corresponding to the Examples are referred to as a "present invention compound" and the compounds corresponding to the Comparative Examples are referred to as a "comparative compound".

Example I-1

Synthesis of the Present Invention Compound (K-3)

[Chem. 23]

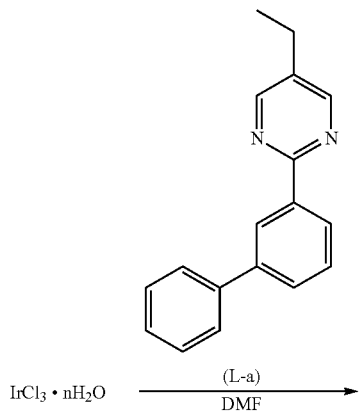

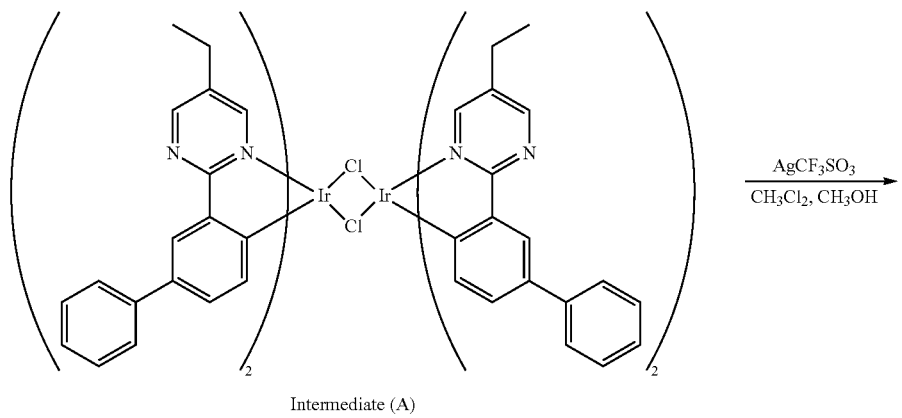

Intermediate (A)

-continued

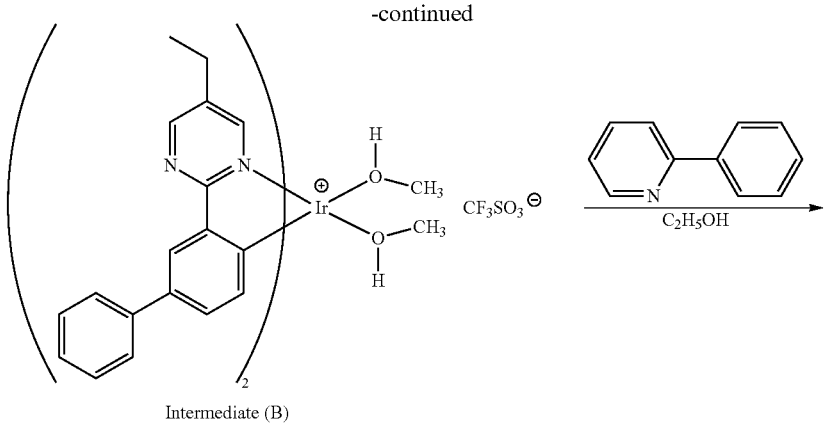

Intermediate (B)

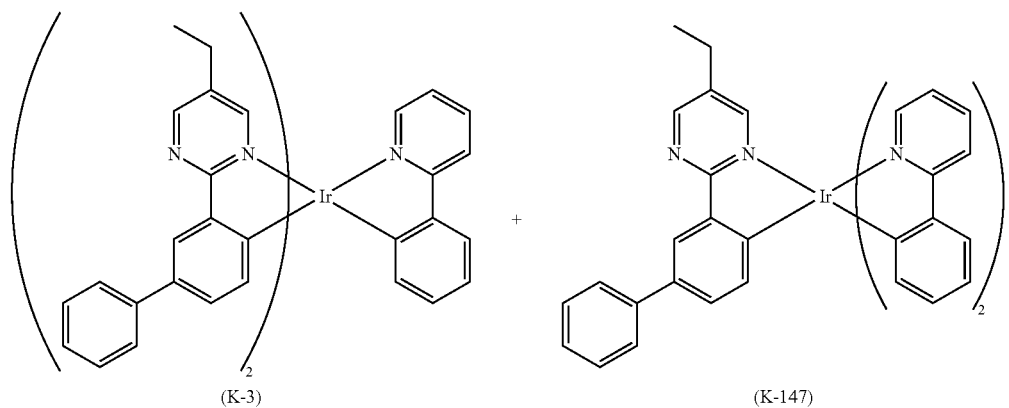

(K-3)          (K-147)

IrCl₃.nH₂O (0.366 g) and 0.524 g (2.01 mmol) of the ligand (L-a) were dissolved in 20 ml of DMF, and after purging the solution with argon gas for 30 minutes, the solution was irradiated with microwave (2450 MHz) for 30 minutes. The reaction solution was cooled to room temperature, and by distilling the solvent to about 5 mL under reduced pressure and adding water, solids were precipitated. The solids were subjected to recrystallization using dichloromethane and hexane, and according to subsequent washing with methanol and hexane, the intermediate (A) was obtained. The obtained amount was 0.5658 g (yield: 75.7%). 0.6025 g (0.4 mmol) of the intermediate (A) which has been synthesized according to the above method was dissolved in a mixture solvent containing 30 ml of dichloromethane and 10 ml of methanol, and the resulting solution was purged with argon gas for 30 minutes. After that, 0.2019 g (0.79 mmol) of silver trifluoromethane sulfonic acid was added to the solution, and stirred for 5 hours at 50° C. After cooling to room temperature, filtration through a Celite layer was performed, and to the intermediate (B) which has been obtained by removing filtrate according to distillation under reduced pressure, 0.3524 g (2.44 mmol) of 2-phenylpyridine and 50 ml of ethanol were added and refluxed with heating for 3 days under argon atmosphere. After cooling to room temperature, the solvent was removed by distillation under reduced pressure. The obtained solids were dissolved in dichloromethane, and recrystallized by adding hexane thereto. After that, purification was carried out by using silica gel column chromatography (elution solution: mixture solvent of dichloromethane and hexane), and the present invention compound (K-3) was obtained. The obtained amount was 0.3536 g (yield: 50.7%). Identification of the compound was carried out by using ¹H-NMR and ESI-MS. The analysis data of the present invention compound (K-3) are shown below. The (K-3) obtained by this method was a facial isomer.

¹H-NMR (400 MHz/acetone-d₆) δ: 8.70 (dd, 2H), 8.36 (dd, 2H), 8.13 (d, 1H), 8.01 (d, 1H), 7.87 (d, 1H), 7.77-7.83 (m, 3H), 7.65 (d, 4H), 7.39 (t, 4H), 7.25 (dd, 2H), 7.17 (dd, 2H), 7.10 (dd, 1H), 6.86-6.95 (m, 4H), 6.77 (t, 1H), 2.49-2.57 (m, 4H), 1.09 (m, 6H)

ESI-MS: m/z=865.9

Furthermore, as a byproduct of the reaction, an extremely small amount of the present invention compound (K-147) was obtained (yield: 0.7%). The analysis data of the present invention compound (K-147) are shown below. The (K-147) obtained by this method was a facial isomer.

¹H-NMR (400 MHz/acetone-d₆) δ: 8.68 (d, 1H), 8.34 (d, 1H), 8.08-8.12 (m, 2H), 7.85 (d, 1H), 7.72-7.80 (m, 5H), 7.68 (d, 1H), 7.63 (d, 2H), 7.37 (t, 2H), 7.23 (t, 1H), 7.13 (d, 1H), 7.05-7.09 (m, 2H), 6.82-6.90 (m, 5H), 6.70-6.75 (m, 2H), 2.52 (q, 2H), 1.07 (t, 3H)

ESI-MS: m/z=760.6

From the above, it was found that ligand scrambling hardly occurs during the synthesis of the present invention compound (K-3). It was also found that the separation and purification of (K-3) and (K-147) is easy.

Example I-2

Synthesis of the Present Invention Compound (K-51)

[Chem. 24]

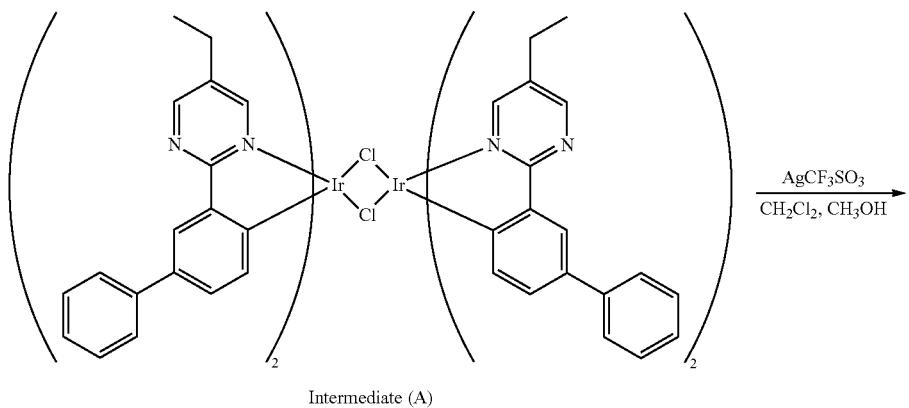

Intermediate (A)

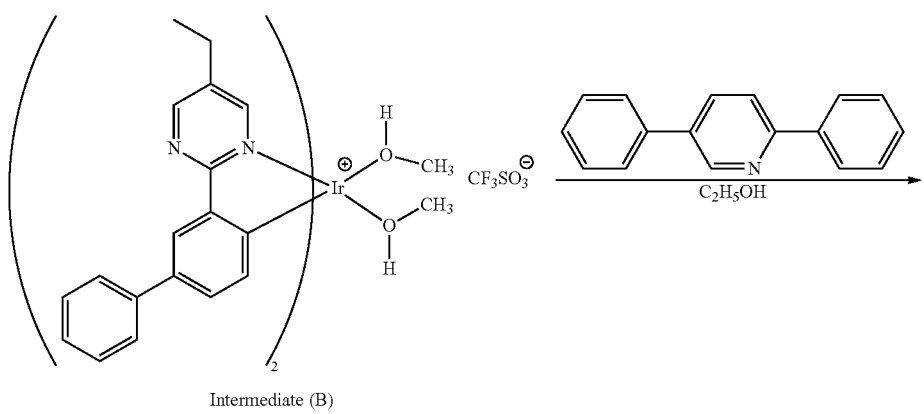

Intermediate (B)

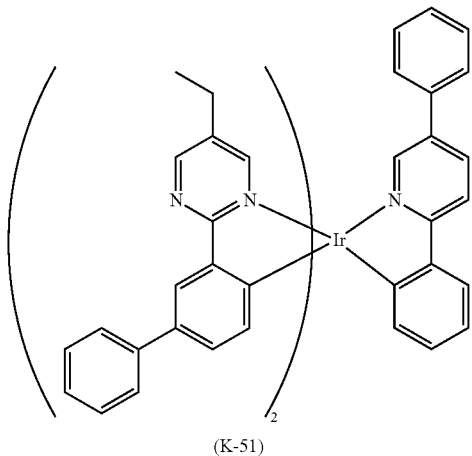

(K-51)

0.4005 g (0.27 mmol) of the intermediate (A) was dissolved in a mixture solvent containing 30 ml of dichloromethane and 10 ml of methanol, and the resulting solution was purged with argon gas for 30 minutes. After that, 0.1613 g (0.63 mmol) of silver trifluoromethane sulfonic acid was added to the solution, and stirred for 15 hours at 50° C. After cooling to room temperature, filtration through a Celite layer was performed, and to the intermediate (B) which has been obtained by removing filtrate according to distillation under reduced pressure, 0.2316 g (1.00 mmol) of 2,5-diphenylpyridine and 30 ml of ethanol were added and refluxed with heating for 3 days under argon atmosphere. After cooling to room temperature, the solvent was removed by distillation under reduced pressure. The obtained solids were dissolved in dichloromethane, and recrystallized by adding hexane thereto. After that, purification was carried out by using silica gel column chromatography (elution solution: mixture solvent of ethyl acetate and hexane), and the present invention compound (K-51) was obtained. The obtained amount was 0.2913 g (yield: 57.3%). Identification of the compound was carried out by using $^1$H-NMR and ESI-MS. The analysis data of the present invention compound (K-51) are shown below. The (K-51) obtained by this method was a facial isomer. Furthermore, ligand scrambling did not occur during the synthesis of the present invention compound (K-51).

$^1$H-NMR (400 MHz/dichloromethane-$d_2$) δ: 8.66 (dd, 2H), 8.35 (dd, 2H), 8.03 (d, 1H), 7.95 (dd, 1H), 7.89 (d, 1H), 7.75 (d, 1H), 7.72 (d, 2H), 7.62-7.65 (m, 5H), 7.31-7.41 (m, 9H), 7.20-7.28 (m, 4H), 6.87-6.99 (m, 5H), 2.48-2.56 (m, 4H), 1.10-1.19 (m, 6H)

ESI-MS: m/z=941.7

Example I-3

Synthesis of the Present Invention Compound (K-59)

[Chem. 25]

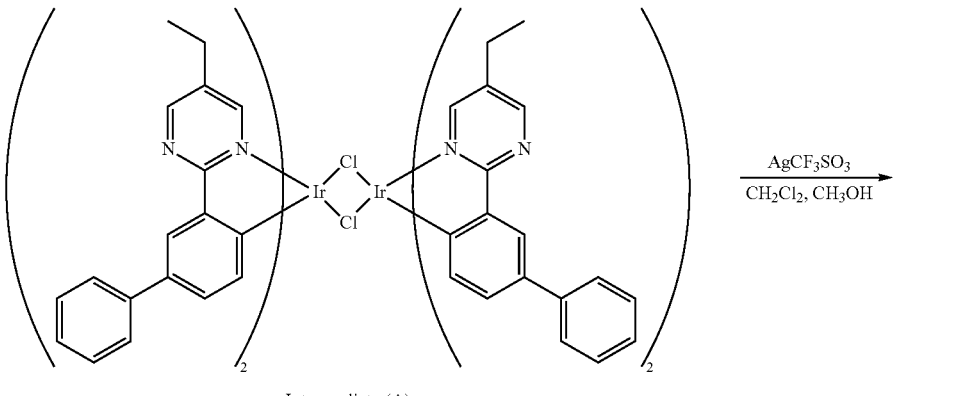

Intermediate (A)

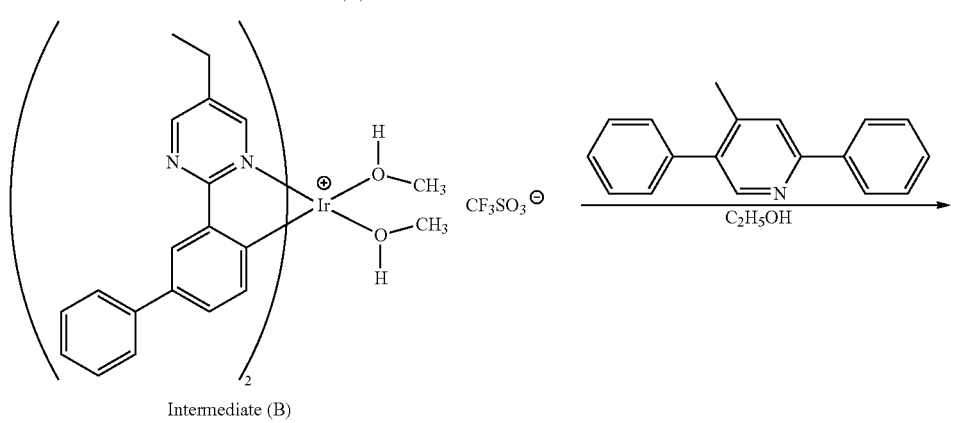

Intermediate (B)

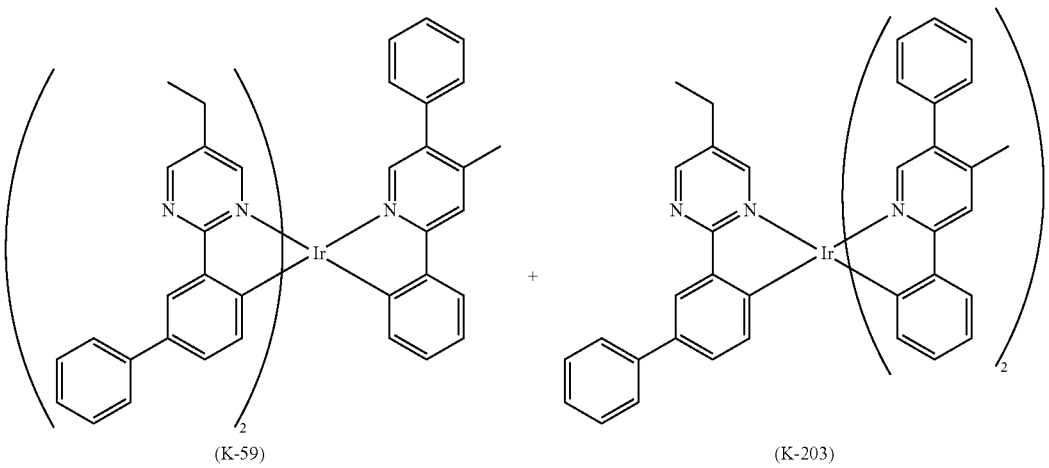

(K-59)  +  (K-203)

0.4045 g (0.27 mmol) of the intermediate (A) was dissolved in a mixture solvent containing 15 ml of dichloromethane and 5 ml of methanol, and the resulting solution was purged with argon gas for 30 minutes. After that, 0.1832 g (0.71 mmol) of silver trifluoromethane sulfonic acid was added to the solution, and stirred for 5 hours at 50° C. After cooling to room temperature, filtration through a Celite layer was performed, and to the intermediate (B) which has been obtained by removing filtrate according to distillation under reduced pressure, 0.3321 g (1.35 mmol) of 4-methyl-2,5-diphenylpyridine and 20 ml of ethanol were added and refluxed with heating for 3 days under argon atmosphere. After cooling to room temperature, the solvent was removed by distillation under reduced pressure. The obtained solids were dissolved in dichloromethane, and recrystallized by adding hexane thereto. After that, purification was carried out by using silica gel column chromatography (elution solution: mixture solvent of dichloromethane and hexane), and the present invention compound (K-59) was obtained. The obtained amount was 0.2313 g (yield: 44.5%). Identification of the compound was carried out by using $^1$H-NMR and ESI-MS. The analysis data of the present invention compound (K-59) are shown below. The (K-59) obtained by this method was a facial isomer.

$^1$H-NMR (400 MHz/dichloromethane-$d_2$) δ: 8.65 (s, 1H), 8.57 (s, 1H), 8.37 (s, 2H), 7.88 (s, 1H), 7.74 (d, 1H), 7.63-7.67 (m, 6H), 7.49 (s, 1H), 7.36-7.42 (m, 7H), 7.22-7.28 (m, 4H), 7.16 (d, 2H), 6.84-6.98 (m, 5H), 2.56 (q, 2H), 2.47 (q, 2H), 2.44 (s, 3H), 1.17 (t, 3H), 1.08 (t, 3H)

ESI-MS: m/z=957.0

Furthermore, as a byproduct of the reaction, an extremely small amount of the present invention compound (K-203) was obtained (yield: 0.8%). The separation and purification of (K-59) and (K-203) as the present invention compound was easy. The analysis data of the present invention compound (K-203) are shown below. The (K-203) obtained by this method was a facial isomer.

$^1$H-NMR (400 MHz/dichloromethane-$d_2$) δ: 8.52 (d, 1H), 8.30 (d, 1H), 7.85 (s, 1H), 7.80 (s, 1H), 7.70 (dd, 2H), 7.63 (dd, 3H), 7.49 (d, 2H), 7.31-7.41 (m, 8H), 7.25 (dd, 1H), 7.16-7.20 (m, 3H), 7.03-7.06 (m, 2H), 6.81-6.93 (m, 7H), 2.44-2.49 (m, 5H), 2.32 (s, 3H), 1.06 (t, 3H)

ESI-MS: m/z=942.0

From the above, it was found that ligand scrambling hardly occurs during the synthesis of the present invention compound (K-59). It was also found that the separation and purification of (K-59) and (K-203) is easy.

Example I-4

Synthesis of the Present Invention Compound (K-99)

[Chem. 26]

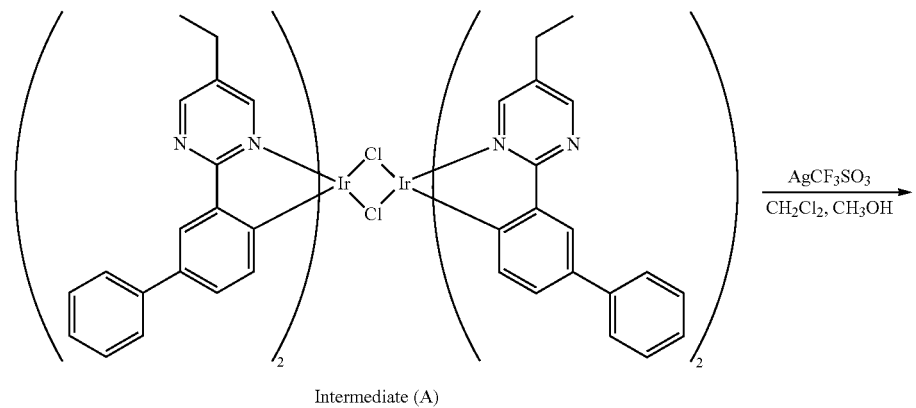

Intermediate (A)

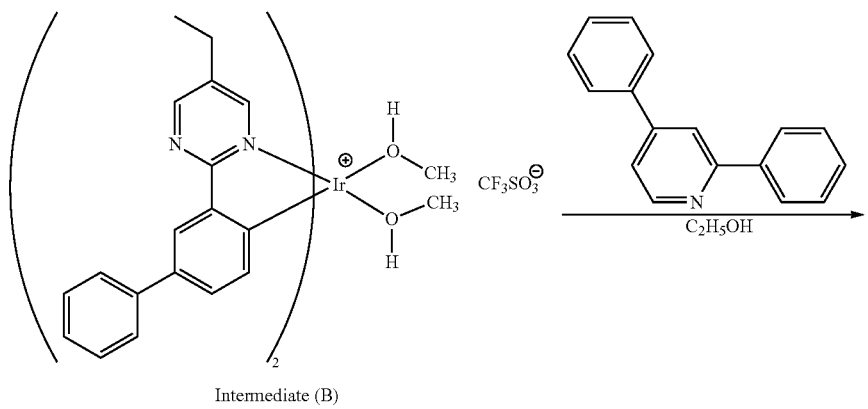

Intermediate (B)

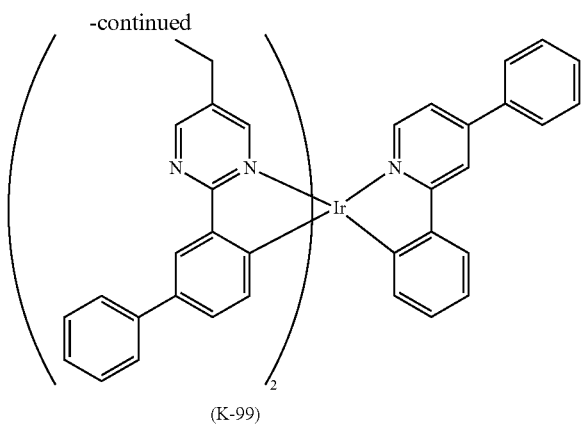

(K-99)

0.2486 g (0.15 mmol) of the intermediate (A) was dissolved in a mixture solvent containing 30 ml of dichloromethane and 10 ml of methanol, and the resulting solution was purged with argon gas for 30 minutes. After that, 0.0919 g (0.36 mmol) of silver trifluoromethane sulfonic acid was added to the solution, and stirred for 3 hours at 50° C. After cooling to room temperature, filtration through a Celite layer was performed, and to the intermediate (B) which has been obtained by removing filtrate according to distillation under reduced pressure, 10 ml of methanol and 10 ml of ethanol were added and argon bubbling was carried out for 30 minutes. Temperature of the resulting solution was increased to 80° C. or so, and thereafter 0.1163 g (0.50 mmol) of 2,4-diphenylpyridine was added and refluxed with heating for 2 days under argon atmosphere. After cooling to room temperature, the solvent was removed by distillation under reduced pressure. The obtained solids were dissolved in dichloromethane, and recrystallized by adding hexane thereto. After that, purification was carried out by using silica gel column chromatography (elution solution: dichloromethane), and the present invention compound (K-99) was obtained. The obtained amount was 0.2129 g (yield: 75.4%).

Identification of the compound was carried out by using $^1$H-NMR and ESI-MS. The analysis data of the present invention compound (K-99) are shown below. The (K-99) obtained by this method was a facial isomer. Furthermore, ligand scrambling did not occur during the synthesis of the present invention compound (K-99).

$^1$H-NMR (400 MHz/dichloromethane-$d_2$) δ: 8.65 (dd, 2H), 8.35 (dd, 2H), 8.19 (d, 1H), 7.82 (d, 1H), 7.71-7.74 (m, 3H), 7.64-7.69 (m, 6H), 7.47-7.55 (m, 3H), 7.39 (t, 4H), 7.24-7.28 (m, 3H), 7.18-7.22 (m, 2H), 6.92-6.99 (m, 2H), 6.86-6.88 (m, 3H), 2.56 (q, 2H), 2.52 (q, 2H), 1.18 (t, 3H), 1.14 (t, 3H)

ESI-MS: m/z=942.7

Example I-5

Synthesis of the Present Invention Compound (K-123)

[Chem. 27]

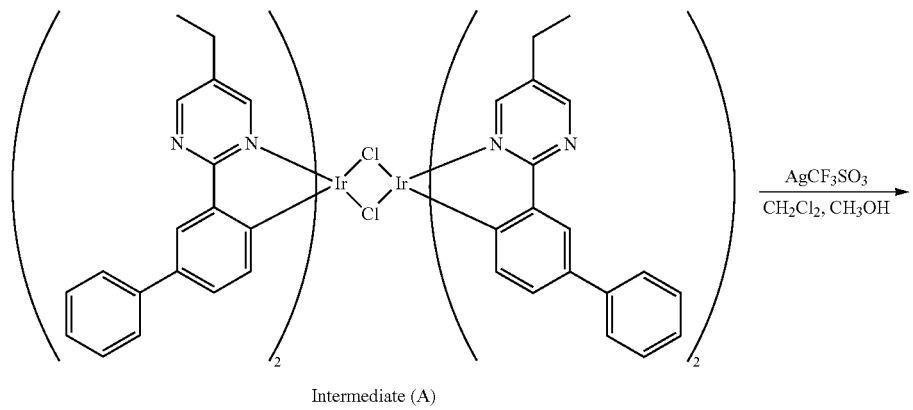

Intermediate (A)

-continued

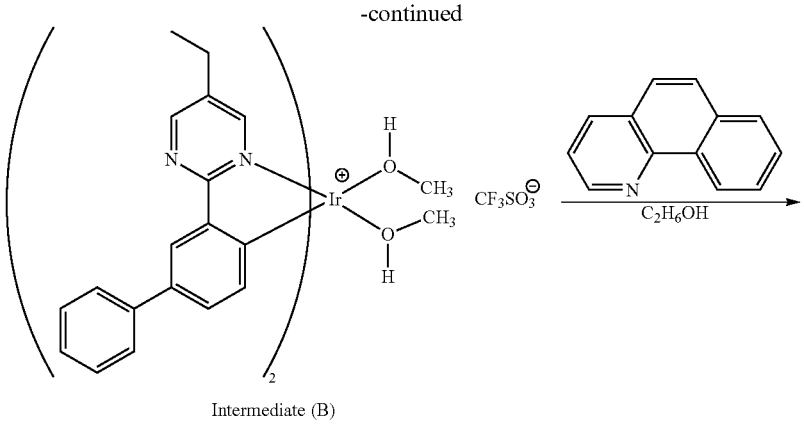

Intermediate (B)

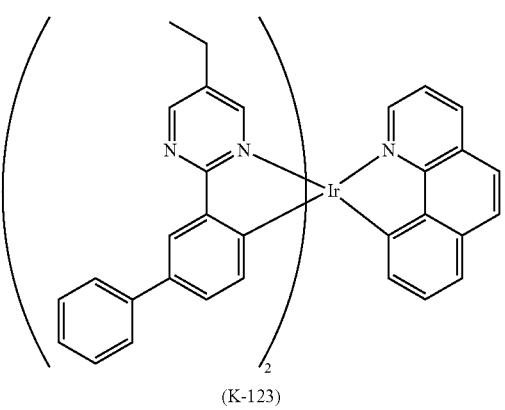

(K-123)

0.5004 g (0.33 mmol) of the intermediate (A) was dissolved in a mixture solvent containing 15 ml of dichloromethane and 5 ml of methanol, and the resulting solution was purged with argon gas for 30 minutes. After that, 0.1816 g (0.71 mmol) of silver trifluoromethane sulfonic acid was added to the solution, and stirred for 5 hours at 50° C. After cooling to room temperature, filtration through a Celite layer was performed, and to the intermediate (B) which has been obtained by removing filtrate according to distillation under reduced pressure, 0.1712 g (0.96 mmol) of benzo[h]quinoline and 20 ml of ethanol were added and refluxed with heating for 3 days under argon atmosphere. After cooling to room temperature, the solvent was removed by distillation under reduced pressure. The obtained solids were dissolved in dichloromethane, and recrystallized by adding hexane thereto. After that, purification was carried out by using silica gel column chromatography (elution solution: mixture solvent of ethyl acetate and hexane), and the present invention compound (K-123) was obtained. The obtained amount of the facial isomer was 0.1322 g (yield: 22.5%), and the obtained amount of the meridional isomer was 0.1536 g (yield: 26.2%). Identification of the compound was carried out by using $^1$H-NMR and ESI-MS.

The analysis data of the facial isomer of the present invention compound (K-123) are shown below.

$^1$H-NMR (400 MHz/dichloromethane-$d_2$) δ: 8.69 (d, 1H), 8.58 (d, 1H), 8.37 (d, 1H), 8.33 (d, 1H), 8.19 (dd, 1H), 7.98 (dd, 1H), 7.86 (d, 1H), 7.79 (d, 1H), 7.57-7.68 (m, 5H), 7.47 (d, 1H), 7.33-7.43 (m, 6H), 7.23-7.30 (m, 4H), 7.01-7.07 (m, 3H), 6.60 (d, 1H), 2.58 (q, 2H), 2.37 (q, 2H), 1.21 (t, 3H), 1.01 (t, 3H)

ESI-MS: m/z=889.6

The analysis data of the meridional isomer of the present invention compound (K-123) are shown below.

$^1$H-NMR (400 MHz/dichloromethane-$d_2$) δ: 8.45 (dd, 2H), 8.38 (d, 1H), 8.30-8.32 (m, 2H), 8.20 (dd, 1H), 7.96 (d, 1H), 7.87 (d, 1H), 7.63-7.69 (m, 5H), 7.51-7.55 (m, 2H), 7.35-7.43 (m, 7H), 7.23-7.31 (m, 4H), 6.90 (d, 1H), 6.71 (d, 1H), 2.27-2.39 (m, 4H) 0.99 (t, 3H), 0.92 (q, 3H)

ESI-MS: m/z=889.6

Example I-6

Synthesis of the Present Invention Compound (K-147)

[Chem. 28]

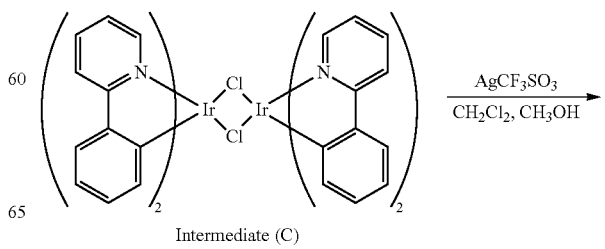

Intermediate (C)

-continued

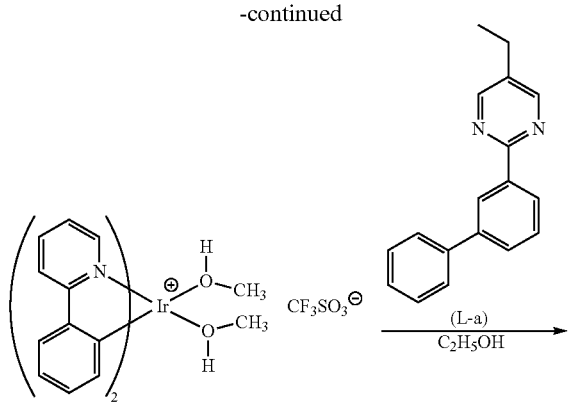

Intermediate (D)

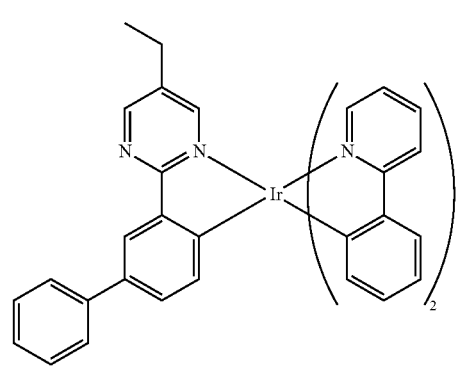

(K-147)

0.200 g (0.19 mmol) of the intermediate (C) was dissolved in a mixture solvent containing 10 ml of dichloromethane and 10 ml of methanol, and the resulting solution was purged with argon gas for 30 minutes. After that, 0.1072 g (0.42 mmol) of silver trifluoromethane sulfonic acid was added to the solution, and stirred for 15 hours at 50° C. After cooling to room temperature, filtration through a Celite layer was performed, and to the intermediate (D) which has been obtained by removing filtrate according to distillation under reduced pressure, 0.1458 g (0.56 mmol) of the ligand (L-a) and 20 ml of ethanol were added and refluxed with heating for 15 hours under argon atmosphere. After cooling to room temperature, the solvent was removed by distillation under reduced pressure. The obtained solids were dissolved in dichloromethane, and recrystallized by adding hexane thereto. After that, purification was carried out by using silica gel column chromatography (elution solution: mixture solvent of ethyl acetate and hexane), and the present invention compound (K-147) was obtained. The obtained amount was 0.0717 g (yield: 24.8%). Identification of the compound was carried out by using $^1$H-NMR and ESI-MS. The analysis data of the present invention compound (K-147) are shown below. The (K-147) obtained by this method was a facial isomer. Furthermore, ligand scrambling did not occur during the synthesis of the present invention compound (K-147).

$^1$H-NMR (400 MHz/acetone-$d_6$) δ: 8.68 (d, 1H), 8.34 (d, 1H), 8.08-8.12 (m, 2H), 7.85 (d, 1H), 7.72-7.80 (m, 5H), 7.68 (d, 1H), 7.63 (d, 2H), 7.37 (t, 2H), 7.23 (t, 1H), 7.13 (d, 1H), 7.05-7.09 (m, 2H), 6.82-6.90 (m, 5H), 6.70-6.75 (m, 2H), 2.52 (q, 2H), 1.07 (t, 3H)

ESI-MS: m/z=760.6

Example I-7

Synthesis of the Present Invention Compound (K-295)

[Chem. 29]

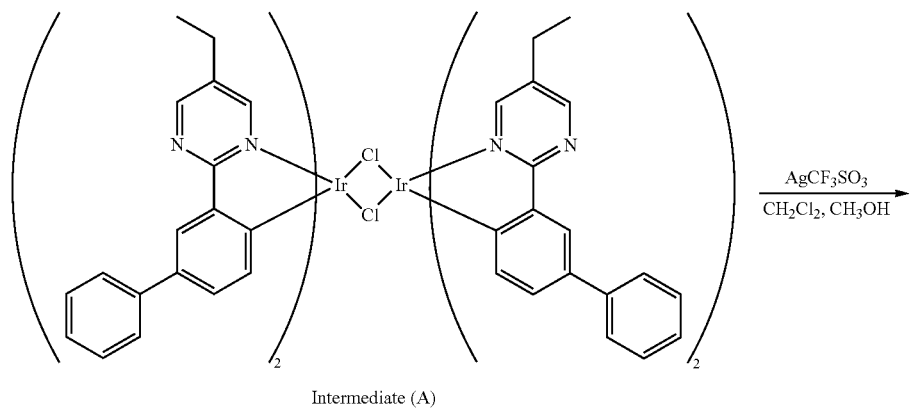

Intermediate (A)

-continued

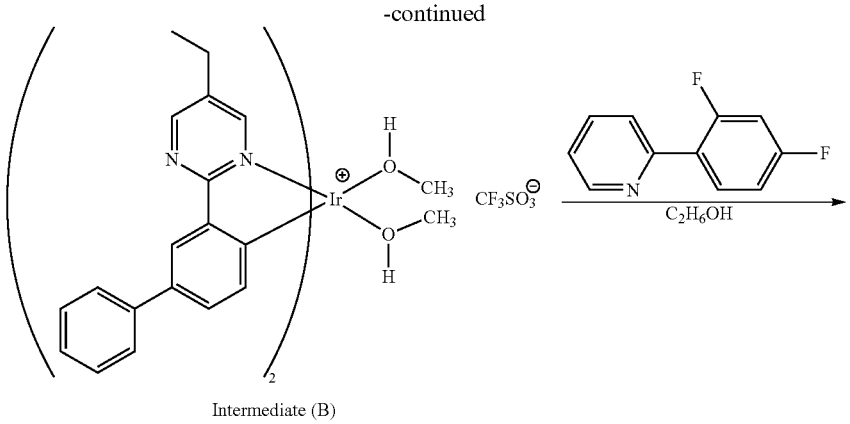

Intermediate (B)

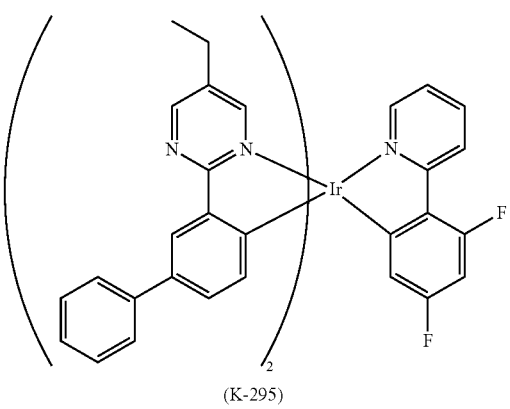

(K-295)

0.2001 g (0.13 mmol) of the intermediate (A) was dissolved in a mixture solvent containing 15 ml of dichloromethane and 5 ml of methanol, and the resulting solution was purged with argon gas for 30 minutes. After that, 0.0713 g (0.28 mmol) of silver trifluoromethane sulfonic acid was added to the solution, and stirred for 15 hours at 50° C. After cooling to room temperature, filtration through a Celite layer was performed, and to the intermediate (B) which has been obtained by removing filtrate according to distillation under reduced pressure, 30 ml of ethanol was added and argon bubbling was carried out for 30 minutes. Temperature of the resulting solution was increased to 75° C. or so, and then 5 mL of ethanol containing 0.0711 g (0.37 mmol) of 2-(2,4-difluorophenyl)pyridine was added dropwise and refluxed with heating for 3 days under argon atmosphere. After cooling to room temperature, the solvent was removed by distillation under reduced pressure. The obtained solids were purified by using silica gel column chromatography (elution solution: mixture solvent of ethyl acetate and hexane), and the present invention compound (K-295) was obtained. The obtained amount was 0.0908 g (yield: 38.8%). Identification of the compound was carried out by using $^1$H-NMR and ESI-MS. The analysis data of the present invention compound (K-295) are shown below. The (K-295) obtained by this method was a facial isomer. Furthermore, ligand scrambling did not occur during the synthesis of the present invention compound (K-295).

$^1$H-NMR (400 MHz/dichloromethane-d$_2$) δ: 8.55 (t, 2H), 8.35-8.38 (m, 2H), 8.29 (d, 1H), 8.13 (dd, 1H), 8.05 (d, 1H), 7.74 (td, 1H), 7.63-7.65 (m, 4H), 7.56 (d, 1H), 7.33-7.42 (m, 5H), 7.23-7.30 (m, 3H), 6.99-7.02 (m, 1H), 6.72 (d, 1H), 6.43-6.56 (m, 3H), 2.50 (m, 4H), 1.12 (m, 6H)

ESI-MS: m/z=902.6

Furthermore, synthesis and analysis data of the present invention compounds other than the above are shown below.

Example I-8

Synthesis of the Present Invention Compound (K-75)

By performing the same synthesis as Example I-1 except that 2-(biphenyl-4-yl)pyridine was used instead of 2-phenylpyridine, the present invention compound (K-75) as a facial isomer was obtained. The analysis data of the present invention compound (K-75) as a facial isomer are shown below.

$^1$H-NMR (400 MHz/dichloromethane-d$_2$) δ: 8.64 (dd, 2H), 8.35 (dd, 2H), 8.00 (d, 1H), 7.77 (d, 1H), 7.68-7.75 (m, 3H), 7.63-7.65 (m, 4H), 7.59 (d, 1H), 7.37-7.40 (m, 6H), 7.18-7.28 (m, 8H), 7.14 (d, 1H), 7.02 (dd, 1H), 6.98 (d, 1H), 6.94 (d, 1H) 2.49-2.58 (m, 4H), 1.12-1.20 (m, 6H)

ESI-MS: m/z=942.7

Furthermore, as a byproduct of the reaction, the present invention compound (K-219) as a facial isomer was obtained. The analysis data of the present invention compound (K-219) are shown below.

$^1$H-NMR (400 MHz/dichloromethane-d$_2$) δ: 8.51 (d, 2H), 8.35 (dd, 1H), 8.29 (d, 1H), 8.16 (d, 1H), 8.10 (dd, 1H), 8.03 (d, 1H), 7.88 (d, 1H), 7.74 (dd, 1H), 7.70 (d, 1H), 7.65 (d, 4H), 7.34-7.42 (m, 7H), 7.20-7.30 (m, 8H), 7.00 (t, 1H), 6.81 (d, 1H), 6.63 (d, 1H), 2.51 (q, 2H), 2.44 (q, 2H), 1.13 (t, 3H), 1.04 (t, 3H)

ESI-MS: m/z=942.1

Example I-9

Synthesis of the Present Invention Compound (K-99)

By performing the same synthesis as Example I-4 except that the operation of adding 2,4-diphenylpyridine after increasing the temperature of the reaction solution to 80° C. is modified to an operation of adding it at room temperature without temperature increase, the present invention compound (K-99) as a meridional isomer was obtained. The analysis data of the present invention compound (K-99) as a meridional isomer are shown below.

$^1$H-NMR (400 MHz/dichloromethane-d$_2$) δ: 8.51-8.52 (m, 2H), 8.36 (s, 1H), 8.30 (d, 1H), 8.22 (d, 1H), 8.09-8.11 (m, 2H), 7.91 (d, 1H), 7.77 (d, 1H), 7.73-7.02 (m, 21H), 6.82 (d, 1H), 6.61 (d, 1H), 2.51 (q, 2H), 2.45 (q, 2H), 1.13 (t, 3H), 1.06 (t, 3H)

ESI-MS: m/z=942.7

Example I-10

Synthesis of the Present Invention Compound (K-2)
Step 1 Synthesis of the Ligand (L-b)

[Chem. 30]

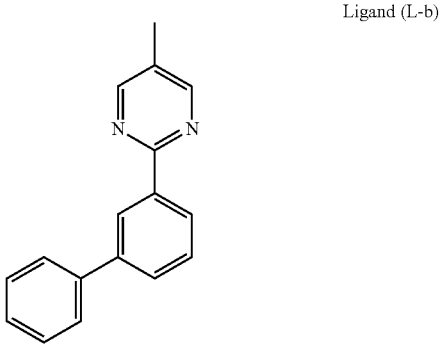

Ligand (L-b)

To a 3-neck flask, 5.18 g (40.3 mmol) of 2-chloro-5-methylpyrimidine, 9.26 g (46.8 mmol) of 3-biphenylboronic acid, 95 ml of 2 M aqueous solution of potassium carbonate, and 70 ml of 1,2-dimethoxyethane were added, and after purge with argon gas, 2.25 g (1.95 mmol) of tetrakis (triphenylphosphine) palladium (0) was added and refluxed with heating for 24 hours under argon atmosphere. The reaction solution was cooled to room temperature, the organic layer was then recovered, the solvent was removed by distillation under reduced pressure, and by performing purification using silica gel column chromatography (elution solution: dichloromethane), the ligand (L-b) was obtained. The obtained amount was 8.40 g (yield: 84.7%). Identification of the compound was carried out by using $^1$H-NMR. The analysis data of the ligand (L-b) are shown below.

$^1$H-NMR (400 MHz/CDCl$_3$) δ: 8.66-8.68 (m, 3H), 8.39 (d, 1H), 7.70-7.72 (m, 3H), 7.56 (t, 1H), 7.46 (t, 2H), 7.37 (t, 1H), 2.36 (s, 3H).

Step 2 Synthesis of the Present Invention Compound (K-2)

[Chem. 31]

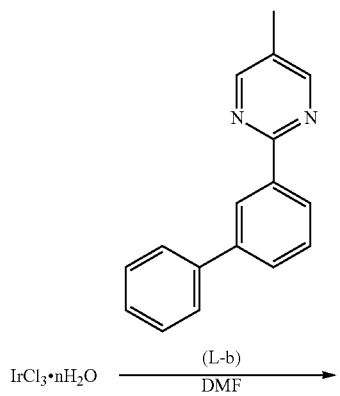

$$\text{IrCl}_3 \cdot \text{nH}_2\text{O} \xrightarrow[\text{DMF}]{\text{(L-b)}}$$

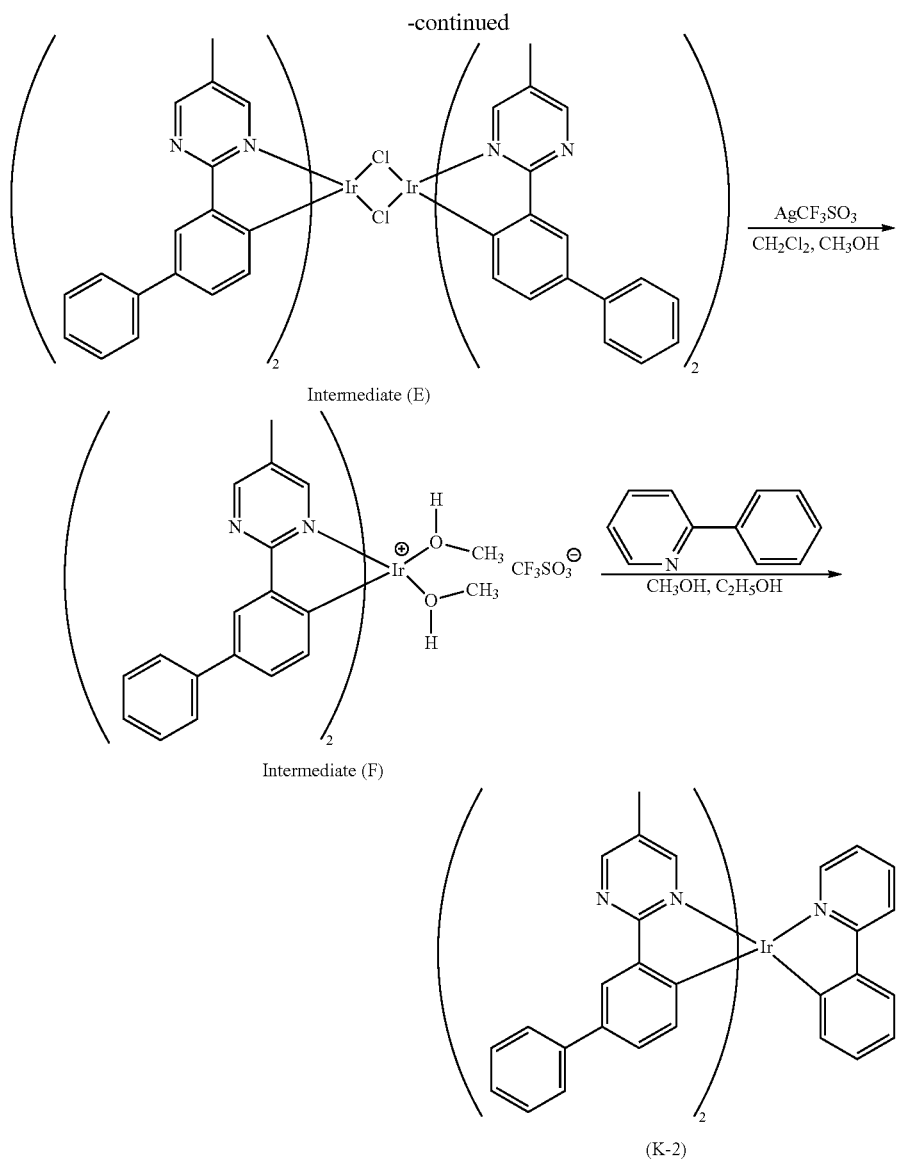

Intermediate (E)

Intermediate (F)

(K-2)

4.11 g (11.6 mmol) of iridium trichloride n hydrate, 6.00 g (24.4 mmol) of the ligand (L-b), 225 ml of DMF, and 25 ml of purified water were added, and after purge with argon gas for 30 minutes, irradiation with microwave (2450 MHz) was carried out for 30 minutes. After cooling the reaction solution to room temperature, the solvent was removed to about 10 ml by distillation under reduced pressure, and by adding methanol and purified water, solids were precipitated to obtain the intermediate (E). The obtained amount was 8.00 g (yield: 95.8%). 5.82 g (4.05 mmol) of the intermediates (E) which has been synthesized by the above method were dispersed in a mixture solvent containing 500 ml of dichloromethane and 500 ml of methanol, and the dispersion was purged with argon gas for 30 minutes. After that, 2.24 g (8.72 mmol) of silver trifluoromethane sulfonic acid was added to the dispersion, and stirred for 16 hours at room temperature. Then, filtration through a Celite layer was performed, and the intermediate (F) was obtained by removing filtrate according to distillation under reduced pressure. The obtained amount was 6.93 g (yield: 95.5%). To 5.00 g (5.58 mmol) of the intermediate (F), 1.94 g (12.50 mmol) of 2-phenylpyridine, 75 ml of methanol, and 175 ml of ethanol were added, and refluxed with heating for 14 hours under argon atmosphere. After cooling to room temperature, the solvent was removed by distillation under reduced pressure. The obtained solids were dissolved in dichloromethane, and recrystallized by adding methanol thereto. After that, recrystallization was carried out one more time by using dichloromethane and methanol to obtain the present invention compound (K-2). The obtained amount was 0.725 g (yield: 15.5%).

Identification of the compound was carried out by using $^1$H-NMR. The analysis data of the present invention compound (K-2) are shown below. The (K-2) obtained by this method was a facial isomer.

$^1$H-NMR (400 MHz/DMSO-$d_6$) δ: 8.74 (dd, 2H), 8.23 (t, 2H), 8.19 (d, 1H), 7.96 (d, 1H), 7.86 (t, 1H), 7.82 (d, 1H), 7.76 (d, 1H), 7.59-7.64 (m, 5H), 7.40 (t, 4H), 7.26-7.29 (m, 2H), 7.13-7.21 (m, 3H), 6.87 (t, 1H), 6.70-6.77 (m, 3H), 6.65 (d, 1H), 2.21 (s, 3H), 2.16 (s, 3H).

Example I-11

Synthesis of the Present Invention Compound (K-301)
Step 1 Synthesis of the Ligand (L-c)

[Chem. 32]

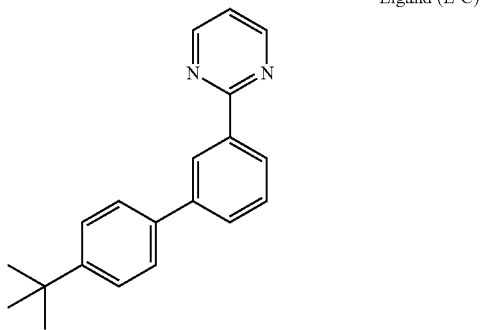

Ligand (L-C)

To a 3-neck flask, 10.3 g (64.8 mmol) of 2-bromopyrimidine, 14.0 g (69.7 mmol) of 3-bromophenylboronic acid, 150 ml of 2 M aqueous solution of potassium carbonate, and 110 ml of tetrahydrofuran were added, and after purge with argon gas, 3.65 g (3.16 mmol) of tetrakis (triphenylphosphine) palladium (0) was added and refluxed with heating for 16 hours under argon atmosphere. The reaction solution was cooled to room temperature, and then 13.5 g (75.8 mmol) of 4-tert-butylphenylboronic acid and 1.82 g (1.57 mmol) of tetrakis (triphenylphosphine) palladium (0) were added again thereto and then refluxed with heating for 16 hours under argon atmosphere again. The reaction solution was cooled to room temperature, the organic layer was then recovered, the solvent was removed by distillation under reduced pressure, and by performing purification using silica gel column chromatography (elution solution: dichloromethane), the ligand (L-c) was obtained. The obtained amount was 14.0 g (yield: 74.9%). Identification of the compound was carried out by using $^1$H-NMR. The analysis data of the ligand (L-c) are shown below.

$^1$H-NMR (400 MHz/CDCl$_3$) δ: 8.83 (d, 2H), 8.71 (s, 1H), 8.41 (d, 1H), 7.73 (d, 1H), 7.66 (d, 2H), 7.56 (t, 1H), 7.49 (d, 2H), 7.21 (t, 1H), 1.38 (s, 9H).

Step 2 Synthesis of the Present Invention Compound (K-301)

[Chem. 33]

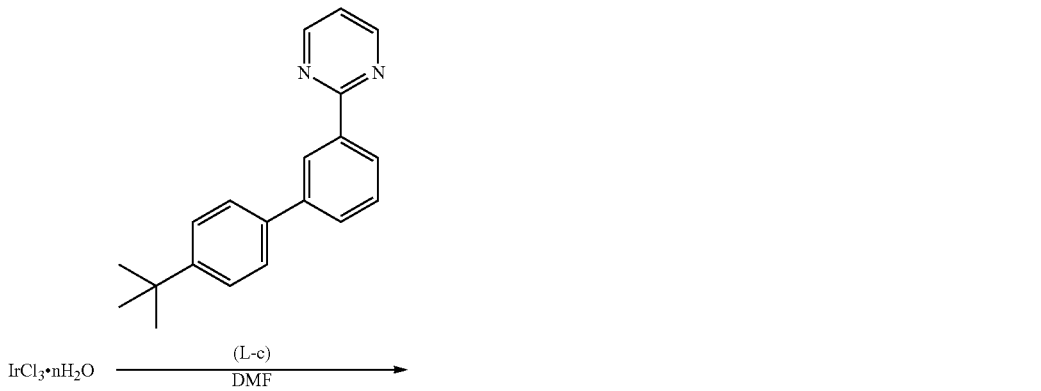

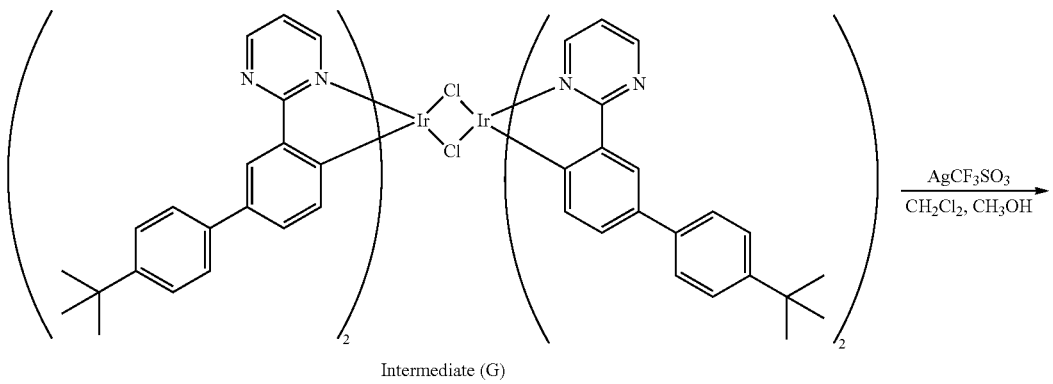

Intermediate (G)

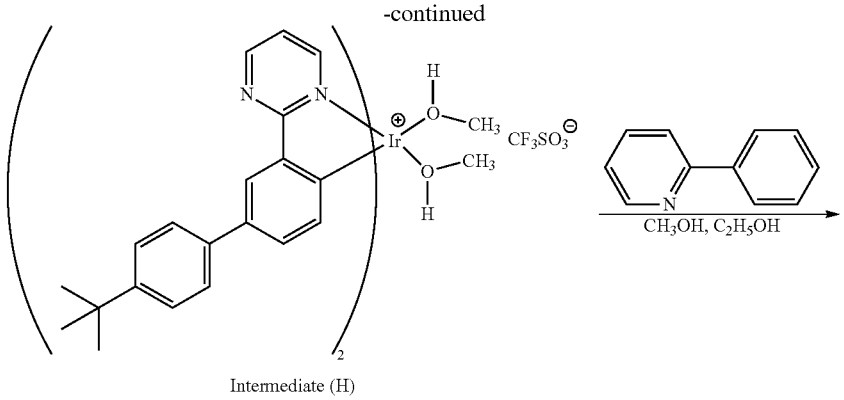

Intermediate (H)

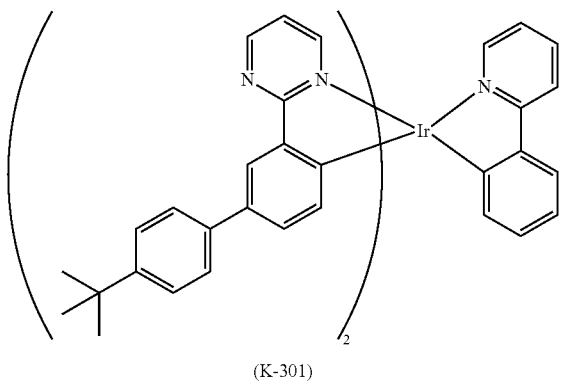

(K-301)

2.59 g (7.33 mmol) of iridium trichloride n hydrate, 4.30 g (14.9 mmol) of the ligand (L-c), 135 ml of DMF, and 15 ml of purified water were added, and after purge with argon gas for 30 minutes, irradiation with microwave (2450 MHz) was carried out for 30 minutes. After cooling the reaction solution to room temperature, the solvent was removed to about 10 ml by distillation under reduced pressure, and by adding methanol, solids were precipitated to obtain the intermediate (G). The obtained amount was 4.26 g (yield: 72.4%). 3.02 g of the intermediates (G) which has been synthesized according to the above method were dissolved in a mixture solvent containing 125 ml of dichloromethane and 125 ml of methanol, and the solution was purged with argon gas for 30 minutes. After that, 1.01 g (3.93 mmol) of silver trifluoromethane sulfonic acid was added to the solution, and refluxed with heating for 16 hours at 50° C. After cooling the reaction solution to room temperature, filtration through a Celite layer was performed, and the intermediate (H) was obtained by removing filtrate according to distillation under reduced pressure. The obtained amount was 3.62 g (yield: 98.1%). To 2.51 g (2.56 mmol) of the intermediate (H), 0.89 g (5.73 mmol) of 2-phenylpyridine, 30 ml of methanol, and 70 ml of ethanol were added, and refluxed with heating for 2 days under argon atmosphere. After cooling to room temperature, the solvent was removed by distillation under reduced pressure, purification was carried out by using silica gel column chromatography (elution solution: dichloromethane), and the present invention compound (K-301) was obtained. The obtained amount was 0.162 g (yield: 6.9%).

Identification of the compound was carried out by using $^1$H-NMR. The analysis data of the present invention compound (K-301) are shown below. The (K-301) obtained by this method was a facial isomer.

$^1$H-NMR (400 MHz/DMSO-$d_6$) δ: 8.56 (m, 2H), 8.25 (dd, 2H), 8.21 (d, 1H), 8.09 (dd, 1H), 7.82-7.89 (m, 2H), 7.77 (dd, 1H), 7.74 (d, 1H), 7.54-7.57 (m, 4H), 7.41-7.44 (m, 4H), 7.28 (t, 2H), 7.15-7.21 (m, 3H), 6.88 (t, 1H), 6.75-6.79 (m, 3H), 6.70 (d, 1H), 1.30 (s, 9H), 1.30 (s, 9H).

Example I-12

Synthesis of the Present Invention Compound (K-302)

[Chem. 34]

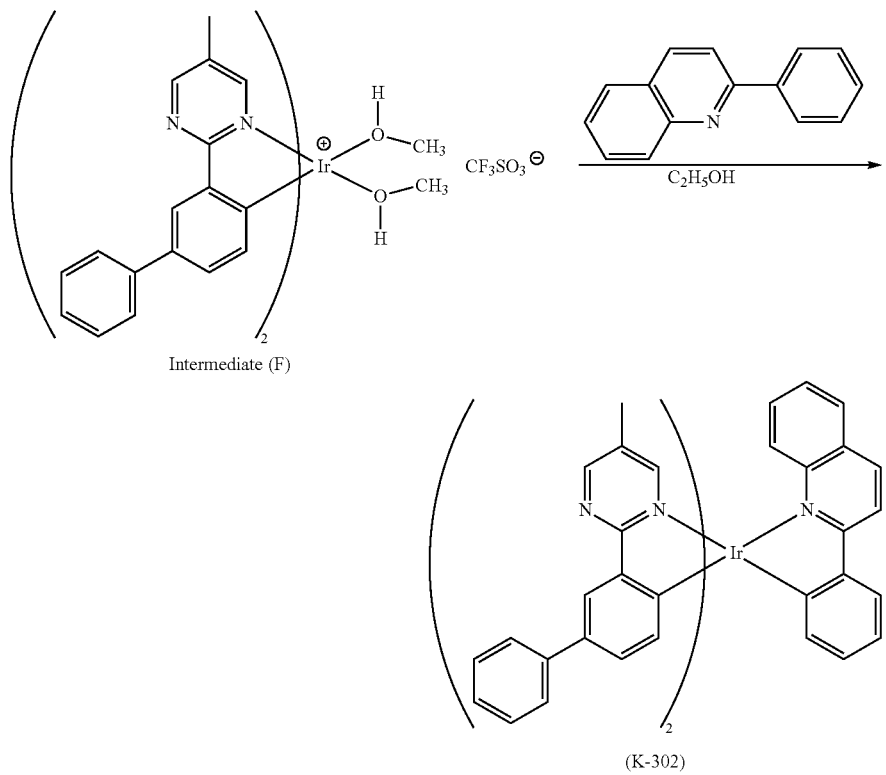

To 0.841 g (0.939 mmol) of the intermediate (F), 0.465 g (2.27 mmol) of 2-phenylquinoliene and 50 ml of ethanol were added, and refluxed with heating for 3 days under argon atmosphere. After cooling to room temperature, the solvent was removed by distillation under reduced pressure, and after dissolving in 25 ml of dichloromethane, irradiation with an UV lamp (wavelength: 365 nm) was carried out therefor for 3 hours, and the solvent was removed by distillation under reduced pressure. Thereafter, by performing purification using silica gel column chromatography (elution solution: dichloromethane), the present invention compound (K-302) was obtained. The obtained amount was 0.0007 g (yield: 0.08%).

Identification of the compound was carried out by using $^1$H-NMR. The analysis data of the present invention compound (K-302) are shown below.

$^1$H-NMR (400 MHz/DMSO-$d_6$) δ: 8.75 (t, 2H), 8.44 (s, 2H), 8.27 (d, 1H), 8.21 (d, 1H), 8.14 (d, 1H), 8.07 (d, 1H), 7.96 (d, 1H), 7.74 (d, 1H), 7.64-7.66 (m, 3H), 7.57 (d, 2H), 7.34-7.46 (m, 5H), 7.22-7.30 (m, 3H), 7.17 (dd, 1H), 7.07 (dd, 1H), 6.95 (t, 1H), 6.76 (t, 1H), 6.61 (d, 1H), 6.50 (dd, 2H), 2.24 (s, 3H), 2.06 (s, 3H).

Example I-13

Synthesis of the Present Invention Compound (K-303)

[Chem. 35]

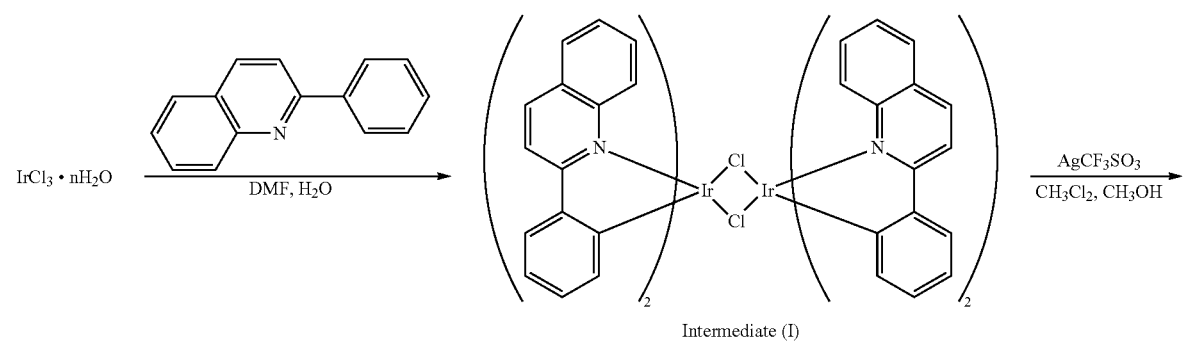

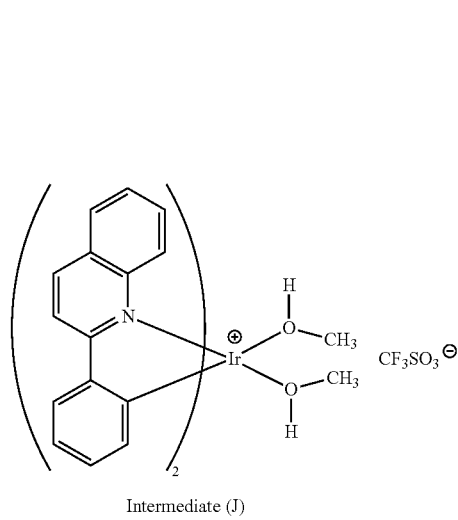

Intermediate (J)

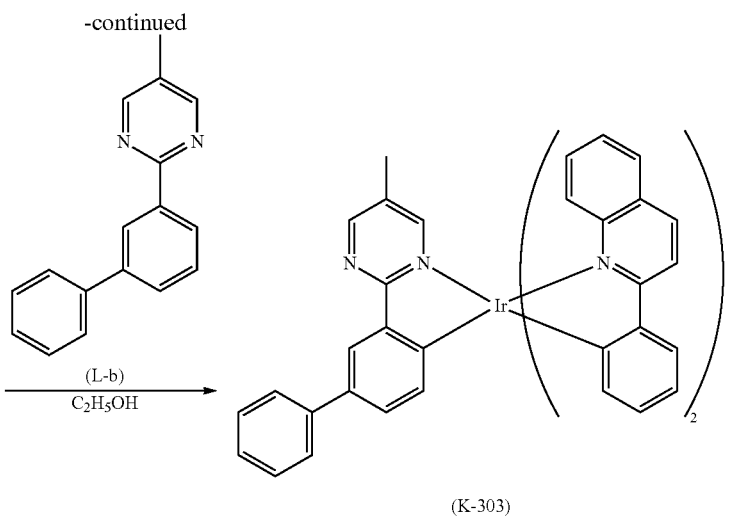

(K-303)

To a 3-neck flask, 3.00 g (8.23 mmol) of iridium trichloride n hydrate, 3.74 g of 2-phenylquinoline, 80 ml of 2-ethoxyethanol, and 20 ml of purified water were added, and refluxed with heating for 18 hours under argon atmosphere. The reaction solution was cooled to room temperature, filtered, and washed with methanol and purified water to obtain the intermediate (I). The obtained amount was 3.63 g (yield: 69.3%). 2.62 g (2.06 mmol) of the intermediate (I), 1.15 g (4.48 mmol) of silver trifluoromethane sulfonic acid, 140 ml of methanol, and 220 ml of dichloromethane were added to a 3-neck flask, and stirred for 24 hours at room temperature under argon atmosphere. The reaction solution was filtered through a Celite layer and the intermediate (J) was obtained by removing filtrate according to distillation under reduced pressure. The obtained amount was 3.31 g (yield: 98.8%). To 1.26 g (1.55 mmol) of the intermediate (J), 0.920 g (3.74 mmol) of the ligand (L-b) and 80 ml of ethanol were added, and refluxed with heating for 2 days under argon atmosphere. After cooling to room temperature, the solvent was removed by distillation under reduced pressure, and after dissolving in dichloromethane, irradiation with an UV lamp (wavelength: 365 nm) was carried out therefor for 3 hours, and the solvent was removed by distillation under reduced pressure. The obtained solids were dissolved in dichloromethane and recrystallized by adding methanol. Thereafter, by carrying out one more time the recrystallization with dichloromethane and methanol, the present invention compound (K-303) was obtained. The obtained amount was 0.619 g (yield: 47.2%). Identification of the compound was carried out by using $^{1}$H-NMR. The analysis data of the present invention compound (K-303) are shown below.

$^{1}$H-NMR (400 MHz/DMSO-$d_6$) δ: 8.69 (d, 1H), 8.52 (q, 2H), 8.41 (q, 2H), 8.10 (d, 1H), 8.03 (d, 1H), 8.01 (d, 1H), 7.89-7.95 (m, 3H), 7.72 (d, 1H), 7.59 (d, 1H), 7.54 (d, 2H), 7.39 (t, 1H), 7.34 (t, 2H), 7.29 (t, 1H), 7.22 (t, 1H), 7.15 (t, 1H), 7.06 (dd, 1H), 6.94 (t, 1H), 6.87 (t, 1H), 6.62-6.72 (m, 3H), 6.38-6.46 (m, 3H), 2.10 (s, 3H).

Next, the method for producing a facial isomer by using photoisomerization reaction of a meridional isomer according to the present invention is described.

Example II-1

Photoisomerization Reaction of the Present Invention Compound (K-99) as Meridional Isomer 0.5 mg of the present invention compound (K-99) as a meridional isomer was dissolved in 0.75 mL of dichloromethane-$d_2$ and added into an NMR tube. The tube was then irradiated with a UV lamp (wavelength: 365 nm) for 15 hours. As a result of the analysis by $^{1}$H-NMR, it was found that the meridional isomer has disappeared and completely photoisomerized to the facial isomer (K-99).

Next, descriptions are given for the light emission characteristics of the iridium complex according to the present invention.

Example III-1

Light Emission Characteristics of (K-3) in THF

The present invention compound (K-3) as a facial isomer was dissolved in THF, and after purge with argon gas, light emission spectrum (excitation wavelength: 350 nm) was measured at room temperature by using Absolute PL Quantum Yield Spectrometer (C9920) which is manufactured by Hamamatsu Photonics K. K, and as a result, strong light emission was shown (maximum light emission wavelength: 530 nm). The light emission quantum yield was 0.61.

Example III-2

Light Emission Characteristics of (K-51) in THF

The present invention compound (K-51) as a facial isomer was dissolved in THF, and after purge with argon gas, light emission spectrum (excitation wavelength: 350 nm) was measured at room temperature by using Absolute PL Quantum Yield Spectrometer (C9920) which is manufactured by Hamamatsu Photonics K. K, and as a result, strong light emission was shown (maximum light emission wavelength: 539 nm) as illustrated in FIG. 1. The light emission quantum yield was 0.83.

Example III-3

Light Emission Characteristics of (K-59) in THF

The present invention compound (K-59) as a facial isomer was dissolved in THF, and after purge with argon gas, light emission spectrum (excitation wavelength: 350 nm) was measured at room temperature by using Absolute PL Quantum Yield Spectrometer (C9920) which is manufactured by Hamamatsu Photonics K. K, and as a result, strong light emission was shown (maximum light emission wavelength: 531 nm). The light emission quantum yield was 0.61.

Example III-4

Light Emission Characteristics of (K-75) in THF

The present invention compound (K-75) as a facial isomer was dissolved in THF, and after purge with argon gas, light emission spectrum (excitation wavelength: 350 nm) was measured at room temperature by using Absolute PL Quantum Yield Spectrometer (C9920) which is manufactured by Hamamatsu Photonics K. K, and as a result, strong light emission was shown (maximum light emission wavelength: 528 nm). The light emission quantum yield was 0.74.

Example III-5

Light Emission Characteristics of (K-75) in THF

The present invention compound (K-75) as a meridional isomer was dissolved in THF, and after purge with argon gas, light emission spectrum (excitation wavelength: 350 nm) was measured at room temperature by using Absolute PL Quantum Yield Spectrometer (C9920) which is manufactured by Hamamatsu Photonics K. K, and as a result, strong light emission was shown (maximum light emission wavelength: 578 nm). The light emission quantum yield was 0.20.

Example III-6

Light Emission Characteristics of (K-99) in THF

The present invention compound (K-99) as a facial isomer was dissolved in THF, and after purge with argon gas, light emission spectrum (excitation wavelength: 350 nm) was measured at room temperature by using Absolute PL Quantum Yield Spectrometer (C9920) which is manufactured by Hamamatsu Photonics K. K, and as a result, strong light emission was shown (maximum light emission wavelength: 565 nm). The light emission quantum yield was 0.74.

Example III-7

Light Emission Characteristics of (K-123) in THF

The present invention compound (K-123) as a facial isomer was dissolved in THF, and after purge with argon gas, light emission spectrum (excitation wavelength: 350 nm) was measured at room temperature by using Absolute PL Quantum Yield Spectrometer (C9920) which is manufactured by Hamamatsu Photonics K. K, and as a result, strong light emission was shown (maximum light emission wavelength: 550 nm). The light emission quantum yield was 0.72.

Example III-8

Light Emission Characteristics of (K-123) in THF

The present invention compound (K-123) as a meridional isomer was dissolved in THF, and after purge with argon gas, light emission spectrum (excitation wavelength: 350 nm) was measured at room temperature by using Absolute PL Quantum Yield Spectrometer (C9920) which is manufactured by Hamamatsu Photonics K. K, and as a result, strong light emission was shown (maximum light emission wavelength: 578 nm). The light emission quantum yield was 0.26.

Example III-9

Light Emission Characteristics of (K-2) in THF

The present invention compound (K-2) as a facial isomer was dissolved in THF, and after purge with argon gas, light emission spectrum (excitation wavelength: 350 nm) was measured at room temperature by using Absolute PL Quantum Yield Spectrometer (C9920) which is manufactured by Hamamatsu Photonics K. K, and as a result, strong light emission was shown (maximum light emission wavelength: 541 nm). The light emission quantum yield was 0.70.

Example III-10

Light Emission Characteristics of (K-301) in THF

The present invention compound (K-301) as a facial isomer was dissolved in THF, and after purge with argon gas, light emission spectrum (excitation wavelength: 350 nm) was measured at room temperature by using Absolute PL Quantum Yield Spectrometer (C9920) which is manufactured by Hamamatsu Photonics K. K, and as a result, strong light emission was shown (maximum light emission wavelength: 538 nm). The light emission quantum yield was 0.70.

Example III-11

Light Emission Characteristics of (K-303) in Chloroform

The present invention compound (K-303) was dissolved in chloroform, and after purge with argon gas, light emission spectrum (excitation wavelength: 350 nm) was measured at room temperature by using Absolute PL Quantum Yield Spectrometer (C9920) which is manufactured by Hamamatsu Photonics K. K, and as a result, strong light emission was shown (maximum light emission wavelength: 622 nm). The light emission quantum yield was 0.65.

Comparative Example III-1

Light Emission Characteristics of the Comparative Compound (1) in THF

The Comparative Compound (1) as a facial isomer was dissolved in THF, and after purge with argon gas, light emission spectrum (excitation wavelength: 350 nm) was measured at room temperature by using Absolute PL Quantum Yield Spectrometer (C9920) which is manufactured by Hamamatsu Photonics K. K, and as a result, strong light emission was shown (maximum light emission wavelength: 527 nm). The light emission quantum yield was 0.64.

[Chem. 21]

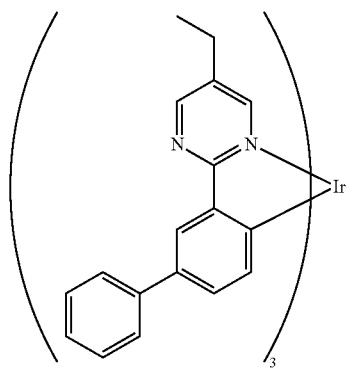

Comparative Compound (1)

From the above, it was found that the present invention compound shows very strong light emission in THF or chloroform. Furthermore, when light emission characteristics are compared between the facial isomer and meridional isomer, it was found that the facial isomer has the light emission quantum yield that is at least 2 times higher, and thus the facial isomer is more excellent as a light emitting material.

Next, in order to confirm the thermal stability and sublimability of the iridium complex of the present invention which is represented by General Formula (1), explanations are given for a sublimation purification experiment.

Example IV-1

Sublimation Purification of (K-3)

After adding 107 mg of the present invention compound (K-3) as a facial isomer to a sublimation purification instrument (P-200, manufactured by ALS Technology), sublimation purification was carried out over 18 hours at conditions including vacuum level of $1\times10^{-4}$ Pa and temperature of 300 to 335° C., and as a result, (K-3) was all sublimed. There were no sublimation residuals.

Furthermore, the purity of (K-3) was analyzed by using HPLC before and after the sublimation purification, and it was accordingly confirmed that the thermal stability is favorable.

Example IV-2

Sublimation Purification of (K-51)

After adding 166 mg of the present invention compound (K-51) as a facial isomer to a sublimation purification instrument (P-200, manufactured by ALS Technology), sublimation purification was carried out over 18 hours at conditions including vacuum level of $1\times10^{-4}$ Pa and temperature of 300 to 335° C., and as a result, a tiny amount sublimation residuals remained (2.8% of the addition amount). Furthermore, the purity of (K-51) was analyzed by using HPLC before and after the sublimation purification, and it was accordingly confirmed that the thermal stability is favorable.

Example IV-3

Sublimation Purification of (K-59)

After adding 124 mg of the present invention compound (K-59) as a facial isomer to a sublimation purification instrument (P-200, manufactured by ALS Technology), sublimation purification was carried out over 18 hours at conditions including vacuum level of $1\times10^{-4}$ Pa and temperature of 300 to 335° C., and as a result, (K-59) was all sublimed. There were no sublimation residuals. Furthermore, the purity of (K-59) was analyzed by using HPLC before and after the sublimation purification, and it was accordingly confirmed that the thermal stability is favorable.

Example IV-4

Sublimation Purification of (K-99)

After adding 84 mg of the present invention compound (K-99) as a facial isomer to a sublimation purification instrument (P-200, manufactured by ALS Technology), sublimation purification was carried out over 18 hours at conditions including vacuum level of $1\times10^{-4}$ Pa and temperature of 300 to 335° C., and as a result, (K-99) was all sublimed. There were no sublimation residuals. Furthermore, the purity of (K-99) was analyzed by using HPLC before and after the sublimation purification, and it was accordingly confirmed that the thermal stability is favorable.

Example IV-5

Sublimation Purification of (K-123)

After adding 146 mg of the present invention compound (K-123) as a facial isomer to a sublimation purification instrument (P-200, manufactured by ALS Technology), sublimation purification was carried out over 18 hours at conditions including vacuum level of $1\times10^{-4}$ Pa and temperature of 300 to 335° C., and as a result, a tiny amount sublimation residuals remained (1.7% of the addition amount). Furthermore, the purity of (K-123) was analyzed by using HPLC before and after the sublimation purification, and it was accordingly confirmed that the thermal stability is favorable.

Comparative Example IV-1

Sublimation Purification of the Comparative Compound (1)

After adding 107 mg of the Comparative Compound (1) as a facial isomer to a sublimation purification instrument (P-200, manufactured by ALS Technology), sublimation purification was carried out over 18 hours at conditions including vacuum level of $1\times10^{-4}$ Pa and temperature of 300 to 335° C., and as a result, a large amount of sublimation residuals remained (10.2% of the addition amount). Furthermore, the purity of the Comparative Compound (1) was analyzed by using HPLC before and after the sublimation purification, and it was accordingly confirmed that the thermal stability is favorable. Meanwhile, as a result of analyzing the sublimation residuals by HPLC, the purity was 93.1%, which is greatly lowered compared to the purity of 99.8% before the sublimation purification. It was accordingly recognized that, when compared to the present invention compound, the Comparative Compound (1) has very slow sublimation rate, and when it is subjected to sublimation purification at the same condition as the present invention compound, a decomposition reaction proceeds.

Next, the light emission characteristics of the iridium complex according to the present invention in a thin film state are described.

Example V-1

Light Emission Characteristics of (K-3) in Co-Vapor Deposited Film with CBP

The iridium complex (K-3) of the present invention as a facial isomer and 4,4'-N,N'-dicarbazole biphenyl (hereinbelow, referred to as CBP) (E-3) as a known host material were co-vapor deposited (30 nm) at 5:95 (mass concentration ratio) on a quartz substrate at vacuum level of $1\times10^{-4}$ Pa, then by using Absolute PL Quantum Yield Spectrometer (C9920) which is manufactured by Hamamatsu Photonics K. K., light emission spectrum (excitation wavelength: 340 nm) was measured at room temperature, and as a result, strong light emission was shown (maximum light emission wavelength: 535 nm). The light emission quantum yield was 0.88.

Example V-2

Light Emission Characteristics of (K-51) in Co-Vapor Deposited Film with CBP

The iridium complex (K-51) of the present invention as a facial isomer and CBP (E-3) as a known host material were co-vapor deposited (30 nm) at 5:95 (mass concentration ratio) on a quartz substrate at vacuum level of $1\times10^{-4}$ Pa, then by using Absolute PL Quantum Yield Spectrometer (C9920) which is manufactured by Hamamatsu Photonics K. K., light emission spectrum (excitation wavelength: 340 nm) was measured at room temperature, and as a result, strong light emission was shown (maximum light emission wavelength: 539 nm). The light emission quantum yield was 0.87.

Example V-3

Light Emission Characteristics of (K-59) in Co-Vapor Deposited Film with CBP

The iridium complex (K-59) of the present invention as a facial isomer and CBP (E-3) as a known host material were co-vapor deposited (30 nm) at 5:95 (mass concentration ratio) on a quartz substrate at vacuum level of $1\times10^{-4}$ Pa, then by using Absolute PL Quantum Yield Spectrometer (C9920) which is manufactured by Hamamatsu Photonics K. K., light emission spectrum (excitation wavelength: 340 nm) was measured at room temperature, and as a result, strong light emission was shown (maximum light emission wavelength: 535 nm). The light emission quantum yield was 0.86.

Example V-4

Light Emission Characteristics of (K-99) in Co-Vapor Deposited Film with CBP

The iridium complex (K-99) of the present invention as a facial isomer and CBP (E-3) as a known host material were co-vapor deposited (30 nm) at 5:95 (mass concentration ratio) on a quartz substrate at vacuum level of $1\times10^{-4}$ Pa, then by using Absolute PL Quantum Yield Spectrometer (C9920) which is manufactured by Hamamatsu Photonics K. K., light emission spectrum (excitation wavelength: 340 nm) was measured at room temperature, and as a result, strong light emission was shown (maximum light emission wavelength: 550 nm). The light emission quantum yield was 0.89.

Example V-5

Light Emission Characteristics of (K-123) in Co-Vapor Deposited Film with CBP

The iridium complex (K-123) of the present invention as a facial isomer and CBP (E-3) as a known host material were co-vapor deposited (30 nm) at 5:95 (mass concentration ratio) on a quartz substrate at vacuum level of $1\times10^{-4}$ Pa, then by using Absolute PL Quantum Yield Spectrometer (C9920) which is manufactured by Hamamatsu Photonics K. K., light emission spectrum (excitation wavelength: 340 nm) was measured at room temperature, and as a result, strong light emission was shown (maximum light emission wavelength: 544 nm) as shown in FIG. 2. The light emission quantum yield was 0.85.

Example V-6

Light Emission Characteristics of (K-2) in Co-Vapor Deposited Film with CBP

The iridium complex (K-2) of the present invention as a facial isomer and CBP (E-3) as a known host material were co-vapor deposited (30 nm) at 5:95 (mass concentration ratio) on a quartz substrate at vacuum level of $1\times10^{-4}$ Pa, then by using Absolute PL Quantum Yield Spectrometer (C9920) which is manufactured by Hamamatsu Photonics K. K., light emission spectrum (excitation wavelength: 340 nm) was measured at room temperature, and as a result, strong light emission was shown (maximum light emission wavelength: 540 nm). The light emission quantum yield was 0.88.

Example V-7

Light Emission Characteristics of (K-303) in Co-Vapor Deposited Film with CBP

The iridium complex (K-303) of the present invention and CBP (E-3) as a known host material were co-vapor deposited (30 nm) at 5:95 (mass concentration ratio) on a quartz substrate at vacuum level of $1\times10^{-4}$ Pa, then by using Absolute PL Quantum Yield Spectrometer (C9920) which is manufactured by Hamamatsu Photonics K. K., light emission spectrum (excitation wavelength: 340 nm) was measured at room temperature, and as a result, strong light emission was shown (maximum light emission wavelength: 600 nm). The light emission quantum yield was 0.88.

Comparative Example V-1

Light Emission Characteristics of the Comparative Compound (1) in Co-Vapor Deposited Film with CBP The Comparative Compound (1) as a facial isomer and CBP (E-3) as a known host material were co-vapor deposited (30 nm) at 5:95 (mass concentration ratio) on a quartz substrate at vacuum level of $1\times10^{-4}$ Pa, then by using Absolute PL Quantum Yield Spectrometer (C9920) which is manufactured by Hamamatsu Photonics K. K., light emission spectrum (excitation wavelength: 340 nm) was measured at room temperature, and as a result, strong light emission was shown (maximum light emission wavelength: 526 nm). The light emission quantum yield was 0.82.

From the above, it was found that the light emission quantum yield was very high, i.e., 0.85 or more, in a co-vapor deposited film having the present invention compound and CBP, and by having the present invention compound in a thin film state, it can be very suitably used as a light emitting material.

Next, characteristics of an organic electroluminescent light emitting device that is produced by using the iridium complex of the present invention represented by General Formula (1) are described.

Example VI-1

Evaluation of Characteristics of Organic Electroluminescent Light Emitting Device that is Produced by Using the Present Invention Compound (K-3)

With regard to a positive electrode, an alkali-free glass substrate on which a film is formed by patterning indium tin oxide (ITO) in comb-like shape with line width of 2 mm and film thickness of 100 nm (manufactured by Atsugi Micro Co., Ltd.) was used as transparent conductive supporting substrate. It was then subjected to ultrasonic cleaning in order of ultrapure water, acetone, and isopropyl alcohol (IPA), and subsequently, it was cleaned by boiling with IPA followed by drying. Subsequently, the substrate obtained after UV/ozone cleaning was used as a transparent conductive supporting substrate.

On top of the above transparent conductive supporting substrate, The following organic layer (i.e., hole injection layer, hole transport layer, light emitting layer, hole blocking layer, and electron transport layer) were sequentially formed by vacuum vapor deposition based on resistance heating in a vacuum chamber at $1 \times 10^{-4}$ Pa, and subsequently, according to mask exchange, an electrode layer with line width of 2 mm (i.e., electron injection layer and metal electrode layer) were sequentially formed to produce an organic electroluminescent light emitting device (device shape; square shape with 2 mm×2 mm, area of device; 0.04 cm²). Subsequently, a sealing operation was carried out in a glove box with a nitrogen atmosphere such that the device is not exposed to atmospheric air. On a periphery of a seal glass in which dents of 1.5 mm are created at the center part of a glass plate with thickness of 3 mm (manufactured by Senyo Shoji Co., Ltd.), a UV curable epoxy resin Denatite R (manufactured by Nagase ChemteX Corporation) was applied, and after the device with complete vapor-deposition was covered with the seal grass and it was crimped, masking of the device part was carried out by covering it with an aluminum plate. Then, by repeating 5 times a cycle which includes irradiation for 1 minute using an UV illuminator attached with shutter and blocking for 1 minute, sealing was carried out.

Hole injection layer (10 nm): Compound (E-1)

Hole transport layer (40 nm): Compound (E-2)

Light emitting layer (20 nm): Co-vapor deposition of the present invention compound (K-3) (mass concentration of 15%) and Compound (E-3) (mass concentration of 85%)

Hole blocking layer (10 nm): Compound (E-4)

Electron transport layer (30 nm): Compound (E-5)

Electron injection layer (0.5 nm): Compound (E-6)

Metal electrode layer (150 nm): Al

Structural formulae of the compounds (E-1) to (E-6) are shown below.

[Chem. 22]

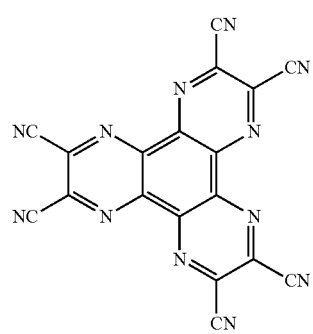
(E-1)

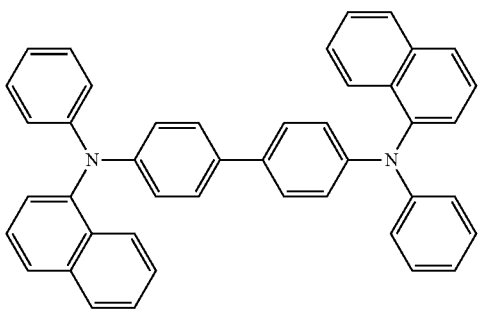
(E-2)

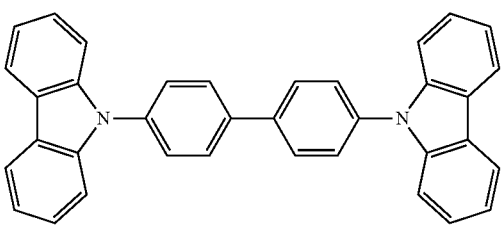
(E-3)

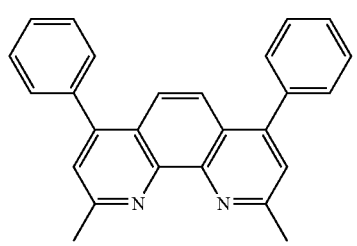
(E-4)

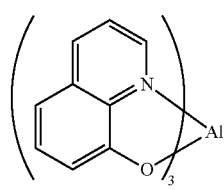
(E-5)

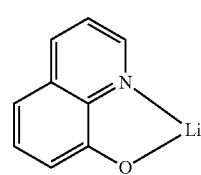
(E-6)

The obtained organic electroluminescent light emitting device was set in a sample holder of Integrating Sphere Unit A10094 for measuring EL external quantum yield, which is manufactured by Hamamatsu Photonics K. K, by using a source meter 2400 manufactured by Keithley, DC constant voltage was applied to have light illumination, and the luminance, light emission wavelength, and CIE chromaticity coordinate were measured by PMA-12, which is a multi-channel spectrophotometer manufactured by Hamamatsu Photonics K. K. As a result, CIE chromaticity was as follows: (x, y)=(0.360, 0.607), green light emission with light emission peak wavelength of 531 nm was obtained as shown in FIG. 3, the maximum luminance was 134000 cd/m² as shown in FIG. 4, and the maximum external quantum efficiency was 13.4% as shown in FIG. 5, showing obtainment of very favorable light emission characteristics.

Example VI-2

Evaluation of Characteristics of Organic Electroluminescent Light Emitting Device that is Manufactured by Using the Present Invention Compound (K-123)

Evaluation of characteristics was carried out by similarly producing an organic electroluminescent light emitting device except that, instead of the present invention compound (K-3) used in Example VI-1, the present invention compound (K-123) was used, and mass concentration of the present invention compound (K-123) and the compound (E-3) is changed to 10% and 90%, respectively. As a result, CIE chromaticity was as follows: (x, y)=(0.399, 0.578), yellowish green light emission with light emission peak wavelength of 545 nm was obtained as shown in FIG. 6, the maximum luminance was 103000 cd/m² as shown in FIG. 7, and the maximum external quantum efficiency was 13.0% as shown in FIG. 8, showing obtainment of very favorable light emission characteristics.

Example VI-3

Evaluation of Characteristics of Organic Electroluminescent Light Emitting Device that is Manufactured by Using the Present Invention Compound (K-51)

Evaluation of characteristics was carried out by similarly producing an organic electroluminescent light emitting device except that, instead of the present invention compound (K-3) used in Example VI-1, the present invention compound (K-51) was used. As a result, CIE chromaticity was as follows: (x, y)=(0.408, 0.574), yellowish green light emission with light emission peak wavelength of 538 nm was obtained, the maximum luminance was 115400 cd/m², and the maximum external quantum efficiency was 13.1%, showing obtainment of very favorable light emission characteristics.

Example VI-4

Evaluation of Characteristics of Organic Electroluminescent Light Emitting Device that is Manufactured by Using the Present Invention Compound (K-99)

Evaluation of characteristics was carried out by similarly producing an organic electroluminescent light emitting device except that, instead of the present invention compound (K-3) used in Example VI-1 the present invention compound (K-99) (facial isomer) was used. As a result, CIE chromaticity was as follows: (x, y)=(0.425, 0.554), yellow light emission with light emission peak wavelength of 551 nm was obtained, the maximum luminance was 95000 cd/m², and the maximum external quantum efficiency was 13.5%, showing obtainment of very favorable light emission characteristics.

As described in the above, the iridium complex of the present invention which is represented by General Formula (1) is a novel compound which has excellent thermal stability and sublimability and exhibits high light emission quantum yield, and when it is used for an organic light emitting device, an organic light emitting device with favorable light emission characteristics can be produced. Furthermore, from the viewpoint that the organic light emitting device using the compound exhibits light emission with high luminance in the visible light range, it is very suitable in the field of display device, display, backlight, and light source for lighting, or the like.

What is claimed is:

1. An iridium complex being represented by the following General Formula (1):

[Chem. 1]

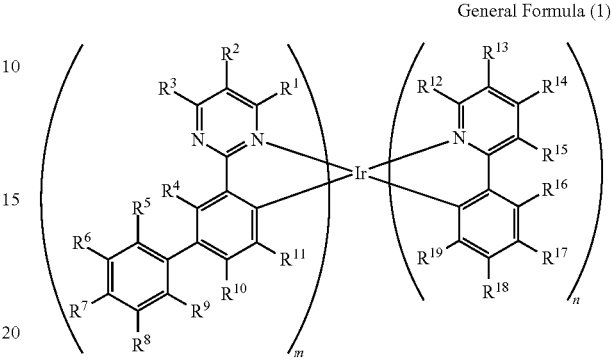

General Formula (1)

(in General Formula (i), N represents a nitrogen atom and Ir represents an iridium atom; $R^1$ to $R^{11}$ and $R^{13}$, $R^{14}$, and $R^{18}$ each independently represent a hydrogen atom, an alkyl group with 1 to 30 carbon atoms, an aryl group with 6 to 30 carbon atoms, a halogen atom, or a cyano group; $R^{12}$, $R^{15}$ to $R^{17}$ and $R^{19}$ each independently represent a hydrogen atom, an alkyl group with 1 to 30 carbon atoms, a halogen atom, or a cyano group; and m is an integer of 1 or 2, n is an integer of 1 or 2, and m+n is 3), wherein the iridium complex represented by General Formula (1) is at least one compound selected from the group consisting of: a compound represented by General Formula (9), a compound represented by General Formula (10), and a compound represented by General Formula (12)

[chem. 13]

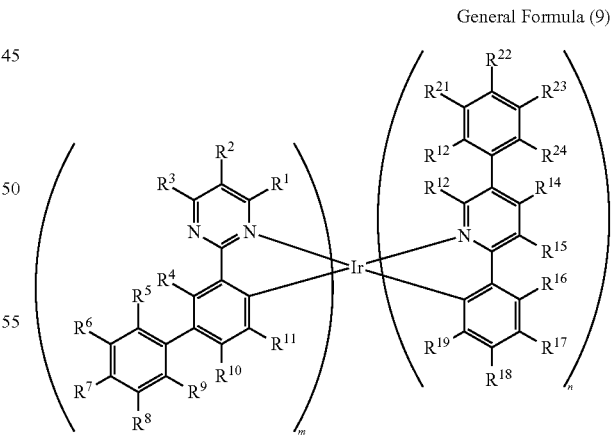

General Formula (9)

(in General Formula (9), $R^1$ to $R^{12}$ and $R^{14}$ to $R^{19}$ have the same meaning as $R^1$ to $R^{12}$ and $R^{14}$ to $R^{19}$ in General Formula (1), $R^{20}$ to $R^{24}$ each independently represent a hydrogen atom, an alkyl group with 1 to 30 carbon atoms, an aryl group with 6 to 30 carbon atoms, a halogen atom, or a cyano group)

[chem.14]

General Formula (10)

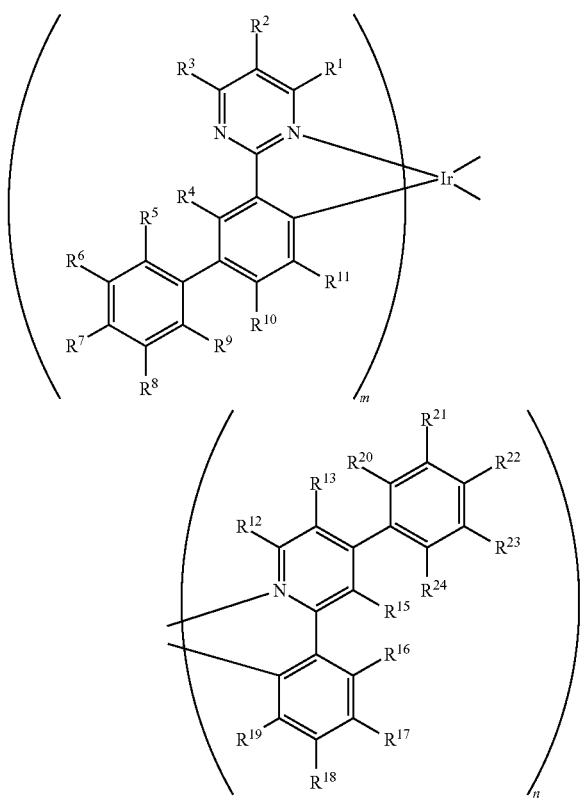

(in General Formula (10), $R^1$ to $R^{13}$ and $R^{15}$ to $R^{19}$ have the same meaning as $R^1$ to $R^{13}$ and $R^{15}$ to $R^{19}$ in General Formula (1), $R^{20}$ to $R^{24}$ each independently represent a hydrogen atom, an alkyl group with 1 to 30 carbon atoms, an aryl group with 6 to 30 carbon atoms, a halogen atom, or a cyano group)

[chem. 16]

General Formula (12)

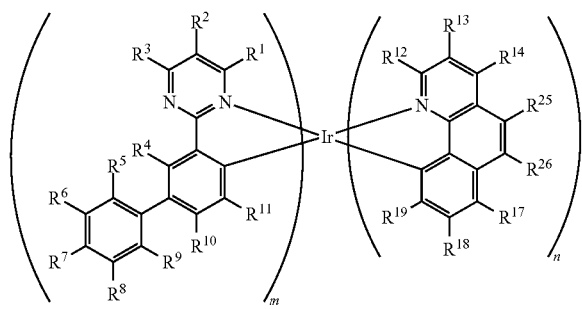

(in General Formula (12), $R^1$ to $R^{14}$ and $R^{17}$ to $R^{19}$ have the same meaning as $R^1$ to $R^{14}$ and $R^{17}$ to $R^{19}$ in General Formula (1), $R^{25}$ and $R^{26}$ each independently represent a hydrogen atom, an alkyl group with 1 to 30 carbon atoms, an aryl group with 6 to 30 carbon atoms, a halogen atom, or a cyano group), and wherein the iridium complex is a facial isomer.

2. The iridium complex according to claim 1, wherein $R^{12}$ and $R^{14}$ to $R^{19}$ are a hydrogen atom or an alkyl group with 1 to 30 carbon atoms in General Formula (9);

$R^{12}$, $R^{13}$ and $R^{15}$ to $R^{19}$ are a hydrogen atom or an alkyl group with 1 to 30 carbon atoms in General Formula (10); or $R^{12}$ to $R^{14}$ and $R^{17}$ to $R^{19}$ are a hydrogen atom or an alkyl group with 1 to 30 carbon atoms in General Formula (12).

3. The iridium complex according to claim 1, wherein $R^{18}$ is an aryl group with 6 to 30 carbon atoms.

4. The iridium complex according to claim 1, wherein at least one of $R^{12}$ and $R^{14}$ to $R^{19}$ is a halogen atom in General Formula (9);

at least one of $R^{12}$, $R^{13}$ and $R^{15}$ to $R^{19}$ is a halogen atom in General Formula (10); or at least one of $R^{12}$ to $R^{14}$ and $R^{17}$ to $R^{19}$ is a halogen atom in General Formula (12).

5. The iridium complex according to claim 1, wherein all of $R^4$, $R^5$, $R^9$, and $R^{10}$ are a hydrogen atom.

6. The iridium complex according to claim 1, wherein m is 2 and n is 1.

7. The iridium complex according to claim 1, wherein m is 1 and n is 2.

8. The iridium complex according to claim 1, wherein the aryl group is substituted with an alkyl group, a halogen atom, or a cyano group.

9. The iridium complex according to claim 1, wherein adjacent $R^{14}$ to $R^{19}$ bind to each other to form a condensed ring in General Formula (9);

adjacent $R^{12}$ and $R^{13}$, and $R^{15}$ to $R^{19}$ bind to each other to form a condensed ring in General Formula (10); or adjacent $R^{12}$ to $R^{14}$ and R17 to $R^{19}$ bind to each other to form a condensed ring in General Formula (12).

10. The iridium complex according to claim 1, wherein the alkyl group have substituents having an aryl group, a halogen atom, or a cyano group.

11. A light emitting material comprising the iridium complex described in claim 1.

12. An organic light emitting device comprising the light emitting material described in claim 11.

* * * * *